US007718810B2

(12) United States Patent
Ravikumar et al.

(10) Patent No.: US 7,718,810 B2
(45) Date of Patent: May 18, 2010

(54) SUPPORTS FOR OLIGOMER SYNTHESIS

(75) Inventors: Vasulinga Ravikumar, Carlsbad, CA (US); Muthiah Manoharan, Weston, MA (US); Andrei P. Guzaev, Vista, CA (US); Zhiwei Wang, Carlsbad, CA (US); Raju K. Kumar, San Marcos, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 19 days.

(21) Appl. No.: 12/175,206

(22) Filed: Jul. 17, 2008

(65) Prior Publication Data

US 2009/0131682 A1 May 21, 2009

Related U.S. Application Data

(63) Continuation of application No. 11/622,325, filed on Jan. 11, 2007, now Pat. No. 7,576,119, which is a continuation of application No. 10/989,197, filed on Nov. 15, 2004, now Pat. No. 7,202,264, which is a continuation-in-part of application No. 10/770,226, filed on Feb. 2, 2004, now abandoned, said application No. 10/989,197.

(60) Provisional application No. 60/564,649, filed on Apr. 21, 2004, provisional application No. 60/530,477, filed on Dec. 16, 2003, provisional application No. 60/520,179, filed on Nov. 13, 2003, provisional application No. 60/444,363, filed on Feb. 1, 2003.

(51) Int. Cl.
C07D 491/18 (2006.01)
(52) U.S. Cl. ..................................................... 548/431
(58) Field of Classification Search ........................ None
See application file for complete search history.

(56) References Cited

U.S. PATENT DOCUMENTS

| 5,869,696 | A | 2/1999 | Reddy et al. |
| 5,886,193 | A | 3/1999 | McLean et al. |
| 6,166,239 | A | 12/2000 | Manoharan |
| 6,294,664 | B1 | 9/2001 | Ravikumar et al. |
| 6,310,198 | B1 | 10/2001 | Tang et al. |
| 6,429,309 | B1 | 8/2002 | Kwiatkowski et al. |
| 6,653,468 | B1 | 11/2003 | Guzaev et al. |
| 6,953,679 | B2 * | 10/2005 | Salvati et al. ............... 435/121 |
| 2004/0152905 | A1 | 8/2004 | Guzaev et al. |
| 2005/0119228 | A1 | 6/2005 | Salvati et al. |

FOREIGN PATENT DOCUMENTS

| DE | 4117369 | 12/1992 |
| JP | 7-096677 | 4/1995 |
| WO | WO 97/23497 | 7/1997 |

| WO | WO 03/062241 | 7/2003 |

OTHER PUBLICATIONS

Antopolsky et al., "Towards a general method for the stepwise-phase synthesis of peptide-oligonucleotide conjugates" Tetrahedron Lett. (2002) 43:527-530.
Azhayev, "A New Universal Solid Support for Oligonucleotide Synthesis" Tetrahedron (1999) 55(3): 787-800.
Azhayev et al., "Amide group assisted 3'-dephosphorylation of oligonucleotides synthesized on universal A-supports" Tetrahedron (2001) 57(23):4977-4986.
Biagini et al., "The Synthesis of N-Norbornenyl-Amino Acids and Esters: Monomers for the Preparation of Well Defined Polymers" Tetrahedron (1995) 51(26):7247-7262.
Crea et al., "Synthesis of oligonucleotides on cellulose by a phosphotriester method" Nucleic Acids Res. (1980) 8(10):2331-2348.
Guzaev et al., "A Conformationally Preorganized Universal Solid Support for Efficient Oligonucleotide Synthesis" J. Am. Chem. Soc. (2003) 125(9):2380-2381.
Lee et al., "Synthesis and Biological Activities of Polymers Containing exo-3,6-Epoxy-1,2,3,6-Tetrahydrophthalic Glycinylimide" J. Appl. Polymer Sci. (1996) 62:557-565.
Lee et al., "Synthesis and Biological Activity of Medium Range Molecular Weight Polymers Containing exo-3,6-epoxy-1,2,3,6-tetrahydrophthalimido-caproic acid" Polymer Int. (2001) 50:1010-1015.
Liu et al., "Synthesis of 5,6-Dehydronorcantharidin Derivatives of Substituted Aromatic Amine and Their Anti-Tumor Activities" Chinese J. Org. Chem. (2002) 22(10):761-767.
Lyttle et al., "A new universal linker for solid phase DNA synthesis" Nucleic Acids Res. (1996) 24(14):2793-2798.
Lyttle et al., "A Phosphate Bound Universal Linker for DNA Synthesis" Nucleosides Nucleotides (1999) 18(8):1809-1824.
Maynard et al., "Synthesis of Norbornenyl Polymers and Bioactive Oligopeptides by Ring-Opening Metathesis Polymerization" Macromolecules (2000) 33:6239-6248.
Mccluskey et al., "The First Two Cantharidin Analogues Displaying PP1 Selectivity" Bioorg. Med. Chem. Lett. (2002) 12:391-393.
Nelson et al., "3'-Terminal Modification of Oligonucleotides Using a Universal Solid Support" Nucleosides Nucleotides (1997) 16(10 &11):1951-1959.
Nelson et al., "Rainbow Universal CPG: A Versatile Solid Support for Oligonucleotide Synthesis" BioTechniques (1997) 22:752-756.
Scheuer-Larsen et al., "Introduction of a Universal Solid Support for Oligonucleotide Synthesis" Nucleosides Nucleotides (1997) 16(1 &2):67-80.
Schwartz et al., "A Universal Adapter for Chemical Synthesis of DNA or RNA on any Single Type of Solid Support" Tetrahedron Lett. (1995) 36(1):27-30.

(Continued)

Primary Examiner—Kamal A Saeed
(74) Attorney, Agent, or Firm—ISIS Patent Department

(57) ABSTRACT

Universal linkers, their facile processes of manufacture and methods of using the same are provided.

31 Claims, No Drawings

OTHER PUBLICATIONS

Scott et al., "A Universal Support for Oligonucleotide Synthesis" Innovation and Perspectives in Solid Phase Synthesis, Epton, R. (ed.) (1994) pp. 115-124.

Reg. No. 41532-47-2 "Isobenzofuran-4,7-imine-1,3-dione,3a,4,7,7a-tetrahydro-8-methyl-(9CI)," SciFinder, Aug. 29, 2002, 2 pp. (abstract only).

Reg. No. 99237-90-8 "Isobenzofuran-4,7-imine-1,3-dione,8 acetyl-3a,4,7,7a-tetrahydro-(3aa,4a,7a,7aa)- (9CI)," SciFinder, Aug. 29, 2002, 2 pp. (abstract only).

International Search Report for Application No. PCT/US2004/038325 dated Apr. 27, 2005 (DVCM0010W0).

* cited by examiner

SUPPORTS FOR OLIGOMER SYNTHESIS

CROSS REFERENCE TO RELATED APPLICATIONS

This application is a continuation of U.S. application Ser. No. 11/622,325, filed Jan. 11, 2007, which is a continuation of U.S. application Ser. No. 10/989,197, filed Nov. 15, 2004 and now U.S. Pat. No. 7,202,264, which is a continuation in part of U.S. application Ser. No. 10/770,226, filed Feb. 2, 2004, now abandoned, which claims benefit of U.S. Provisional Application Ser. No. 60/444,363, filed Feb. 1, 2003. U.S. application Ser. No. 10/989,197 also claims benefit of U.S. Provisional Application Ser. No. 60/520,179, filed Nov. 13, 2003, U.S. Provisional Application Ser. No. 60/530,477, filed Dec. 16, 2003, and U.S. Provisional Application Ser. No. 60/564,649, filed Apr. 21, 2004. Each of the foregoing applications is hereby incorporated by reference herein in its entirety.

SEQUENCE LISTING

The present application is being filed along with a Sequence Listing in electronic format. The Sequence Listing is provided as a file entitled DVCM0023USC2SEQ.txt, created on Jul. 15, 2008 which is 4 KB in size. The information in the electronic format of the Sequence Listing is incorporated herein by reference in its entirety.

FIELD OF THE INVENTION

The disclosure herein provides teaching of compounds, compositions and methods of use relating to oligomer synthesis. For example, the disclosure provides supports for synthesis of oligonucleotides and modified oligonucleotides, compositions comprising such supports and methods of using such supports in the synthesis of oligonucleotides.

BACKGROUND OF THE INVENTION

Oligonucleotides have been used in various biological and biochemical applications. They have been used as primers and probes for the polymerase chain reaction (PCR), as antisense agents used in target validation, drug discovery and development, as ribozymes, as aptamers, and as general stimulators of the immune system. As the popularity of oligonucleotides has increased, the need for producing greater sized batches, and greater numbers of small-sized batches, has increased at pace. Additionally, there has been an increasing emphasis on reducing the costs of oligonucleotide synthesis, and on improving the purity and increasing the yield of oligonucleotide products.

A number of innovations have been introduced to the art of oligonucleotide synthesis. Amongst these innovations have been the development of excellent orthogonal protecting groups, activators, reagents, and synthetic conditions. The oligonucleotides themselves have been subject to a variety of modifications and improvements. Amongst these are chemistries that improve the affinity of an oligonucleotide for a specific target, that improve the stability of an oligonucleotide in vivo, that enhance the pharmacokinetic (PK) and toxicological (Tox) properties of an oligonucleotide, etc. These novel chemistries generally involve a chemical modification to one or more of the constituent parts of the oligonucleotide.

The term "oligonucleotide" thus embraces a class of compounds that include naturally-occurring, as well as modified, oligonucleotides. Both naturally-occurring and modified oligonucleotides have proven useful in a variety of settings, and both may be made by similar processes, with appropriate modifications made to account for the specific modifications adopted. A naturally occurring oligonucleotide, i.e. a short strand of DNA or RNA may be envisioned as being a member of the following generic formulas, denominated oligo-RNA and oligo-DNA, respectively, below:

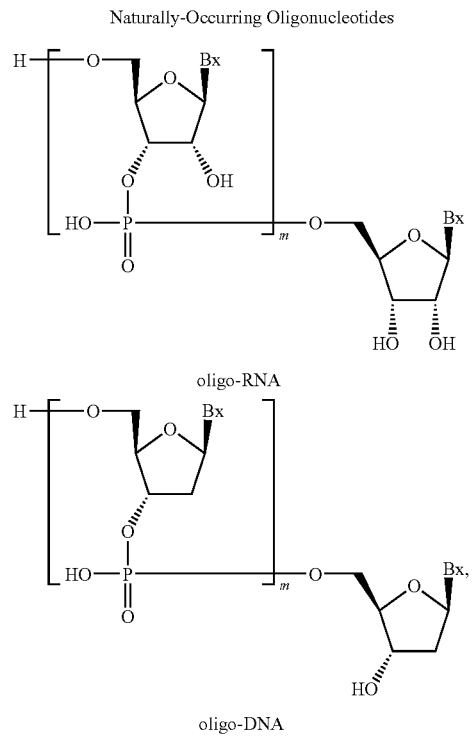

Naturally-Occurring Oligonucleotides oligo-RNA oligo-DNA wherein m is an integer of from 1 to about 100, and Bx is one of the naturally occurring nucleobases.

Physiologic pH, an oligonucleotide occurs as the anion, as the phosphate easily dissociates at neutral pH, and an oligonucleotide will generally occur in solid phase, whether amorphous or crystalline, as a salt. Thus, unless otherwise modified, the term "oligonucleotide" encompasses each of the anionic, salt and free acid forms above.

In essence, a naturally occurring oligonucleotide may be thought of as being an oligomer of m monomeric subunits represented by the following nucleotides:

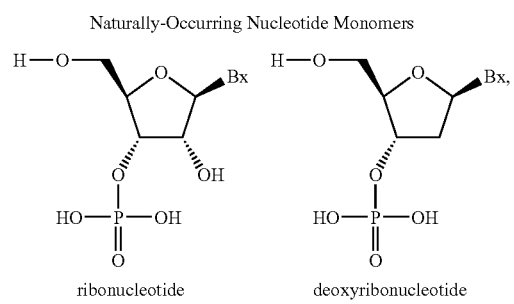

Naturally-Occurring Nucleotide Monomers ribonucleotide          deoxyribonucleotide wherein each Bx is a nucleobase, wherein the last residue is a nucleoside (i.e. a nucleotide without the 3'-phosphate group).

As mentioned above, various chemistry modifications have been made to oligonucleotides, in order to improve their affinity, stability, PK, Tox, and other properties. In general, the term oligonucleotide, as now used in the art, encompasses inter alia compounds of the formula:

Oligonucletoides (General)

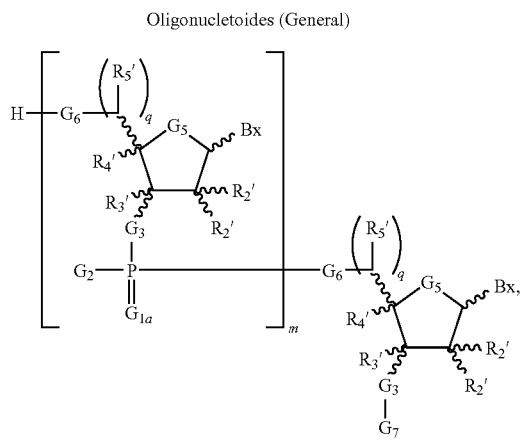

wherein m is an integer from 1 to about 100, each $G_{1a}$ is O or S, each $G_2$ is OH or SH, each $G_3$ is O, S, $CH_2$, or NH, each $G_5$ is a divalent moiety such as O, S, $CH_2$, CFH, $CF_2$, —CH=CH—, etc., each $R_2'$ is H, OH, O-rg, wherein rg is a removable protecting group, a 2'-substituent, or together with $R_4'$ forms a bridge, each $R_3'$ is H, a substituent, or together with $R_4'$ forms a bridge, each $R_4'$ is H, a substituent, together with $R_2'$ forms a bridge, together with $R_3$, forms a bridge, or together with $R_5'$ forms a bridge, each q is 0 or 1, each $R_5'$ is H, a substituent, or together with $R_4'$ forms a bridge, each $G_6$ is O, S, $CH_2$ or NH, and each $G_7$ is H, $PO_3H_2$, or a conjugate group, and each Bx is a nucleobase, as described herein (i.e. naturally occurring or modified).

The standard synthetic methods for oligonucleotides include the solid phase methods first described by Caruthers et al. (See, for example, U.S. Pat. No. 5,750,666, incorporated herein by reference, especially columns 3-58, wherein starting materials and general methods of making oligonucleotides, and especially phosphorothioate oligonucleotides, are disclosed, which parts are specifically incorporated herein by reference.) These methods were later improved upon by Köster et al. (See, for example, U.S. Pat. No. RE 34,069, which is incorporated herein by reference, especially columns, wherein are disclosed, which parts are specifically incorporated herein by reference.) These methods have further been improved upon by various inventors, as discussed in more detail below. Methods of synthesizing RNA are disclosed in, inter alia, U.S. Pat. Nos. 6,111,086, 6,008,400, and 5,889,136, each of which is incorporated herein in its entirety. Especially relevant are columns 7-20 of U.S. Pat. No. 6,008,400, which are expressly incorporated herein by reference.

The general process for manufacture of an oligonucleotide by the Köster et al. method may be described as follows:

First, a synthesis primer is prepared by covalently linking a suitable nucleoside to a solid support medium (SS) through a linker. Such a synthesis primer is as follows:

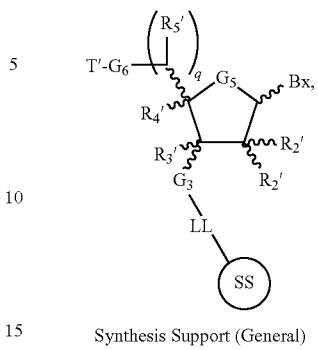

Synthesis Support (General)

wherein SS is the solid support medium, LL is a linking group that links the nucleoside to the solid support medium via $G_3$. The linking group is generally a di-functional group, covalently binds the ultimate 3'-nucleoside (and thus the nascent oligonucleotide) to the solid support medium during synthesis, but which is cleaved under conditions orthogonal to the conditions under which the 5'-protecting group, and if applicable any 2'-protecting group, are removed. T' is a removable protecting group, and the remaining variables have already been defined, and are described in more detail herein. Suitable synthesis primers may be acquired from Amersham Biosciences under the brand name Primer Support 200™. The support medium having the synthesis primer bound thereto may then be swelled in a suitable solvent, e.g. acetonitrile, and introduced into a column of a suitable solid phase synthesis instrument, such as one of the synthesizers available form Amersham Biosciences, such as an ÄKTA Oligopilot™, or OligoProcess™ brand DNA/RNA synthesizer.

Synthesis is carried out from 3'- to 5'-end of the oligomer. In each cycle, the following steps are carried out: (1) removal of T', (2) coupling, (3) oxidation, (4) capping. Each of the steps (1)-(4) may be, and generally is, followed by one or more wash steps, whereby a clean solvent is introduced to the column to wash soluble materials from the column, push reagents and/or activators through the column, or both. The steps (1)-(4) are depicted below:

Oligo Synthesis Cycle--Step 1

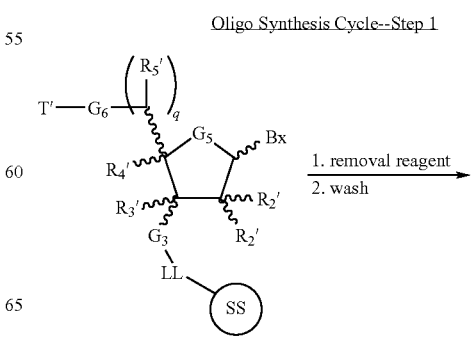

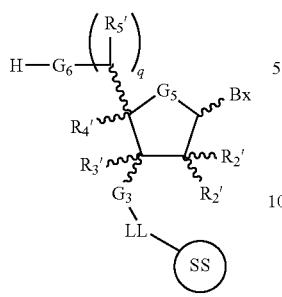

In general, T' is selected to be removable under conditions orthogonal to those used to cleave the oligonucleotide from the solid support medium at the end of synthesis, as well as those used to remove other protecting groups used during synthesis. An art-recognized protecting group for oligonucleotide synthesis is DMT (4,4'-dimethoxytrityl). The DMT group is especially useful as it is removable under weakly acid conditions. Thus, an acceptable removal reagent is 3% DCA in a suitable solvent, such as acetonitrile. The wash solvent, if used, may conveniently be acetonitrile.

The solid support medium may be controlled pore glass or a polymeric bead support medium. Some polymeric supports are disclosed in the following patents: U.S. Pat. No. 6,016,895; U.S. Pat. No. 6,043,353; U.S. Pat. No. 5,391,667 and U.S. Pat. No. 6,300,486, each of which is specifically incorporated herein by reference.

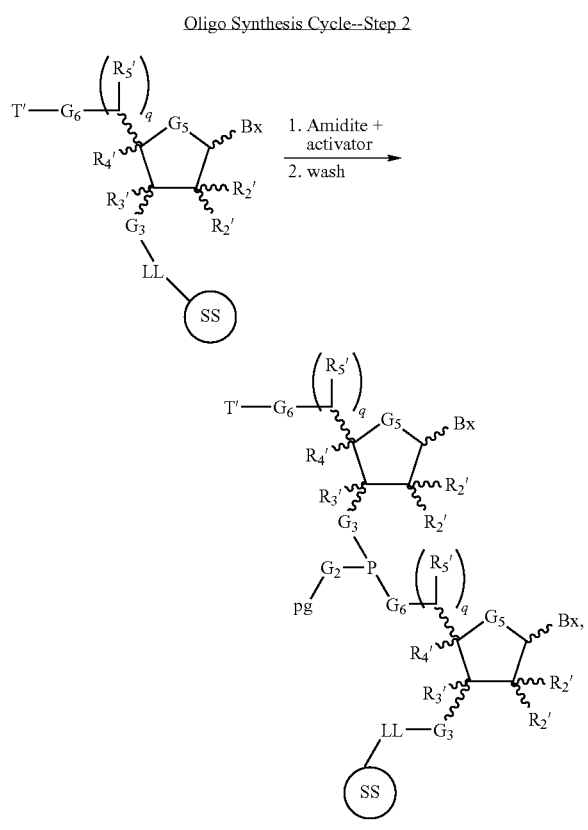

wherein pg is a phosphorus protecting group, such as a cyanoethyl group. See, Köster et al., supra, for information on manufacturing of the amidite:

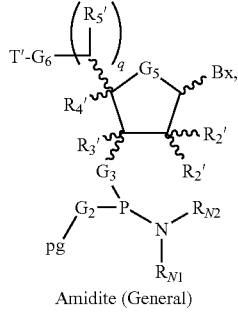

Amidite (General)

wherein $NR_{N1}R_{N2}$ is an amine leaving group, such as diisopropyl amino, and for teaching of suitable activator (e.g. tetrazole). Other suitable amidites, and methods of manufacturing amidites, are set forth in the following patents: U.S. Pat. No. 6,133,438; U.S. Pat. No. 5,646,265; U.S. Pat. No. 6,124,450; U.S. Pat. No. 5,847,106; U.S. Pat. No. 6,001,982; U.S. Pat. No. 5,705,621; U.S. Pat. No. 5,955,600; U.S. Pat. No. 6,160,152; U.S. Pat. No. 6,335,439; U.S. Pat. No. 6,274,725; U.S. Pat. No. 6,329,519, each of which is specifically incorporated herein by reference, especially as they relate to manufacture of amidites. Suitable activators are set forth in the Caruther et al. patent and in the Köster et al. patent. Especially suitable activators are set forth in the following patents: U.S. Pat. No. 6,031,092 and U.S. Pat. No. 6,476,216, each of which is expressly incorporated herein by reference.

The next step of the synthesis cycle is oxidation, which indicates that the P(III) species is oxidized to a P(V) oxidation state with a suitable oxidant:

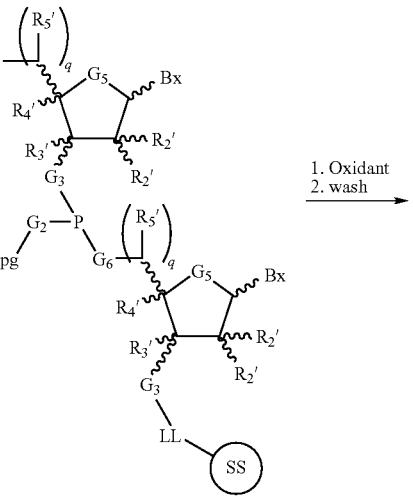

-continued

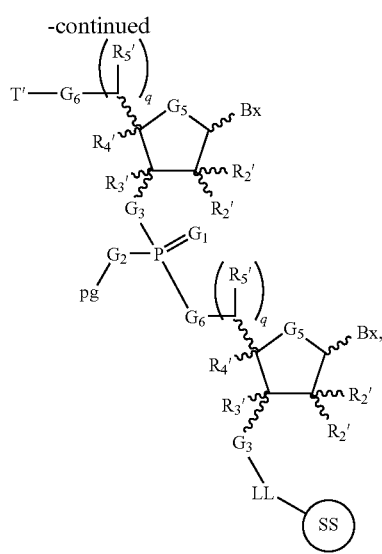

wherein $G_1$ is O or S.

The oxidant is an oxidizing agent suitable for introducing $G_1$. In the case where $G_1$ is oxygen, a suitable oxidant is set forth in the Caruthers et al. patent, above. In cases where $G_2$ is sulfur, the oxidant may also be referred to as a thiation agent or a sulfur-transfer reagent. Suitable thiation agents include the so-called Beaucage reagent, 3H-1,2-benzothiol, phenylacetyl disulfide (also referred to as PADS; see, for example the patents: U.S. Pat. Nos. 6,114,519 and 6,242,591, each of which is incorporated herein by reference) and thiouram disulfides (e.g. N,N,N',N'-tetramethylthiouram disulfide, disclosed by U.S. Pat. No. 5,166,387). The wash may be a suitable solvent, such as acetonitrile.

The oxidation step is followed by a capping step, which although not illustrated herein, is an important step for synthesis, as it causes free 5'-OH groups, which did not undergo coupling in step 1, to be blocked from being coupled in subsequent synthetic cycles. Suitable capping reagents are set forth in Caruthers et al., Köster et al., and other patents described herein. Suitable capping reagents include a combination of acetic anhydride and N-methylimidazole.

Synthetic cycle steps (1)-(4) are repeated (if so desired) n−1 times to produce a solid support-bound oligonucleotide:

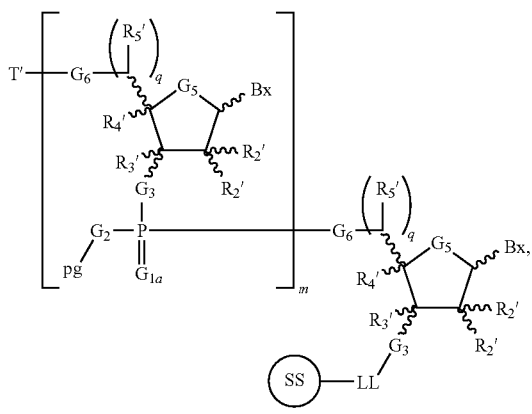

Support-Bound Oligonucleotide wherein each of the variables is as herein defined.

In general, the protecting group pg may be removed by a method as described by Caruthers et al. or Köster et al., supra. Where pg is a cyanoethyl group, the methodology of Köster et al., e.g. reaction with a basic solution, is generally suitable for removal of the phosphorus protecting group. In some cases it is desirable to avoid formation of adducts such as the N1-cyanoethyl thymidine group. In these cases, it is desirable to include in the reagent a tertiary amine, such as triethylamine (TEA) as taught in U.S. Pat. No. 6,465,628, which is expressly incorporated herein by reference. In general, where the nucleobases are protected, they are deprotected under basic conditions. The deprotected oligonucleotide is cleaved from the solid support medium to give the following 5'-protected oligonucleotide:

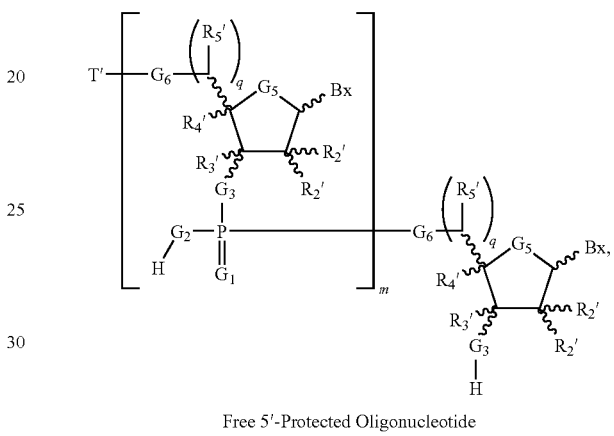

Free 5'-Protected Oligonucleotide which may then be purified by reverse phase liquid chromatography, deprotected at the 5'-end in acetic acid, desalted, lyophilized or otherwise dried, and stored in an inert atmosphere until needed. Optionally, the $G_3H$ group may be derivatized with a conjugate group. The resulting oligonucleotide may be visualized as having the formula:

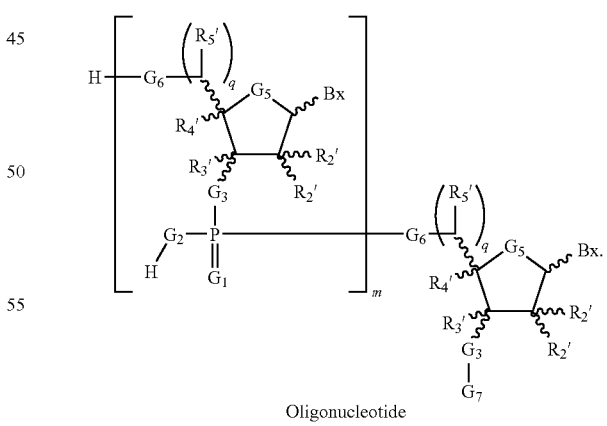

Oligonucleotide

While many improvements have been made in the quality and costs of oligonucleotide synthesis, there still remain a number of improvements to be made. For example, impurities often arise in the synthesis of oligonucleotides. While the quantities of these impurities are generally small, it is desirable, where possible, to eliminate even trace amounts of impurities, especially when the oligonucleotides are intended for pharmaceutical use, including pharmaceutical testing and therapeutic use.

Standard methods of preparing succinyl-linked solid synthesis supports require relatively complex processes that are protected as proprietary knowledge by vendors of synthetic supports. The logistics of ordering and supply dictate that synthesis supports must generally be ordered months in advance of the time when they will be used, and may sit unused for days, weeks or even months after they are synthesized but before they are used. It has been discovered that certain synthesis supports can, on standing for periods of time, degrade, e.g. by losing protecting groups from protected nucleobases. It has been shown that loss of these protecting groups can give rise to high molecular weight species, e.g. branchmers, which occur when an oligonucleotide building block couples to an exocyclic OH or $NH_2$ of a nucleobase, thereby giving rise to a branched species that can itself be extended. For example, it has been shown that the standard benzoyl protecting group for 5-methyl-2'-O-methoxyethyl cytosine (5-MeMOE C) is relatively rapidly lost from solid support medium-bound 5-MeMOE C, thereby providing an exocyclic primary nitrogen as a potential branching point during the following synthesis.

Universal building blocks and support media for oligonucleotide synthesis are disclosed in U.S. Patent Application Publication US 2004/0152905 A1, published Aug. 5, 2004, which is incorporated herein by reference in its entirety.

There is thus a need for a synthesis support suitable for oligomer synthesis that could be used in conjunction with a variety of support media. There is further a need for a synthesis support that will be traceless to the synthetic product, i.e., no atoms are imparted form the linker to the synthetic product upon cleavage therefrom. This invention is directed to these, as well as other, important ends.

SUMMARY OF THE INVENTION

Embodiments described herein provide compositions of matter suitable for use synthesis supports for oligonucleotide synthesis. Other embodiments provide linkers for use in coupling a first oligomer building block to a support medium for preparation of a synthesis support. Other embodiments provide methods of manufacturing said linkers and synthesis supports. Further embodiments provide methods of synthesis on solid supports, e.g. processes of making oligomers such as oligonucleotides (single stranded (ss) or double stranded (ds)), peptide nucleic acids (PNAs), peptides, combinatorial libraries, etc.

Synthesis supports of the present invention may be employed in processes for making oligomers, e.g. oligonucleotides, by solid phase synthetic methods. In some embodiments, the synthesis supports evince unprecedented convenience as supports for solid phase synthesis using a variety of synthetic support media. In some embodiments, the compositions of matter evince facility of manufacture, as they may be made from commonly available starting materials, in high yields and/or in exceptional purity. In some embodiments, the synthesis support provide exceptional performance as solid phase oligonucleotide synthesis supports, as their use results in fewer side-products, especially so-called branchmers, which are commonly experienced with previously known solid supports.

In some embodiments, the present invention provides compounds of formula (I) or (II):

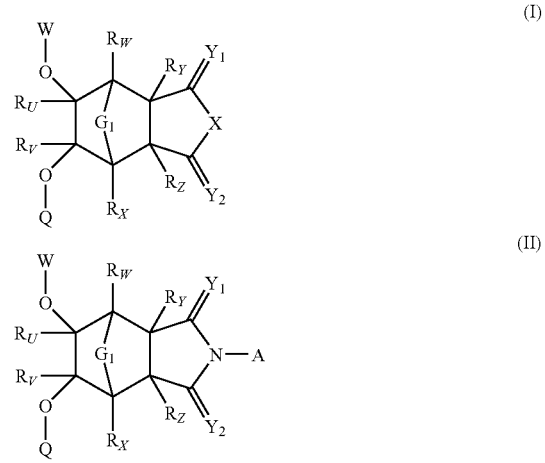

wherein:

A is independently selected from hydrogen, a blocking group, SM, L-SM, a substituted or unsubstituted aliphatic group, a substituted or unsubstituted aliphatic ether, a substituted or unsubstituted aromatic, a substituted or unsubstituted heteroaromatic; or a substituted or unsubstituted heterocyclic;

SM is a support medium;

L is a bifunctional linking moiety;

$G_1$ is independently selected from O, S, $(CR_1R_2)_h$, $NR_3$, O—(C=O), or (C=O)—O;

each of $R_1$ and $R_2$ is independently selected from hydrogen, a substituted or unsubstituted aliphatic group, a substituted or unsubstituted aromatic, a substituted or unsubstituted heteroaromatic, or a substituted or unsubstituted heterocyclic;

$R_3$ is independently selected from hydrogen, a blocking group, a substituted or unsubstituted aliphatic group, a substituted or unsubstituted aromatic, a substituted or unsubstituted heteroaromatic, or a substituted or unsubstituted heterocyclic;

each of $R_U$, $R_V$, $R_W$, $R_X$, $R_Y$, and $R_Z$ is independently selected from hydrogen, substituted or unsubstituted alkyl, substituted or unsubstituted alkenyl, or substituted or unsubstituted alkynyl;

each of Q and W is independently selected from hydrogen, a blocking group, SM, -L-SM, a substituted or unsubstituted aliphatic group, a substituted or unsubstituted aromatic, substituted or unsubstituted heteroaromatic, a substituted or unsubstituted heterocyclic, a protected or unprotected nucleosidyl moiety, a protected or unprotected nucleosidyl moiety attached through a phospholinker, or a protected or unprotected oligonucleotidyl moiety;

X is independently selected from O or S;

each of $Y_1$ and $Y_2$ is independently selected from O, S, $NR_3$, or $CR_1R_2$; and h is 1, 2, or 3.

In some embodiments, for formula (I), when one of Q or W is SM or L-SM, the other of Q or W is not SM or L-SM. In some further embodiments, for formula (II), when one of A, Q, or W is SM or L-SM, the other two of A, Q or W are not SM or L-SM.

In some embodiments, Q and W are each hydrogen and $G_1$ is O. In some further embodiments, one of Q and W is hydrogen and the other is hydrogen or a blocking group, and $G_1$, $Y_1$ and $Y_2$ are each O.

In some embodiments, Q is hydrogen, a blocking group, a protected or unprotected nucleosidyl moiety, or a protected or unprotected oligonucleotidyl moiety.

In some embodiments, the compound has the (II). In some such embodiments, A is selected from a substituted or unsubstituted aromatic, substituted or unsubstituted heteroaromatic, or a substituted or unsubstituted heterocyclic; preferably substituted or unsubstituted aromatic; preferably substituted or unsubstituted phenyl. In some such embodiments, one of Q and W is hydrogen or a blocking group and the other is selected from SM or L-SM. In some such embodiments, SM is selected from a controlled pore glass, oxalyl-controlled pore glass, silica-containing particles, polymers of polystyrene, copolymers of polystyrene, and divinylbenzene, copolymers of dimethylacrylamide and N,N-bisacryloylethylenediamine, a soluble support medium, or PEPS.

The present invention further provides compounds having the formula:

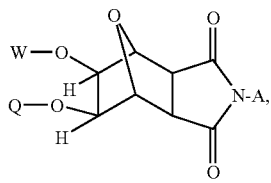

wherein the constituent variables are defined above. In some such embodiments, W is hydrogen, a blocking group, SM or L-SM; Q is hydrogen, a protected or unprotected nucleosidyl moiety, a protected or unprotected nucleosidyl moiety attached through a phospholinker, or a protected or unprotected oligonucleotidyl moiety; and A is a substituted or unsubstituted aromatic group. In some such embodiments, W and Q are each hydrogen. In further such embodiments, A is phenyl. In further such embodiments, W is SM or L-SM; Q is hydrogen, a protected or unprotected nucleosidyl moiety, a protected or unprotected nucleosidyl moiety attached through a phospholinker, or a protected or unprotected oligonucleotidyl moiety; and A is phenyl.

In some embodiments, the invention provides compounds having one of the formulas:

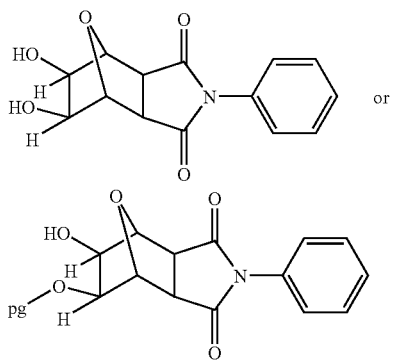

wherein pg is a 4,4'-dimethoxytriphenylmethyl group or an optionally further protected pixyl group;

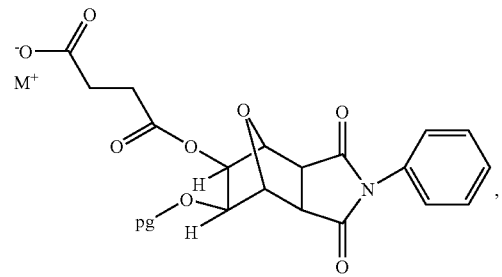

wherein $M^+$ is a triethylammonium cation and pg is a 4,4'-dimethoxytriphenylmethyl group or an optionally further substituted pixyl group;

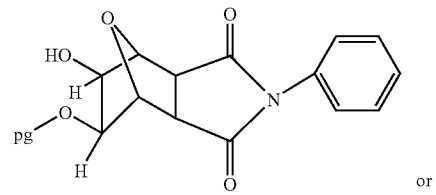

or

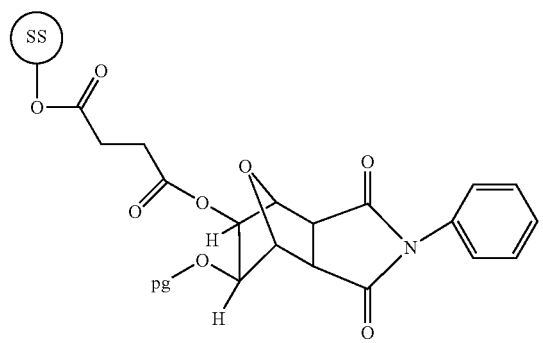

wherein SS is a solid support medium and pg is a 4,4'-dimethoxytriphenylmethyl group or an optionally further substituted pixyl group.

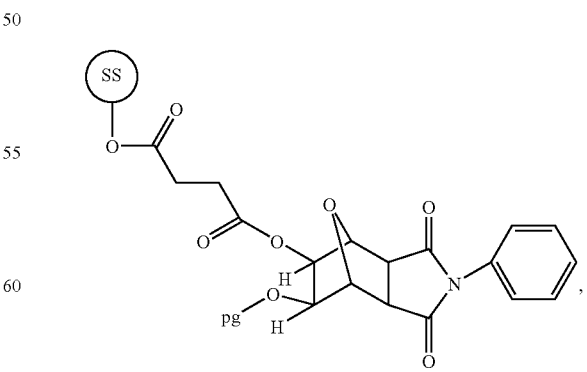

wherein SS is a solid support medium and pg is a 4,4'-dimethoxytriphenylmethyl group;

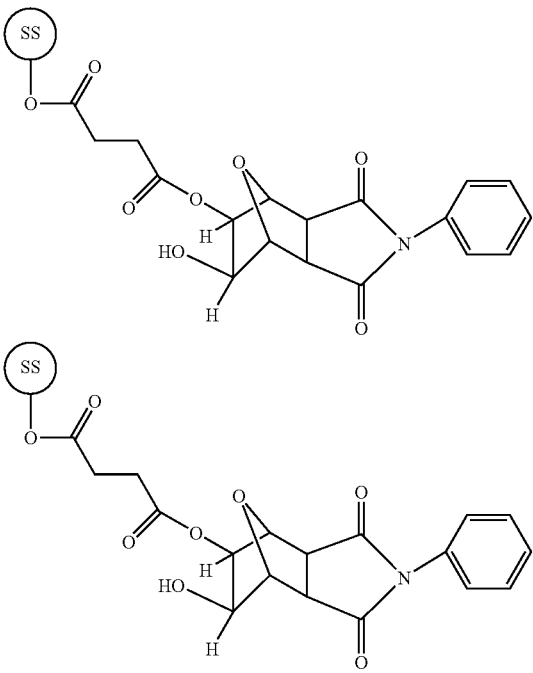

wherein SS is a solid support medium;

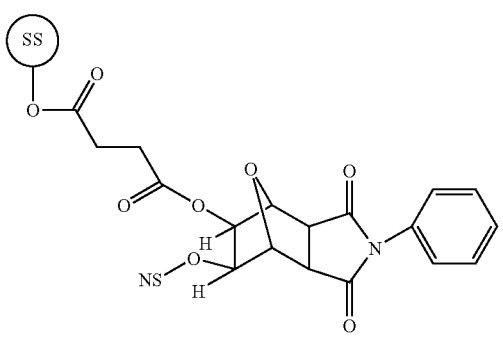

wherein NS is an optionally protected nucleoside residue.

In further embodiments, the invention provides processes for making a compound of formula (VI):

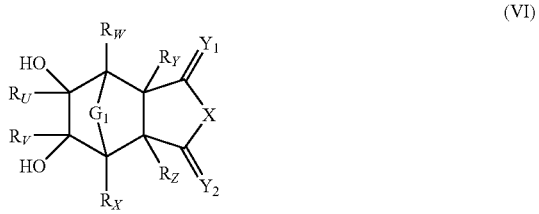

wherein:

$G_1$ is independently selected from O, S, $CR_1R_2$, or $NR_3$;

each of $R_1$ and $R_2$ is independently selected from hydrogen, a substituted or unsubstituted, saturated, partially saturated or unsaturated aliphatic group, substituted or unsubstituted aromatic, substituted or unsubstituted heteroaromatic, or substituted or unsubstituted heterocyclic;

$R_3$ is independently selected from hydrogen, a blocking group, a saturated, partially saturated or unsaturated aliphatic group, substituted or unsubstituted aromatic, substituted or unsubstituted heteroaromatic, or substituted or unsubstituted heterocyclic;

each of $R_U$, $R_V$, $R_W$, $R_X$, $R_Y$, and $R_Z$ is independently selected from hydrogen, substituted or unsubstituted alkyl, substituted or unsubstituted alkenyl, or substituted or unsubstituted alkynyl;

each of Q and W is independently selected from hydrogen, a blocking group, SM, L-SM, a substituted or unsubstituted, a saturated, or partially saturated aliphatic group, a substituted or unsubstituted aromatic, substituted or unsubstituted heteroaromatic, a substituted or unsubstituted heterocyclic, a protected or unprotected nucleosidyl moiety, a protected or unprotected nucleosidyl moiety attached through a phospholinker, or a protected or unprotected oligonucleotidyl moiety;

SM is a support medium;

L is a bifunctional linking moiety;

X is independently selected from O or S; and each of $Y_1$ and $Y_2$ is independently selected from O, S, $NR_3$, or $CR_1R_2$;

the process comprising, providing a compound of formula (III):

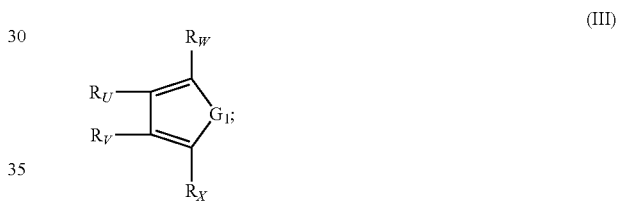

reacting said compound of formula (III) with a compound of formula (IV):

under suitable Diels-Alder conditions to produce a compound of formula (V):

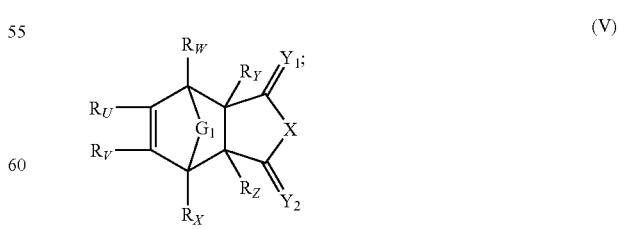

and dihydroxylating the compound of formula (V) to produce a compound of formula (VI). In some embodiments, the processes further comprise the step of protecting the hydroxyl groups of the compound of formula (VI). In further embodiments, the processes further comprise the step of selectively deprotecting one of the hydroxyl groups to yield a reactive hydroxyl; and reacting said reactive hydroxyl with a solid support or a bifunctional linker bound to a solid support to give a support bound compound of formula (I).

In further embodiments, the invention provides processes for making a compound of formula (II):

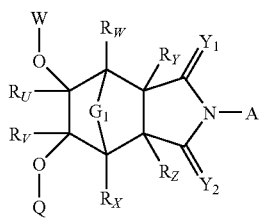
(II)

wherein:

A is independently selected from hydrogen, a blocking group, SM, L-SM, a substituted or unsubstituted, saturated, partially saturated or unsaturated aliphatic group, a substituted or unsubstituted, saturated, partially saturated or unsaturated aliphatic ether, a substituted or unsubstituted aromatic, substituted or unsubstituted heteroaromatic, or a substituted or unsubstituted heterocyclic;

$G_1$ is independently selected from O, S, $CR_1R_2$, or $NR_3$;

each of $R_1$ and $R_2$ is independently selected from hydrogen, a substituted or unsubstituted, saturated, partially saturated or unsaturated aliphatic group, substituted or unsubstituted aromatic, substituted or unsubstituted heteroaromatic, or substituted or unsubstituted heterocyclic;

$R_3$ is independently selected from hydrogen, a blocking group, a saturated, partially saturated or unsaturated aliphatic group, substituted or unsubstituted aromatic, substituted or unsubstituted heteroaromatic, or substituted or unsubstituted heterocyclic;

each of $R_U$, $R_V$, $R_W$, $R_X$, $R_Y$, and $R_Z$ is independently selected from hydrogen, substituted or unsubstituted alkyl, substituted or unsubstituted alkenyl, or substituted or unsubstituted alkynyl;

each of Q and W is independently selected from hydrogen, a blocking group, SM, L-SM, a substituted or unsubstituted, a saturated, or partially saturated aliphatic group, a substituted or unsubstituted aromatic, substituted or unsubstituted heteroaromatic, a substituted or unsubstituted heterocyclic, a protected or unprotected nucleosidyl moiety, a protected or unprotected nucleosidyl moiety attached through a phospho-linker, or a protected or unprotected oligonucleotidyl moiety;

SM is a support medium;

L is a bifunctional linking moiety; and each of $Y_1$ and $Y_2$ is independently selected from O, S, $NR_3$, or $CR_1R_2$;

the process comprising:
providing a compound of formula (VII):

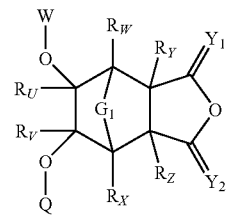
(VII)

and reacting said compound of formula (VII) with a primary amine of formula (VIII): $NH_2$-A, wherein A is independently selected from hydrogen, a blocking group, SM, L-SM, a substituted or unsubstituted, saturated, partially saturated or unsaturated aliphatic group, a substituted or unsubstituted, saturated, partially saturated or unsaturated aliphatic ether, a substituted or unsubstituted aromatic, substituted or unsubstituted heteroaromatic, or a substituted or unsubstituted heterocyclic. In some embodiments, the processes further comprise reacting the compound of formula (II) with a support medium or a bifunctional linking moiety bound to a solid medium to give a support-bound compound of formula (II).

In further embodiments, the invention provides processes for functionalizing a support medium with a first monomeric subunit, the process comprising:
providing a support-bound compound of formula (I) or (II):

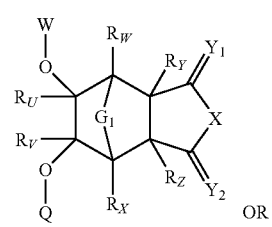
(I)

OR

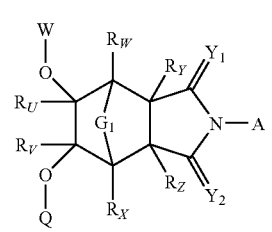
(II)

wherein:

A is independently selected from hydrogen; a blocking group; SM; L-SM; a substituted or unsubstituted aliphatic group; a substituted or unsubstituted aliphatic ether; unsaturated a substituted or unsubstituted aromatic; substituted or unsubstituted heteroaromatic; or a substituted or unsubstituted heterocyclic;

SM is a support medium;

L is a bifunctional linking moiety;

$G_1$ is independently selected from O, S, $CR_1R_2$, or $NR_3$;

each of $R_1$ and $R_2$ is independently selected from hydrogen, a substituted or unsubstituted, saturated, partially saturated or unsaturated aliphatic group, substituted or unsubstituted aromatic, substituted or unsubstituted heteroaromatic, or substituted or unsubstituted heterocyclic;

$R_3$ is independently selected from hydrogen, a blocking group, substituted or unsubstituted aliphatic group, substituted or unsubstituted aromatic, substituted or unsubstituted heteroaromatic, or substituted or unsubstituted heterocyclic;

each of $R_U$, $R_V$, $R_W$, $R_X$, $R_Y$, and $R_Z$ is independently selected from hydrogen, substituted or unsubstituted alkyl, substituted or unsubstituted alkenyl, or substituted or unsubstituted alkynyl;

one of Q or W is SM or L-SM, and the other of Q or W is a blocking group;

X is independently selected from O or S; and each of $Y_1$ and $Y_2$ is independently selected from O, S, $NR_3$, or $CR_1R_2$;

deblocking one of Q or W to give a reactive hydroxyl; and treating said reactive hydroxyl with a first monomeric subunit having a further protected hydroxyl group to form a monomer-functionalized support medium. In some embodiments, the first monomeric subunit is an activated phosphoramidite nucleoside. In some further embodiments, the processes further comprise reacting said monomer-functionalized support medium with a capping agent; and optionally treating said monomer-functionalized support medium with an oxidizing agent. In some further embodiments, the processes further comprise:

(a) deblocking said further protected hydroxyl group to give a reactive hydroxyl;

(b) treating said reactive hydroxyl with an additional monomeric subunit bearing a further protected hydroxyl to produce an extended compound;

(c) reacting the extended compound with a capping reagent;

(d) optionally contacting the product of step (b) with an oxidizing or sulfurizing agent;

optionally repeating steps (a)-(d) one or more times to form an oligomeric compound. In some other embodiments, the processes further comprise:

(a) deblocking said further protected hydroxyl group to give a reactive hydroxyl;

(b) treating said reactive hydroxyl with an additional monomeric subunit bearing a further protected hydroxyl to produce an extended compound;

(c) reacting the extended compound with a capping reagent; and optionally repeating steps (a)-(c) one or more times to form an oligomeric compound. In some such embodiments, the processes further comprise contacting the oligomeric compound with an oxidizing or sulfurizing agent. In some embodiments, the contacting with said oxidizing or sulfurizing agent cleaves said oligomeric compound from the support medium, preferably from the linker attached to the support medium. In some embodiments of the forgoing processes, the oligomeric compound possesses a terminal hydroxyl. In some such embodiments, the terminal hydroxyl is attached to a 2' or 3'-position of a nucleoside located at the 3'-terminus of said oligomeric compound. In some embodiments, the processes further comprise a step of treating said oligomeric compound with a reagent effective to cleave said oligomeric compound from said support medium, preferably from the linker attached to the support medium. In some such embodiments, the treating of the oligomeric compound with a reagent effective to cleave the oligomeric compound removes protecting groups present on the oligomeric compound. In some embodiments, the cleaved oligomeric compound has a terminal hydroxyl group at the site of cleavage. In some embodiments, the terminal hydroxyl group is attached to a 2'- or 3'-position of a nucleoside that is located at the 3'-terminus of said oligomeric compound.

In some embodiments, the treating of said reactive hydroxyl group with a further monomeric subunit is performed in the presence of an activating agent.

In some embodiments of the foregoing processes, the oligomeric compound is an oligonucleotide, modified oligonucleotide, oligonucleotide analog, oligonucleoside, oligonucleotide mimetic, hemimer, gapmer or chimera. In some embodiments, the oligomeric compound is an oligonucleotide.

In some embodiments of the above compounds and processes, the blocking group is selected from 4,4'-dimethoxytrityl, monomethoxytrityl, 9-phenylxanthen-9-yl, 9-(p-methoxyphenyl)xanthen-9-yl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, mesyl, tosyl, 4,4',4''-tris-(benzyloxy)trityl, 4,4',4''-tris-(4,5-dichlorophthalimido)trityl, 4,4',4''tris(levulinyloxy)trityl, 3-(imidazolylmethyl)-4,4'-dimethoxytrityl, 4-decyloxytrityl, 4-hexadecyloxytrityl, 9-(4-octadecyloxyphenyl)xanthene-9-yl, 1,1-bis-(4-methoxyphenyl)-1'-pyrenylmethyl, p-phenylazophenyloxycarbonyl, 9-fluorenylmethoxycarbonyl, 2,4-dinitrophenylethoxycarbonyl, 4-(methylthiomethoxy)butyryl, 2-(methylthiomethoxymethyl)-benzoyl, 2-(isopropylthiomethoxymethyl)benzoyl, 2-(2,4-dinitrobenzenesulphenyloxymethyl)benzoyl, levulinyl, trimethylsilyl, triethylsilyl, t-butyldimethylsilyl, t-butyldiphenylsilyl, triphenylsilyl, benzoylformyl, acetyl, chloroacetyl, dichloroacetyl, trichloroacetyl, trifluoroacetyl, pivaloyl, benzoyl, p-phenylbenzoyl, or acetoacetyl.

In some embodiments of the above compounds and processes, one of Q and W is $(C=O)-(CH_2)_n-(C=O)O^-$, wherein n is an integer from 1-20, preferably 2, and the other is a blocking group. In some such embodiments, one of Q and W is hydrogen or a blocking group and the other is selected from SM or L-SM.

In some embodiments of the above processes and compounds, the support medium is selected from a controlled pore glass, oxalyl-controlled pore glass, silica-containing particles, polymers of polystyrene, copolymers of polystyrene, and divinylbenzene, copolymers of dimethylacrylamide and N,N-bisacryloylethylenediamine, a soluble support medium, or PEPS. In some such embodiments, the support medium is controlled pore glass, polymers of polystyrene or copolymers of polystyrene.

In some embodiments, the invention provides compounds of the formula XI:

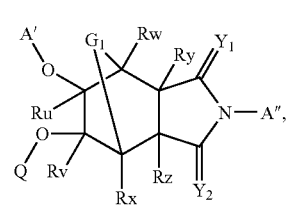

XI wherein each of A' and A'' is H, a blocking group, or a protecting group or one of A' and A'' is SM or L-SM, wherein SM is a support medium, and L is a linking moiety, the other of A' and A" being H, a blocking group or a substituent; each of Ru, Rv, Rw, Rx, Ry and Rz is H, alkyl, substituted alkyl, alkenyl, substituted alkenyl, alkynyl or substituted alkenyl; $Y_1$ and $Y_2$ are each independently of one another O, S, $NR_1CH_2$ or $CR_1R_2$, wherein $R_1$ is H, alkyl, substituted alkyl, alkenyl, substituted alkenyl, alkynyl or substituted alkenyl; $G_1$ is O, S or NR', wherein $R^1$ is H, a substituent or a blocking group; Q is H, a nucleosidyl moiety, a protected nucleosidyl moiety, a nucleosidyl moiety linked through a phosphorus linker (e.g. phosphitidyl triester, phosphodiester, phosphorothioate diester, or phosphotriester moiety), a protected oligonucleotidyl or an oligonucleotidyl moiety, or Q is T, wherein T is a protecting group.

Compounds of formula (XI) can be manufactured by reacting a compound of formula XII with a compound of formula XIII:

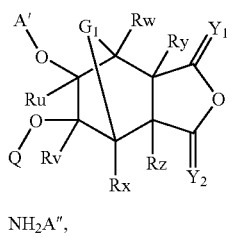

XII $NH_2A''$,

XIII wherein each of the variables is described above.

Compounds of formula XII can be synthesized by Diels-Alder reaction from dienophile XIV and diene XV:

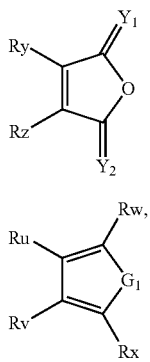

XIV

XV which together form intermediate A:

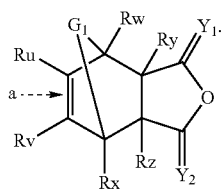

A

In each of XIV, XV and A, the variables are as described above.

Addition of hydroxyl groups across the double bond a results in intermediate B:

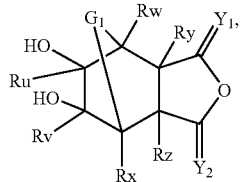

B which may be derivatized to form a compound of formula XII, above, as explained in more detail below. Of course, in formula B, the variables are as described above.

Compounds of the present invention provide facile linking of nascent chemical moieties, such as nucleosides, nucleotides, other oligomers and combinatorial chemicals, to a support medium such as a solid or semi-soluble support. Thus it is unnecessary to have a different species of linking moiety for commonly used nucleoside amidites, such as protected dA amidite, protected dG amidite, T amidite, protected dC amidite, etc. protected 5-methyl dC, protected 2'-O-methoxyethyl A amidite, protected 2'-O-methoxyethyl G amidite, protected 2'-O-methoxyethyl T amidite, protected 2'-O-methoxyethyl C amidite, protected 2'-O-methoxyethyl 5-methyl C amidite, protected 5-propynyl dC amidite, protected 5-propynyl dU amidite, (wherein, in each case, "protected" refers to protection of exocyclic amine with, e.g. isobutyryl, benzoyl), etc.

Other aspects and advantages of the invention will become apparent to the person skilled in the art upon consideration of the specification and claims.

DETAILED DESCRIPTION OF THE INVENTION

In some embodiments, the present invention provides compounds of formula (I) or (II):

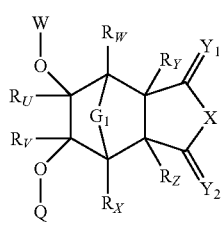

(I)

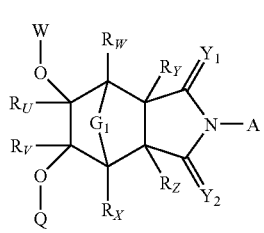

(II)

wherein:

A is independently selected from hydrogen, a blocking group, SM, L-SM, a substituted or unsubstituted aliphatic group, a substituted or unsubstituted aliphatic ether, a substituted or unsubstituted aromatic, a substituted or unsubstituted heteroaromatic; or a substituted or unsubstituted heterocyclic;

SM is a support medium;

L is a bifunctional linking moiety;

G₁ is independently selected from O, S, $(CR_1R_2)_h$, $NR_3$, O—(C=O), or (C=O)—O;

each of $R_1$ and $R_2$ is independently selected from hydrogen, a substituted or unsubstituted aliphatic group, a substituted or unsubstituted aromatic, a substituted or unsubstituted heteroaromatic, or a substituted or unsubstituted heterocyclic;

$R_3$ is independently selected from hydrogen, a blocking group, a substituted or unsubstituted aliphatic group, a substituted or unsubstituted aromatic, a substituted or unsubstituted heteroaromatic, or a substituted or unsubstituted heterocyclic;

each of $R_U$, $R_V$, $R_W$, $R_X$, $R_Y$, and $R_Z$ is independently selected from hydrogen, substituted or unsubstituted alkyl, substituted or unsubstituted alkenyl, or substituted or unsubstituted alkynyl;

each of Q and W is independently selected from hydrogen, a blocking group, SM, L-SM, a substituted or unsubstituted aliphatic group, a substituted or unsubstituted aromatic, substituted or unsubstituted heteroaromatic, a substituted or unsubstituted heterocyclic, a protected or unprotected nucleosidyl moiety, a protected or unprotected nucleosidyl moiety attached through a phospholinker, or a protected or unprotected oligonucleotidyl moiety;

X is independently selected from O or S;

each of $Y_1$ and $Y_2$ is independently selected from O, S, $NR_3$, or $CR_1R_2$; and h is 1, 2, or 3.

In some embodiments, for formula (I), when one of Q or W is SM or L-SM, the other of Q or W is not SM or L-SM. In some further embodiments, for formula (II), when one of A, Q, or W is SM or L-SM, the other two of A, Q or W are not SM or L-SM.

In some embodiments, Q and W are each hydrogen and $G_1$ is O. In some further embodiments, one of Q and W is hydrogen and the other is hydrogen or a blocking group, and $G_1$, $Y_1$ and $Y_2$ are each O.

In some embodiments, Q is hydrogen, a blocking group, a protected or unprotected nucleosidyl moiety, or a protected or unprotected oligonucleotidyl moiety.

In some embodiments, the compound has the (II). In some such embodiments, A is selected from a substituted or unsubstituted aromatic, substituted or unsubstituted heteroaromatic, or a substituted or unsubstituted heterocyclic; preferably substituted or unsubstituted aromatic; preferably substituted or unsubstituted phenyl. In some such embodiments, one of Q and W is hydrogen or a blocking group and the other is selected from SM or L-SM. In some such embodiments, SM is selected from a controlled pore glass, oxalyl-controlled pore glass, silica-containing particles, polymers of polystyrene, copolymers of polystyrene, and divinylbenzene, copolymers of dimethylacrylamide and N,N-bisacryloylethylenediamine, a soluble support medium, or PEPS.

The present invention further provides compounds having the formula:

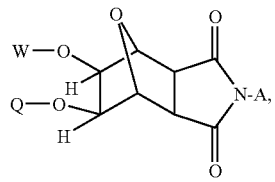

wherein the constituent variables are defined above. In some such embodiments, W is hydrogen, a blocking group, SM or L-SM; Q is hydrogen, a protected or unprotected nucleosidyl moiety, a protected or unprotected nucleosidyl moiety attached through a phospholinker, or a protected or unprotected oligonucleotidyl moiety; and A is a substituted or unsubstituted aromatic group. In some such embodiments, W and Q are each hydrogen. In further such embodiments, A is phenyl. In further such embodiments, W is SM or L-SM; Q is hydrogen, a protected or unprotected nucleosidyl moiety, a protected or unprotected nucleosidyl moiety attached through a phospholinker, or a protected or unprotected oligonucleotidyl moiety; and A is phenyl.

In some embodiments, the invention provides compounds having one of the formulas:

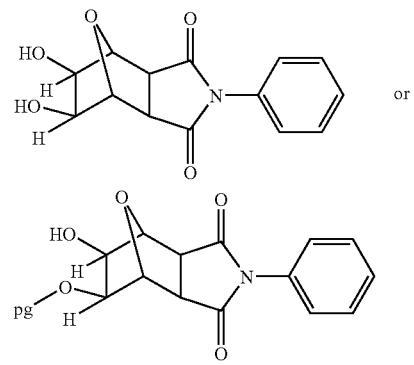

wherein pg is a 4,4'-dimethoxytriphenylmethyl group or an optionally further protected pixyl group;

or

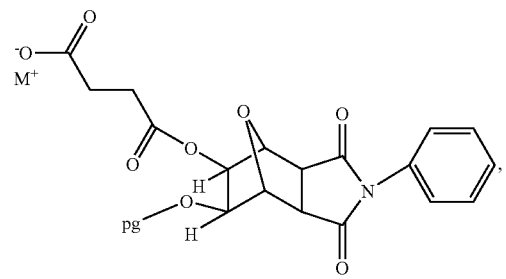

wherein $M^+$ is a triethylammonium cation and pg is a 4,4'-dimethoxytriphenylmethyl group or an optionally further substituted pixyl group;

or

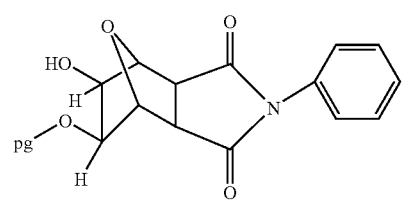

or

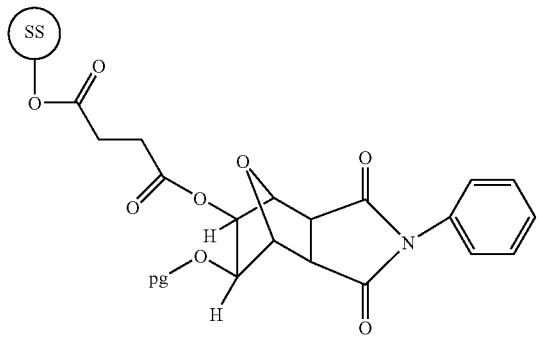

wherein SS is a solid support medium and pg is a 4,4'-dimethoxytriphenylmethyl group or an optionally further substituted pixyl group.

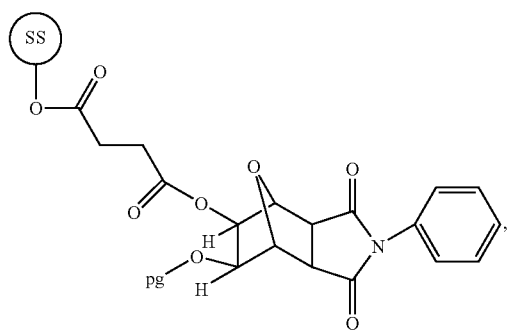

wherein SS is a solid support medium and pg is a 4,4'-dimethoxytriphenylmethyl group;

or

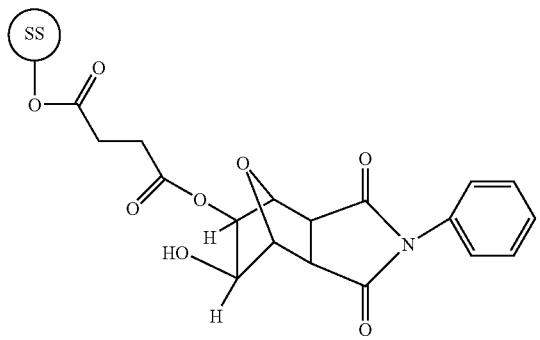

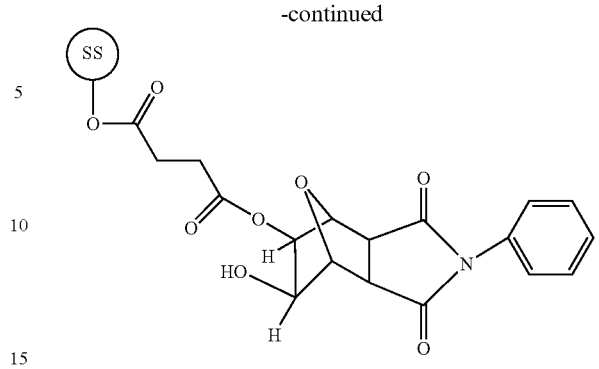

wherein SS is a solid support medium;
or

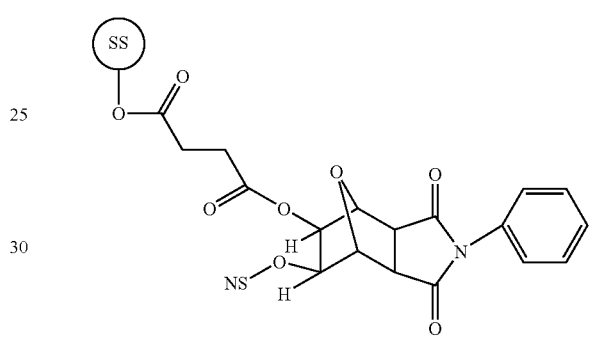

wherein NS is an optionally protected nucleoside residue.

In further embodiments, the invention provides processes for making a compound of formula (VI):

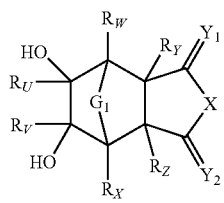

(VI)

wherein:

$G_1$ is independently selected from O, S, $CR_1R_2$, or $NR_3$;

each of $R_1$ and $R_2$ is independently selected from hydrogen, a substituted or unsubstituted, saturated, partially saturated or unsaturated aliphatic group, substituted or unsubstituted aromatic, substituted or unsubstituted heteroaromatic, or substituted or unsubstituted heterocyclic;

$R_3$ is independently selected from hydrogen, a blocking group, a saturated, partially saturated or unsaturated aliphatic group, substituted or unsubstituted aromatic, substituted or unsubstituted heteroaromatic, or substituted or unsubstituted heterocyclic;

each of $R_U$, $R_V$, $R_W$, $R_X$, $R_Y$, and $R_Z$ is independently selected from hydrogen, substituted or unsubstituted alkyl, substituted or unsubstituted alkenyl, or substituted or unsubstituted alkynyl;

each of Q and W is independently selected from hydrogen, a blocking group, SM, L-SM, a substituted or unsubstituted, a saturated, or partially saturated aliphatic group, a substituted or unsubstituted aromatic, substituted or unsubstituted heteroaromatic, a substituted or unsubstituted heterocyclic, a protected or unprotected nucleosidyl moiety, a protected or unprotected nucleosidyl moiety attached through a phospholinker, or a protected or unprotected oligonucleotidyl moiety;

SM is a support medium;

L is a bifunctional linking moiety;

X is independently selected from O or S; and each of $Y_1$ and $Y_2$ is independently selected from O, S, $NR_3$, or $CR_1R_2$;

the process comprising, providing a compound of formula (III):

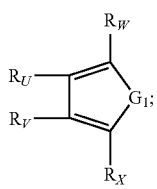

(III)

reacting said compound of formula (III) with a compound of formula (IV):

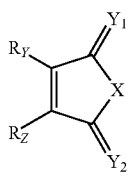

(IV)

under suitable Diels-Alder conditions to produce a compound of formula (V):

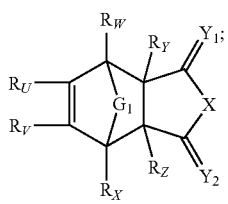

(V)

and dihydroxylating the compound of formula (V) to produce a compound of formula (VI). In some embodiments, the processes further comprise the step of protecting the hydroxyl groups of the compound of formula (VI). In further embodiments, the processes further comprise the step of selectively deprotecting one of the hydroxyl groups to yield a reactive hydroxyl; and reacting said reactive hydroxyl with a solid support or a bifunctional linker bound to a solid support to give a support bound compound of formula (I).

In further embodiments, the invention provides processes for making a compound of formula (II):

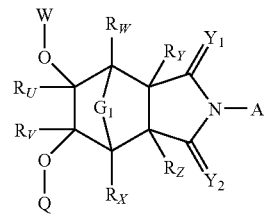

(II)

wherein:

A is independently selected from hydrogen, a blocking group, SM, -L-SM, a substituted or unsubstituted, saturated, partially saturated or unsaturated aliphatic group, a substituted or unsubstituted, saturated, partially saturated or unsaturated aliphatic ether, a substituted or unsubstituted aromatic, substituted or unsubstituted heteroaromatic, or a substituted or unsubstituted heterocyclic;

$G_1$ is independently selected from O, S, $CR_1R_2$, or $NR_3$;

each of $R_1$ and $R_2$ is independently selected from hydrogen, a substituted or unsubstituted, saturated, partially saturated or unsaturated aliphatic group, substituted or unsubstituted aromatic, substituted or unsubstituted heteroaromatic, or substituted or unsubstituted heterocyclic;

$R_3$ is independently selected from hydrogen, a blocking group, a saturated, partially saturated or unsaturated aliphatic group, substituted or unsubstituted aromatic, substituted or unsubstituted heteroaromatic, or substituted or unsubstituted heterocyclic;

each of $R_U$, $R_V$, $R_W$, $R_X$, $R_Y$, and $R_Z$ is independently selected from hydrogen, substituted or unsubstituted alkyl, substituted or unsubstituted alkenyl, or substituted or unsubstituted alkynyl;

each of Q and W is independently selected from hydrogen, a blocking group, SM, L-SM, a substituted or unsubstituted, a saturated, or partially saturated aliphatic group, a substituted or unsubstituted aromatic, substituted or unsubstituted heteroaromatic, a substituted or unsubstituted heterocyclic, a protected or unprotected nucleosidyl moiety, a protected or unprotected nucleosidyl moiety attached through a phospholinker, or a protected or unprotected oligonucleotidyl moiety;

SM is a support medium;

L is a bifunctional linking moiety; and each of $Y_1$ and $Y_2$ is independently selected from O, S, $NR_3$, or $CR_1R_2$;

the process comprising:

providing a compound of formula (VII):

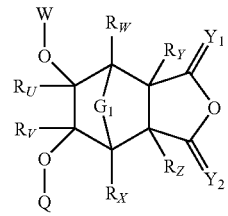

(VII)

and reacting said compound of formula (VII) with a primary amine of formula (VIII): $NH_2$-A, wherein A is independently selected from hydrogen, a blocking group, SM, L-SM, a substituted or unsubstituted, saturated, partially saturated or unsaturated aliphatic group, a substituted or unsubstituted, saturated, partially saturated or unsaturated aliphatic ether, a substituted or unsubstituted aromatic, substituted or unsubstituted heteroaromatic, or a substituted or unsubstituted heterocyclic. In some embodiments, the processes further comprise reacting the compound of formula (II) with a support medium or a bifunctional linking moiety bound to a solid medium to give a support-bound compound of formula (II).

In further embodiments, the invention provides processes for functionalizing a support medium with a first monomeric subunit, the process comprising:

providing a support-bound compound of formula (I) or (II):

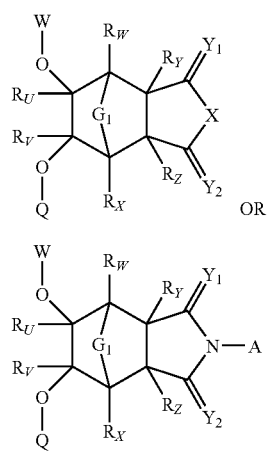

wherein:

A is independently selected from hydrogen; a blocking group; SM; L-SM; a substituted or unsubstituted aliphatic group; a substituted or unsubstituted aliphatic ether; unsaturated a substituted or unsubstituted aromatic; substituted or unsubstituted heteroaromatic; or a substituted or unsubstituted heterocyclic;

SM is a support medium;

L is a bifunctional linking moiety;

$G_1$ is independently selected from O, S, $CR_1R_2$, or $NR_3$;

each of $R_1$ and $R_2$ is independently selected from hydrogen, a substituted or unsubstituted, saturated, partially saturated or unsaturated aliphatic group, substituted or unsubstituted aromatic, substituted or unsubstituted heteroaromatic, or substituted or unsubstituted heterocyclic;

$R_3$ is independently selected from hydrogen, a blocking group, substituted or unsubstituted aliphatic group, substituted or unsubstituted aromatic, substituted or unsubstituted heteroaromatic, or substituted or unsubstituted heterocyclic;

each of $R_U$, $R_V$, $R_W$, $R_X$, $R_Y$, and $R_Z$ is independently selected from hydrogen, substituted or unsubstituted alkyl, substituted or unsubstituted alkenyl, or substituted or unsubstituted alkynyl;

one of Q or W is —SM or -L-SM, and the other of Q or W is a blocking group;

X is independently selected from O or S; and each of $Y_1$ and $Y_2$ is independently selected from O, S, $NR_3$, or $CR_1R_2$;

deblocking one of Q or W to give a reactive hydroxyl; and treating said reactive hydroxyl with a first monomeric subunit having a further protected hydroxyl group to form a monomer-functionalized support medium. In some embodiments, the first monomeric subunit is an activated phosphoramidite nucleoside. In some further embodiments, the processes further comprise reacting said monomer-functionalized support medium with a capping agent; and optionally treating said monomer-functionalized support medium with an oxidizing agent. In some further embodiments, the processes further comprise:

(a) deblocking said further protected hydroxyl group to give a reactive hydroxyl;

(b) treating said reactive hydroxyl with an additional monomeric subunit bearing a further protected hydroxyl to produce an extended compound;

(c) reacting the extended compound with a capping reagent;

(d) optionally contacting the product of step (b) with an oxidizing or sulfurizing agent;

optionally repeating steps (a)-(d) one or more times to form an oligomeric compound. In some other embodiments, the processes further comprise:

(a) deblocking said further protected hydroxyl group to give a reactive hydroxyl;

(b) treating said reactive hydroxyl with an additional monomeric subunit bearing a further protected hydroxyl to produce an extended compound;

(c) reacting the extended compound with a capping reagent; and optionally repeating steps (a)-(c) one or more times to form an oligomeric compound. In some such embodiments, the processes further comprise contacting the oligomeric compound with an oxidizing or sulfurizing agent. In some embodiments, the contacting with said oxidizing or sulfurizing agent cleaves said oligomeric compound from the support medium. In some embodiments of the forgoing processes, the oligomeric compound possesses a terminal hydroxyl. In some such embodiments, the terminal hydroxyl is attached to a 2' or 3'-position of a nucleoside located at the 3'-terminus of said oligomeric compound. In some embodiments, the processes further comprise a step of treating said oligomeric compound with a reagent effective to cleave said oligomeric compound from said support medium. In some such embodiments, the treating of the oligomeric compound with a reagent effective to cleave the oligomeric compound removes protecting groups present on the oligomeric compound. In some embodiments, the cleaved oligomeric compound has a terminal hydroxyl group at the site of cleavage. In some embodiments, the terminal hydroxyl group is attached to a 2'- or 3'-position of a nucleoside that is located at the 3'-terminus of said oligomeric compound.

In some embodiments, the treating of said reactive hydroxyl group with a further monomeric subunit is performed in the presence of an activating agent.

In some embodiments of the foregoing processes, the oligomeric compound is an oligonucleotide, modified oligonucleotide, oligonucleotide analog, oligonucleoside, oligonucleotide mimetic, hemimer, gapmer or chimera. In some embodiments, the oligomeric compound is an oligonucleotide.

In some embodiments of the above compounds and processes, the blocking group is selected from 4,4'-dimethoxytrityl, monomethoxytrityl, 9-phenylxanthen-9-yl, 9-(p-methoxyphenyl)xanthen-9-yl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, mesyl, tosyl, 4,4',4''-tris-(benzyloxy)trityl, 4,4',4''-tris-(4,5-dichlorophthalimido)trityl, 4,4',4''-tris(levulinyloxy)trityl, 3-(imidazolylmethyl)-4,4'-dimethoxytrityl, 4-decyloxytrityl, 4-hexadecyloxytrityl, 9-(4-octadecyloxyphenyl)xanthene-9-yl, 1,1-bis-(4-methoxyphenyl)-1'-pyrenylmethyl, p-phenylazophenyloxycarbonyl, 9-fluorenylmethoxycarbonyl, 2,4-dinitrophenylethoxycarbonyl, 4-(methylthiomethoxy)butyryl, 2-(methylthiomethoxymethyl)-benzoyl, 2-(isopropylthiomethoxymethyl)benzoyl, 2-(2,4-dinitrobenzenesulphenyloxymethyl)benzoyl, levulinyl, trimethylsilyl, triethylsilyl, t-butyldimethylsilyl, t-butyldiphenylsilyl, triphenylsilyl, benzoylformyl, acetyl, chloroacetyl, dichloroacetyl, trichloroacetyl, trifluoroacetyl, pivaloyl, benzoyl, p-phenylbenzoyl, or acetoacetyl.

In some embodiments of the above compounds and processes, one of Q and W is $(C=O)-(CH_2)_n-(C=O)O^-$, wherein n is an integer from 1-20, preferably 2, and the other is a blocking group. In some such embodiments, one of Q and W is hydrogen or a blocking group and the other is selected from SM or L-SM.

In some embodiments of the above processes and compounds, the support medium is selected from a controlled pore glass, oxalyl-controlled pore glass, silica-containing particles, polymers of polystyrene, copolymers of polystyrene, and divinylbenzene, copolymers of dimethylacrylamide and N,N-bisacryloylethylenediamine, a soluble support medium, or PEPS. In some such embodiments, the support medium is controlled pore glass, polymers of polystyrene or copolymers of polystyrene.

In some further embodiments, the invention provides compounds of the formula XI:

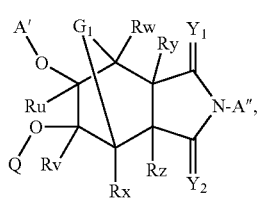

XI wherein each of A' and A'' is H or a blocking group, or one of A' and A'' is SM or L-SM, wherein SM is a support medium, and L is a linking moiety, the other of A' and A'' being H or a blocking group; each of Ru, Rv, Rw, Rx, Ry and Rz is H, alkyl, substituted alkyl, alkenyl, substituted alkenyl, alkynyl or substituted alkenyl; $Y_1$ and $Y_2$ are each independently of one another O, S, $NR_1CH_2$ or $CR_1R_2$, wherein $R_1$ is H, alkyl, substituted alkyl, alkenyl, substituted alkenyl, alkynyl or substituted alkenyl; $G_1$ is O, S or NR', wherein R' is H or a blocking group; T is H, a labile group, a nucleosidyl moiety, a protected nucleosidyl moiety, a nucleosidyl moiety linked through a phosphorus linker (e.g. phosphitidyl triester, phosphodiester, phosphorothioate diester, or phosphotriester moiety), a protected oligonucleotidyl or an oligonucleotidyl moiety.

In some preferred embodiments, compounds of formula I are support-bound linkers of formula I(a):

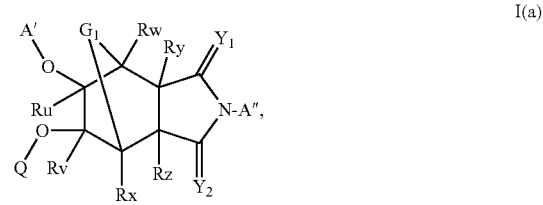

I(a)

wherein one of A' and A'' is SM or L-SM, wherein SM is a support medium, and L is a linking moiety, the other of A' and A'' being H or a blocking group; each of Ru, Rv, Rw, Rx, Ry and Rz is H, alkyl, substituted alkyl, alkenyl, substituted alkenyl, alkynyl or substituted alkenyl; $Y_1$ and $Y_2$ are each independently of one another O, S, $NR_1CH_2$ or $CR_1R_2$, wherein $R_1$ is H, alkyl, substituted alkyl, alkenyl, substituted alkenyl, alkynyl or substituted alkenyl; $G_1$ is O, S or NR', wherein $R^1$ is H or a blocking group; T is H, a labile group, a nucleosidyl moiety, a protected nucleosidyl moiety, a nucleosidyl moiety linked through a phosphorus linker (e.g. phosphitidyl triester, phosphodiester, phosphorothioate diester, or phosphotriester moiety), a protected oligonucleotidyl or an oligonucleotidyl moiety.

In some preferred embodiments of formula I(a), A' is SM or L-SM, wherein L and SM are defined above, and A'' is bg, wherein bg is a blocking group as described in more detail herein. In particularly preferred embodiments, A' is L-SM.

In other preferred embodiments of formula I(a), A' is bg and A'' is SM or L-SM, wherein bg, SM and L-SM are defined above.

In some preferred embodiments of formula I(a), T is an acid-labile group. In particularly preferred embodiments of formula I(a), T is an acid labile group selected from optionally substituted triphenylmethyl or optionally substituted pixyl groups. In such compounds, the optional substituents are on the aryl groups of the respective triphenylmethyl or pixyl groups. Particularly preferred labile groups include MMT (4-methoxytriphenylmethyl), DMT (4,4'-dimethoxytriphenylmethyl), pixyl (9-phenylxanthenyl), or substituted pixyl (9-phenylxanthenyl having one or more substituents on the aryl rings of the xanthenyl moiety; suitable substituents being halogen, $C_1$-$C_{12}$ alkyl, preferably $C_1$-$C_4$ alkyl, and $C_1$-$C_{12}$, preferably $C_1$-$C_4$ alkoxy). Selection of the appropriate labile group is possible based, inter alia upon the stability of the support medium (SM) and the linking group (L) to acid. In general, triphenylmethyl (trityl) and its derivatives (DMT and MMT being commonly referred to as "trityl groups") will require lower pH for removal than will 9-phenylxanthenyl and substituted variants of 9-phenylxanthenyl (referred to herein as "pixyl groups). The person skilled in the art should choose the labile group that is nearly fully removed under conditions that are compatible with the support medium and linker, taking into account other factors such as relative cost of labile group, cost of removal reagents, availability and disposability of reagents and solvents, etc. In general, pixyl groups are favored for their greater lability in relatively high pKa acids such as acetic acid, whereas trityl groups are favored for their relative abundance in the economy, but generally require lower pKa acids, such as chlorinated acetic acids (e.g. dichloroacetic acid (DCA)), which are less-favored due to ecological concerns, for their removal.

When T is a labile group, e.g. an acid-labile group, it may be removed to produce embodiments in which T is H. As such embodiments are generally produced in the process of manufacturing an oligonucleotide, which is a preferred use for compounds of formula I(a), such embodiments in which T is H, are also preferred.

When T is H, the free OH group formed by T and the O to which it is attached may be reacted with a species capable of linking an optionally protected nucleosidyl moiety to the O. Such species would include amidites, H-phosphonates and phosphotriesters, especially amidites and H-phosphonates.

In some preferred embodiments, $G_1$ is O, S or NH or N-bg, wherein bg is as defined above. In some preferred embodiments, $G_1$ is O, S or N-bg. In particular preferred embodiments, $G_1$ is O or S, O being particularly preferred. In other particular preferred embodiments, $G_1$ is N-bg, wherein bg is either a non-labile group or a base-labile group. Specific non-labile groups that may be mentioned in this context are $C_1$-$C_{12}$ alkyl (preferably $C_1$-$C_4$ alkyl), substituted $C_1$-$C_{12}$ (preferably $C_1$-$C_4$)alkyl, phenyl, napthyl, anthracenyl, norbonyl, $C_3$-$C_{12}$ (preferably $C_5$-$C_8$)cycloalkyl, and substituted phenyl, napthyl, anthracenyl, norbonyl, $C_3$-$C_{12}$ (preferably $C_5$-$C_8$)cycloalkyl. Suitable substituents on the alkyl, phenyl, napthyl, anthracenyl, norbornyl and cycloalkyl groups are F, Cl, Br, I, $NO_2$, dialkylamino, alkoxy, alkylthio, etc. Additional suitable substituents on phenyl, napthyl, anthracenyl, norbornyl and cycloalkyl groups include at least one $C_1$-$C_4$ alkyl group.

In some preferred embodiments, $Y_1$ and $Y_2$ are independently O, S, $CH_2$ or C(alkyl)$_2$, wherein alkyl is $C_1$-$C_{12}$, preferably $C_1$-$C_4$ alkyl. In particularly preferred embodiments, $Y_1$ and $Y_2$ are independently O, S, C(CH$_3$)$_2$, CH(CH$_3$) or $CH_2$.

In particular preferred embodiments $G_1$ is O, $Y_1$ is O and $Y_2$ is O.

In other preferred embodiments $G_1$ is S, $Y_1$ is O and $Y_2$ is O.
In other preferred embodiments $G_1$ is O, $Y_1$ is S and $Y_2$ is S.
In other preferred embodiments, $G_1$ is S, $Y_1$ is S and $Y_2$ is S.

In some preferred embodiments, each of Ru-Rz is independently selected from the group consisting of H and $C_1$-$C_{12}$ alkyl, preferably $C_1$-$C_4$ alkyl.

In some preferred embodiments, at least one of Ru-Rz is a substituent. In other preferred embodiments, at least one pair of variables, Ru and Rv, Rx and Rw, or Ry and Rz, is a substituent. In particularly preferred embodiments, at least one pair of variables, Ru and Rv, Rx and Rw, or Ry and Rz, is a substituent selected from $C_1$-$C_{12}$, even more preferably $C_1$-$C_4$ alkyl. In other preferred embodiments, each or Ru-Rz is H.

In some preferred embodiments, $G_1$, $Y_1$ and $Y_2$ are each O and Ru-Rz are each H or $C_1$-$C_4$ alkyl. In particularly preferred embodiments, $G_1$, $Y_1$ and $Y_2$ are each O and Ru-Rz are each H or methyl. In exemplary embodiments, $G_1$, $Y_1$ and $Y_2$ are each O and Ru-Rz are each H.

A suitable support medium may be any medium that facilitates separation of the compound of formula I(a) and derivatives thereof as described in detail herein, from a solution comprising reagent, reactant or wash solvent. In some cases, the support medium will be a solid phase support medium, such as a polymeric bead or controlled pore glass. In other cases, the support medium will be a semi-soluble support, which permits the compound of formula I(a) and derivatives thereof to be soluble in a solution having a certain characteristic polarity, but insoluble in solution having a different characteristic polarity. Suitable semi-soluble supports include polyethylene glycol polymer supports, which are generally soluble in less polar organic solutions, but which can be rendered insoluble upon addition of a more polar solvent, such as an alcohol (e.g. methanol or ethanol). Other suitable semi-solid supports include chitosan supports, which are similarly relatively soluble in less polar solutions. The person skilled in the art should recognize that it is necessary to choose higher molecular weight polymers (whether polyethyleneglycol (PEG), chitosan or some other semi-soluble support) to solubilize not only the compounds of formula I(a), but also derivatives thereof.

In some embodiments, there are provided compositions of formula I(b):

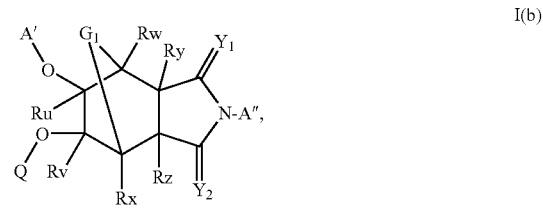

I(b)

wherein each of A' and A" is H or a blocking group, or one of A' and A" is SM or L-SM, wherein SM is a support medium, and L is a linking moiety, the other of A' and A" being H or a blocking group; each of Ru, Rv, Rw, Rx, Ry and Rz is H, alkyl, substituted alkyl, alkenyl, substituted alkenyl, alkynyl or substituted alkenyl; $Y_1$ and $Y_2$ are each independently of one another O, S, NR$_1$CH$_2$ or CR$_1$R$_2$, wherein R$_1$ is H, alkyl, substituted alkyl, alkenyl, substituted alkenyl, alkynyl or substituted alkenyl; $G_1$ is O, S or NR', wherein R' is H or a blocking group; T is H, a labile group, a nucleosidyl moiety, a protected nucleosidyl moiety, a nucleosidyl moiety linked through a phosphorus linker (e.g. phosphitidyl triester, phosphodiester, phosphorothioate diester, or phosphotriester moiety), a protected oligonucleotidyl or an oligonucleotidyl moiety.

Some preferred embodiments of the compound of formula I(b) are those in which each of A' and A" are H. Such compounds are useful as intermediates in the manufacture of support-bound linkers of formula I(a). Other preferred embodiments of the compound of formula I(b) are those in which one of A' is H and A" is a blocking group, as described above. Such compounds are useful as intermediates in the manufacture of support-bound linkers of formula I(a). Other preferred embodiments of the compound of formula I(b) are those in which A' is a blocking group, as described above, and A" is H. Such compounds are useful as intermediates in the manufacture of support-bound linkers of formula I(a).

In some embodiments, there are provided synthesis supports of the formula:

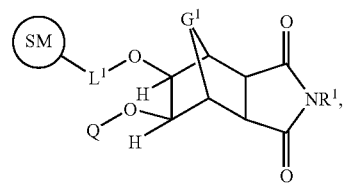

wherein SM is a support medium, e.g. a solid or a semi-soluble support medium, $L^1$ is a linker, $G_1$ is O, S, NR$^2$, wherein R$^2$ is other than H; Q is H or pg, wherein pg is a protecting group, and $R^1$ is a blocking group.

In particular embodiments, SM is a solid support, $G^1$ is O, and $R^1$ is an optionally further substituted alkyl, aryl, acyl, aralkyl, arylacyl, cycloalkyl (which may be partially dehydrogenated) heteroaryl or heteroarylacyl group. In some preferred embodiments, $R^1$ is optionally further substituted aryl, such as phenyl, naphthyl, or anthracenyl. In some preferred embodiments, $R^1$ is optionally substituted heteroaryl, such as pyridyl (e.g. pyrid-2-yl, pyrid-3-yl, pyrid-4-yl, or further substituted variants thereof), pyrimidyl (e.g. pyrimid-2-yl, pyrimid-4-yl, pyrimid-5-yl, or further substituted variants thereof), thiophenyl (e.g. thiophen-2-yl, thiophen-3-yl, or further substituted variants thereof), furanyl (furan-2-yl, furan-3-yl, or further substituted variants thereof), quinolinyl (e.g. quinolin-2-yl, quinolin-3-yl, quinolin-4-yl, quinolin-6-yl, quinolin-7-yl, or further substituted variants thereof). In some other preferred embodiments, $R^1$ is optionally substituted alkyl, such as methyl, ethyl, n-propyl, isopropyl, n-butyl, s-butyl, t-butyl, i-butyl, n-pentanyl, isooctanyl or dodecanyl, each of which is optionally substituted with one or more substituents. In some preferred embodiments, $R^1$ is optionally further substituted acyl, preferably $C_1$-$C_{12}$ acyl, and more preferably $C_1$-$C_8$ acyl, such as formyl, acetyl, pranoyl, butanoyl, octanoyl, etc.

Further substituents for groups defined above for $R^1$, when $R^1$ is alkyl, acyl, aryl, or heteroaryl, include F, Cl, Br, I, O—$C_1$-$C_{12}$ alkyl (e.g. O-methyl, O-ethyl and O-isopropyl), O—$C_1$-$C_{12}$ acyl, $NO_2$, aryl, or heteroaryl. When $R^1$ is aryl or heteroaryl, the $R^1$ substituents further include alkyl and/or acyl.

In some embodiments of the invention, there are provided synthesis supports of the formula:

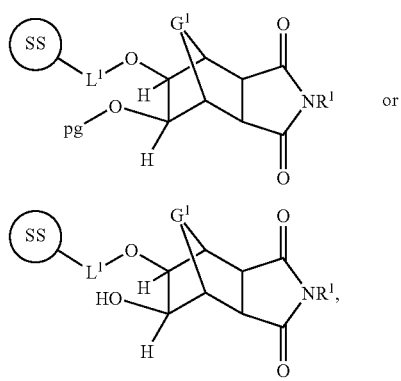

wherein SS is a solid support medium, $L^1$ is a linker, $G^1$ is O, S or $NR^2$, $R^2$ is a substituent other than H, pg is a protecting group and $R^1$ is a substituent other than H.

In some embodiments of the invention, there are provided synthesis supports of the formula:

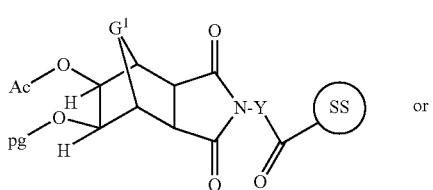

-continued

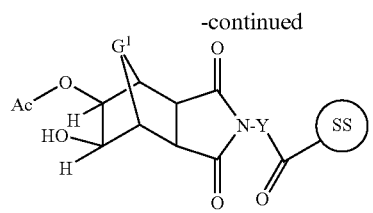

wherein SS is a solid support medium, Y is a divalent group, $G^1$ is O, S or $NR^2$, $R^2$ is a substituent other than H, and Ac and pg are mutually orthogonal protecting groups.

In some embodiments, there are provided compounds of the formula:

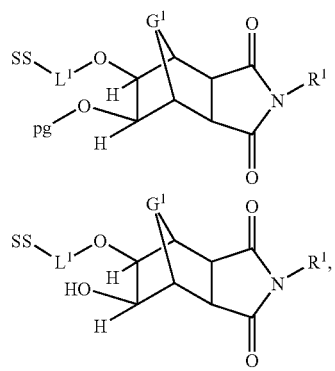

wherein SS is a solid support medium, $L^1$ is a divalent linker joining the solid support to O, pg is a protecting group, $G^1$ is O, S, $NR^2$, $R^2$ is a substituent other than H, and $R^1$ is a substituent other than H.

In other embodiments, there are provides compounds of the formula:

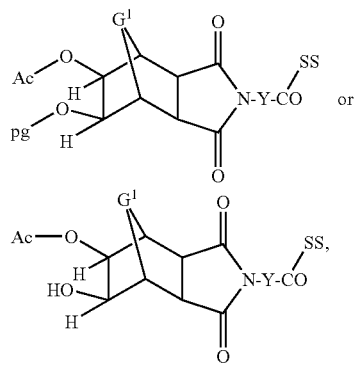

wherein SS is a solid support medium, Y is a divalent group, $G^1$ is O, S, $NR^2$, $R^2$ is a substituent other than H, Ac is an acetyl blocking group and pg is a protecting group. In some embodiments of the invention, the acetyl blocking group Ac and the protecting group pg are orthogonal to one another. In some embodiments, Ac is base-labile and pg is acid-labile.

In other embodiments, there are provided compounds of the formula:

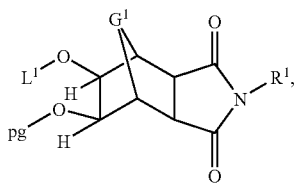

wherein the variables are defined herein, e.g. as above.

In other embodiments, there are provided compounds of the formula:

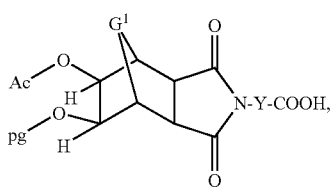

wherein the variables are defined herein, e.g. as above.

In other embodiments, there are provided compounds of the formula:

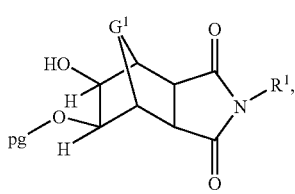

wherein the variables are defined herein, e.g. as above.

In other embodiments, there are provided compounds of the formula:

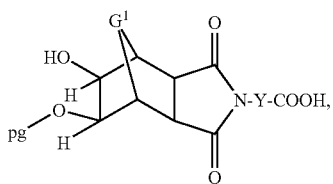

wherein the variables are defined herein, e.g. as above.

In other embodiments, there are provided compounds of the formula:

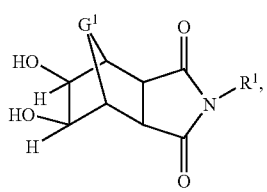

wherein the variables are defined herein, e.g. as above.

In other embodiments, there are provided compounds of the formula:

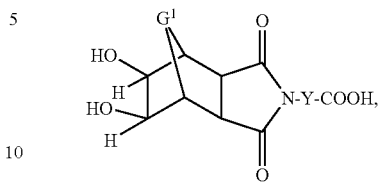

wherein the variables are defined herein, e.g. as above.

Processes of Making Inventive Compounds

Compounds of formula (XI) can be manufactured by reacting a compound of formula XII with a compound of formula XIII:

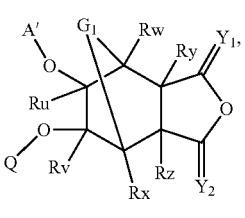

XII $NH_2A''$, XIII wherein each of the variables is described above.

Compounds of formula XII can be synthesized by Diels-Alder reaction from dienophile XIV and diene XV:

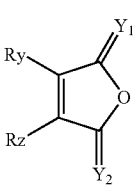

XIV

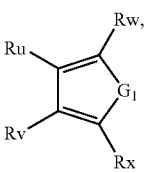

XV which together form intermediate A:

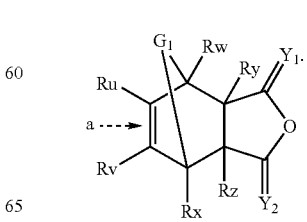

A

Addition of hydroxyl groups across the double bond a results in intermediate B:

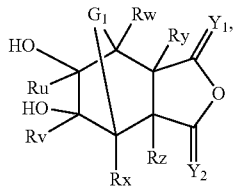

B which may be derivatized to form a compound of formula II, above.

In other embodiments, compounds of formula I can be manufactured via the following pathway:

A dienophile IVa is reacted with a diene XV to form an intermediate AA:

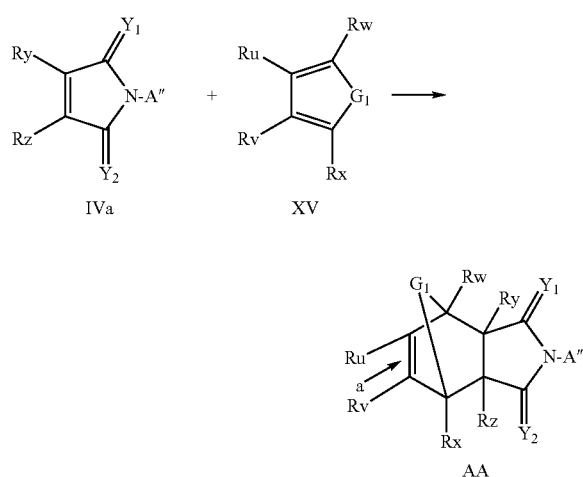

Hydroxyl groups may the be added across double bond a, to form the intermediate BB:

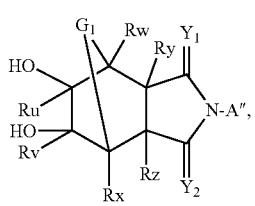

BB which may then be derivatized to form the compound of formula I, as described above.

In some embodiments of BB, AA″ is H. Such embodiments may be derivatized by reacting BB with diacid, diacid chloride, diacid anhydride, etc. to produce a compound of the formula:

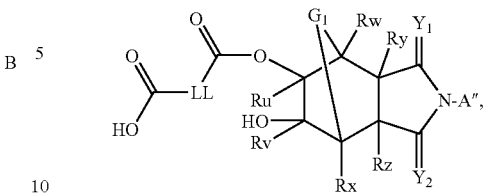

CC wherein LL is a divalent group such as alkylene, cycloalkylene, arylene, heterocyclyl, heteroarylene, and the other variables are as described above. Exemplary alkylene LL groups include $C_1$-$C_{12}$ alkylene (e.g. preferably methylene, ethylene (e.g. ethyl-1,2-ene), propylene (e.g. propyl-1,2-ene, propyl-1,3-ene), butylene, (e.g. butyl-1,4-ene, 2-methylpropyl-1,3-ene), pentylene, hexylene, heptylene, octylene, decylene, dodecylene), etc. Exemplary cycloalkylene groups include $C_3$-$C_{12}$ cycloalkylene groups, such as cyclopropylene, cyclobutylene, cyclopentanyl-1,3-ene, cyclohexyl-1,4-ene, etc. Exemplary arylene LL groups include mono- or bicyclic arylene groups having from 6 to about 14 carbon atoms, e.g. phenyl 1,2 ene, naphthyl-1,6-ene, napthyl-2,7-ene, anthracenyl, etc. Exemplary heterocyclyl groups within the scope of the invention include mono- or bicyclic aryl groups having from about 4 to about 12 carbon atoms and about 1 to about 4 hetero atoms, such as N, O and S, where the cyclic moieties may be partially dehydrogenated. Certain heteroaryl groups that may be mentioned as being within the scope of the invention include: pyrrolidinyl, piperidinyl (e.g. 2,5-piperidinyl, 3,5-piperidinyl), piperazinyl, tetrahydrothiophenyl, tetrahydrofuranyl, tetrahydro quinolinyl, tetrahydro isoquinolinyl, tetrahydroquinazolinyl, tetrahydroquinoxalinyl, etc. Exemplary heteroarylene groups include mono- or bicyclic aryl groups having from about 4 to about 12 carbon atoms and about 1 to about 4 hetero atoms, such as N, O and S. Certain heteroaryl groups that may be mentioned as being within the scope of the invention include: pyridylene (e.g. pyridyl-2,5-ene, pyridyl-3,5-ene), pyrimidinyl, thiophenyl, furanyl, quinolinyl, isoquinolinyl, quinazolinyl, quinoxalinyl, etc.

Suitable reagents for introducing the group HOCO-LL-CO above include diacids ($HO_2C$-LL-$CO_2H$). Particularly suitable diacids include malonic acid (LL is methylene), succinic acid (LL is 1,2-ethylene), glutaric acid, adipic acid, pimelic acid, and phthalic acid. Other suitable reagents for introducing HOCO-LL-CO above include diacid anhydrides. Particularly suitable diacid anhydrides include malonic anhydride, succinic anhydride, glutaric anhydride, adipic anhydride, pimelic anhydride, and phthalic anhydride. Other suitable reagents for introducing HOCO-LL-CO include diacid esters, diacid halides, etc. One especially preferred reagent for introducing HOCO-LL-CO is succinic anhydride.

The compound of formula may be linked to a support via terminal carboxylic acid of the HOCO-LL-CO group, via a reactive group on the support medium. In some embodiments, the terminal carboxylic acid forms an amide linkage with an amine reagent on the support surface. In other embodiments, the terminal carboxylic acid forms an ester with an OH group on the support medium. In some embodiments, the terminal carboxylic acid may be replaced with a terminal acid halide, acid ester, acid anhydride, etc. Specific acid halides include carboxylic chlorides, bromides and iodides. Specific esters include methyl, ethyl, and other $C_1$-$C_{10}$ alkyl esters. Specific anhydrides include formyl, acetyl, propanoyl, and other $C_1$-$C_{10}$ alkanoyl esters of the terminal carboxylic acid group of the compound of formula CC.

In particular embodiments of formula I, Ru-Rz are independently H or $C_1$-$C_4$ alkyl; $Y_1$ and $Y_2$ are independently of each other O or S; $G_1$ is O, S, N-alkyl (wherein alkyl is $C_1$-$C_{10}$ alkyl), N-aryl (wherein aryl is $C_6$-$C_{14}$ aryl) or N-cycloalkyl (wherein cycloalkyl is $C_3$-$C_{12}$ mono- or bicycloalkyl); and A" is H, $C_1$-$C_{12}$ alkyl, $C_3$-$C_{12}$ cycloalkyl, or $C_6$-$C_{14}$ mono-, bi- or tri-cycloaryl.

In particularly preferred compounds of formula I, Ru-Rz are independently H or methyl; $Y_1$ and $Y_2$ are both O; $G_1$ is O, S, N-methyl, N-ethyl, N-n-propyl, N-isopropyl, N-n-butyl, N-isobutyl, N-s-butyl or N-t-butyl, N-phenyl, N-cyclopentyl, N-cyclohexyl or N-cycloheptyl; and A" is H, $C_1$-$C_4$ alkyl, $C_5$-$C_{10}$ cycloalkyl, or phenyl.

In particularly preferred compounds of formula I, Ru-Rz are independently H or methyl, at least one being methyl; $Y_1$ and $Y_2$ are both O; $G_1$ is O, S, N-methyl, N-ethyl, N-n-propyl, N-isopropyl, N-n-butyl, N-isobutyl, N-s-butyl or N-t-butyl, N-phenyl, N-cyclopentyl, N-cyclohexyl or N-cycloheptyl; and A" is H, $C_1$-$C_4$ alkyl, $C_5$-$C_{10}$ cycloalkyl, or phenyl.

In some preferred embodiments of compounds of formula I, at least two of Ru-Rz are H, the remainder being substituents other than H. In particularly preferred embodiments at least two of Ru-Rz are H, the remainder being substituents other than H; and $Y_1$ and $Y_2$ are both O. In especially preferred embodiments, embodiments at least two of Ru-Rz are H, the remainder being substituents other than H; $Y_1$ and $Y_2$ are both and $G_1$ is O or S. In specific particularly preferred embodiments, at least two of Ru-Rz are H, the remainder being substituents other than H; $Y_1$ and $Y_2$ are both O; $G_1$ is O or S; and A" is H, $C_1$-$C_4$ alkyl, $C_5$-$C_{10}$ cycloalkyl, or phenyl. In other specific preferred embodiments, at least two of Ru-Rz are H, the remainder being substituents other than H; $Y_1$ and $Y_2$ are both O; $G_1$ is O; and A" is H, $C_1$-$C_4$ alkyl, $C_5$-$C_{10}$ cycloalkyl, or phenyl.

In some preferred embodiments of compounds of formula I, each of Ru-Rz is H. In particularly preferred embodiments each of Ru-Rz is H; and $Y_1$ and $Y_2$ are both O. In especially preferred embodiments, each of Ru-Rz is H; $Y_1$ and $Y_2$ are both O and $G_1$ is O or S. In specific particularly preferred embodiments, each of Ru-Rz is H; $Y_1$ and $Y_2$ are both O; $G_1$ is O or S; and A" is H, $C_1$-$C_4$ alkyl, $C_5$-$C_{10}$ cycloalkyl, or phenyl. In other specific preferred embodiments, each of Ru-Rz is H; $Y_1$ and $Y_2$ are both O; $G_1$ is O; and A" is H, $C_1$-$C_4$ alkyl, $C_5$-$C_{10}$ cycloalkyl, or phenyl.

In some embodiments of the invention, $Y_1$ and $Y_2$ are S.

In some embodiments of the invention, $G_1$ is O or S.

In some embodiments of the invention, A" is H, $C_1$-$C_4$ alkyl or phenyl.

As used herein, the term oligonucleotide (or adjectival variants such as oligonucleotidyl) has the meaning of an oligomer having m subunits embraced within the brackets [ ] of the formula:

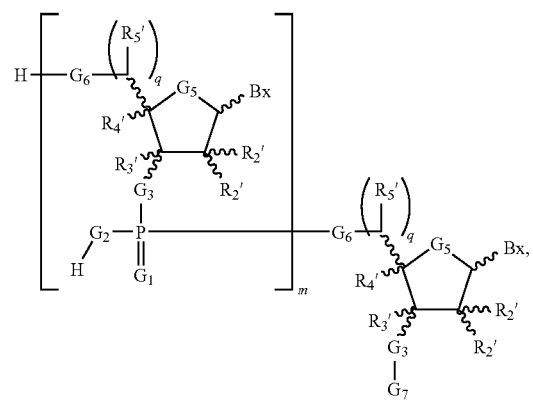

wherein the other variables are defined above, and are described in more detail hereinafter. It is to be understood that, although the oligonucleotide to be made is depicted in a single stranded conformation, it is common for oligonucleotides to be used in a double stranded conformation. For example, in the antisense method referred-to commonly as siRNA, two strands of RNA or RNA-like oligonucleotide are prepared and annealed together, often with a two-nucleotide overlap at the ends. Thus, the present invention contemplates manufacture of both single- and double-stranded oligonucleotides.

In some embodiments, the present invention provides compounds having the formula Ia:

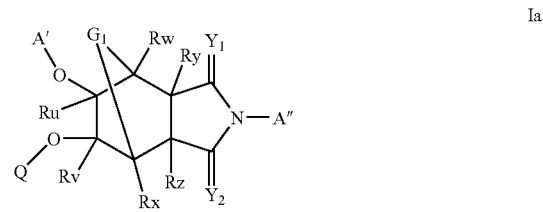

wherein each of A' and A" is H, a blocking group or a substituent, or one of A' and A" is SM or L-SM, wherein SM is a support medium, and L is a linking moiety, the other of A' and A" being H, a blocking group or a substituent; each of Ru, Rv, Rw, Rx, Ry and Rz is H, alkyl, substituted alkyl, alkenyl, substituted alkenyl, alkynyl or substituted alkenyl; $Y_1$ and $Y_2$ are each independently of one another O, S, $NR_1$ $CH_2$ or $CR_1R_2$, wherein $R_1$ is H, alkyl, substituted alkyl, alkenyl, substituted alkenyl, alkynyl or substituted alkenyl; $G_1$ is O, S or NR', wherein $R^1$ is H, a blocking group or a substituent; Q is H, a nucleosidyl moiety, a protected nucleosidyl moiety, a nucleosidyl moiety linked through a linker (e.g. phosphitidyl triester, phosphodiester, phosphorothioate diester, or phosphotriester moiety), a protected oligonucleotidyl or an oligonucleotidyl moiety, or Q is T, wherein T is a protecting group.

In some embodiments, each of $Y_1$ and $Y_2$ is O. In some further embodiments, at least one of $Y_1$ and $Y_2$ is O. In some further embodiments, A" is phenyl. In some further embodiments, A" is L-SM. In some embodiments, A' is L-SM. In some embodiments, the compound of formula Ia has the formula:

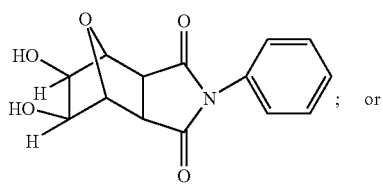

;  or

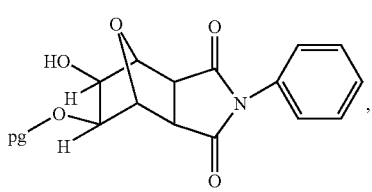

wherein pg is a 4,4'-dimethoxytriphenylmethyl group or an optionally further substituted pixyl group. In some further embodiments, the compound of formula Ia has the formula:

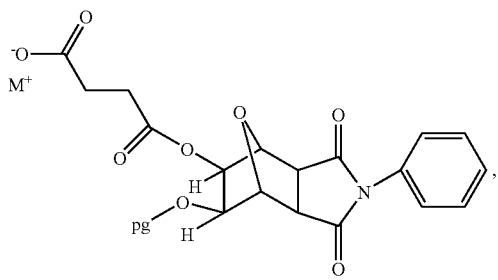

wherein M⁺ is a triethylammonium cation and pg is a 4,4'-dimethoxytriphenylmethyl group or an optionally further substituted pixyl group. In some further embodiments, the compound of formula Ia has the formula:

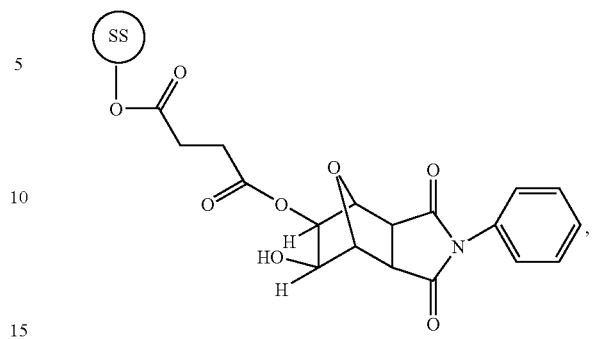

wherein SS is a solid support medium. In some further embodiments, the compound of formula Ia has the formula:

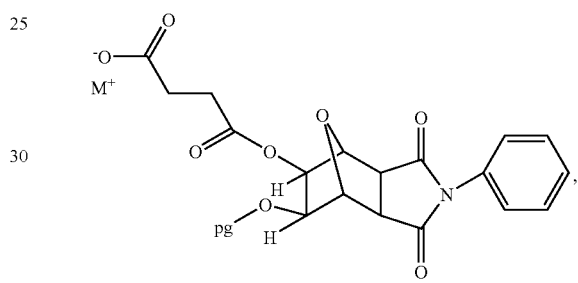

wherein M⁺ is a triethylammonium cation and pg is a 4,4'-dimethoxytriphenylmethyl group or an optionally further substituted pixyl group. In some further embodiments, the compound of formula Ia has the formula:

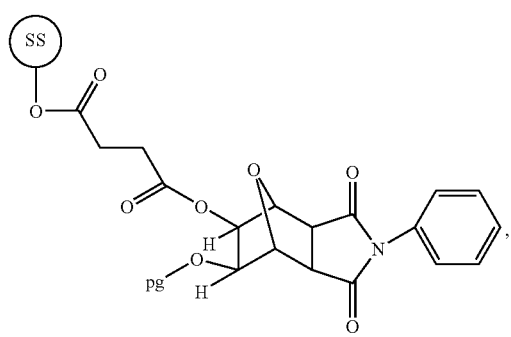

wherein SS is a solid support medium and pg is a 4,4'-dimethoxytriphenylmethyl group or an optionally further substituted pixyl group. In some further embodiments, the compound of formula Ia has the formula:

wherein NS is a residue of an optionally protected nucleoside and SS is a solid support medium.

In some further embodiments, the present invention provides processes for making a compound of formula:

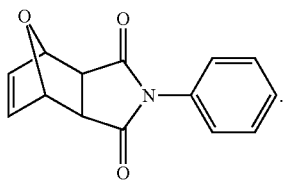

comprising reacting furan with N-phenylmaleimide to form the compound. In some further embodiments, the present invention provides processes for making a compound of formula:

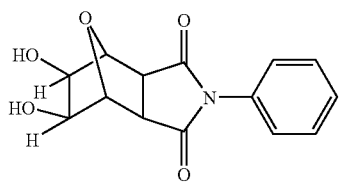

comprising the step of introducing two syn-oriented hydroxyl groups across the unsaturation in a compound of formula:

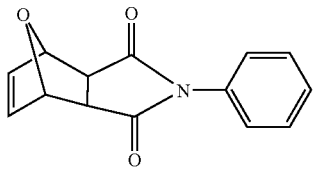

to produce the compound.

In some embodiments, the step for adding two hydroxyl groups across the unsaturation includes reaction of hydrogen peroxide with the compound.

The present invention further provides processes comprising reacting a compound of formula:

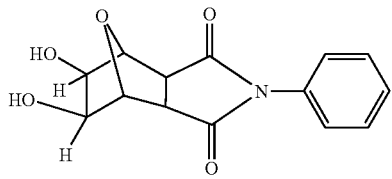

with chloro-(4,4'-dimethoxytriphenyl)methane to form a compound of formula:

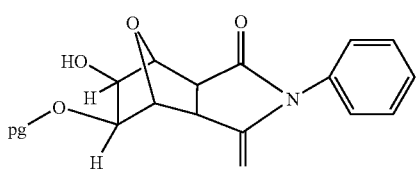

wherein pg is a 4,4'-dimethoxytriphenylmethyl group or an optionally further protected pixyl group.

In further embodiments, the present invention provides processes for making a compound of formula (XIII)

(XIII)

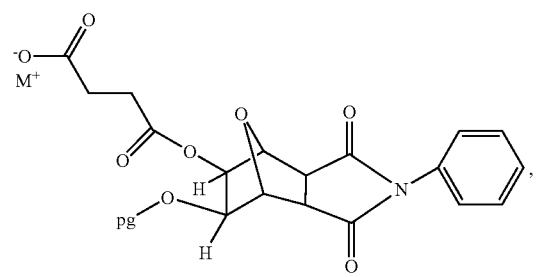

wherein $M^+$ is a triethylammonium cation and pg is a 4,4'-dimethoxytriphenylmethyl group or an optionally further substituted pixyl group; the process comprising reacting a compound of formula XII:

XII

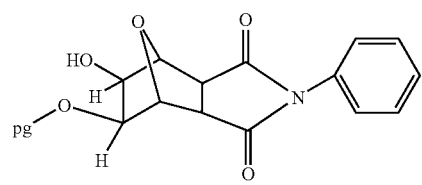

with succinic acid or succinic anhydride in the presence of triethylamine to produce the compound of formula XIII.

In some further embodiments, the present invention provides processes for making a compound of the formula XIV, the process comprising reacting a compound of formula XIII with a solid support medium having a free reactive group to form the compound of formula XIV:

III

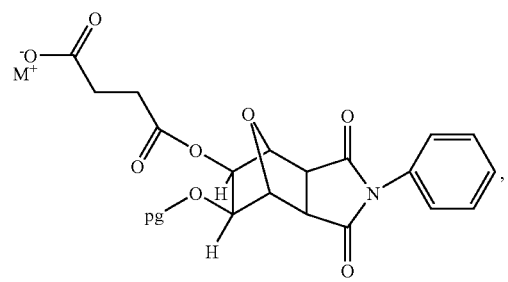

-continued

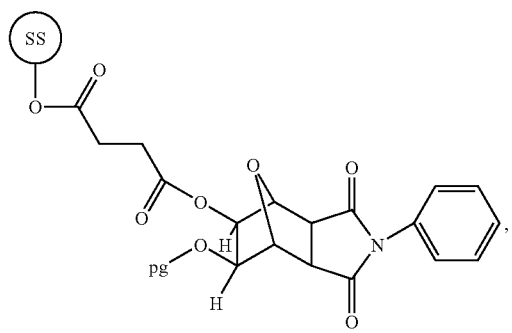

IV wherein SS is a solid support medium and pg is a 4,4'-dimethoxytriphenylmethyl group or an optionally further substituted pixyl group.

In some further embodiments, the present invention provides processes for making a compound of the formula XV, comprising reacting a compound of formula XIV with dichloroacetic acid for a time sufficient to remove the pg, thereby forming the compound of formula V:

XIV

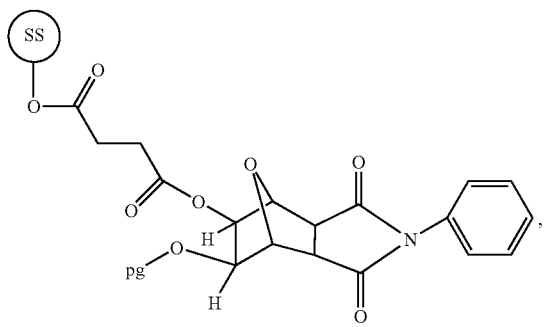

wherein SS is a solid support medium and pg is a 4,4'-dimethoxytriphenylmethyl group

XV

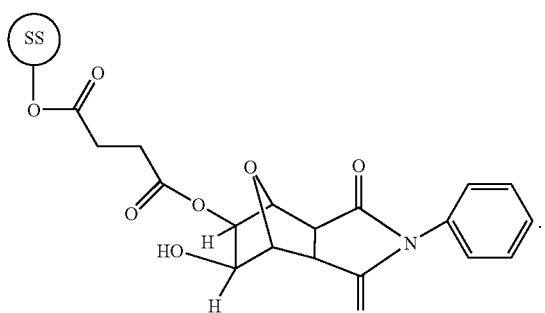

In some further embodiments, the present invention provides processes for making a compound of formula XVI, the process comprising reacting an optionally protected nucleoside amidite with a compound of formula V to form the compound of formula XVI:

XV

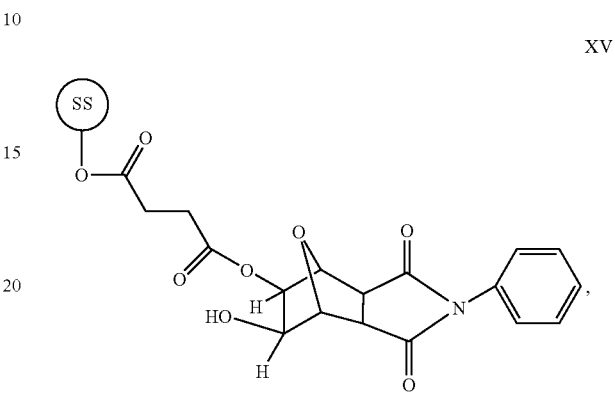

wherein SS is a solid support medium,

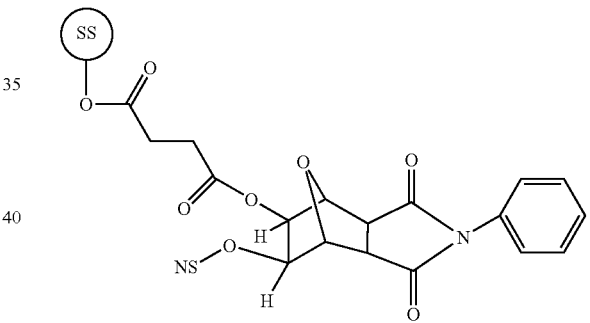

wherein NS is an optionally protected nucleoside residue.

In some further embodiments, the present invention provides processes for making a compound of formula XVII:

XVII

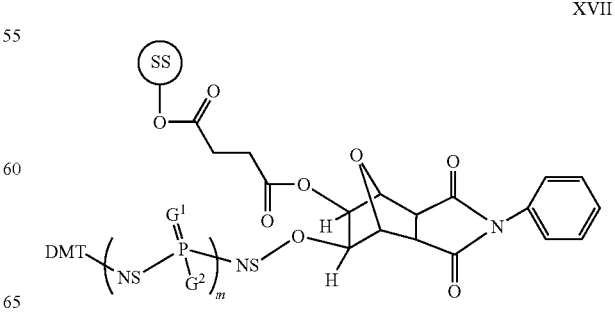

the process comprising:
providing a compound of Formula XVI:

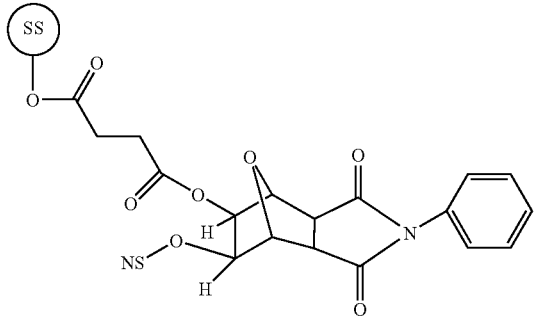

XVI wherein NS is a protected nucleoside residue;
(a) deprotecting the 5'-terminal nucleoside group of said NS to form a free 5'-terminal hydroxyl;
(b) reacting the free hydroxyl group of the 5'-terminal hydroxyl with a nucleoside amidite;
(c) oxidizing a PIII moiety to a PV species;
(d) capping unreacted 5'-terminal hydroxyl groups; and repeating steps a-d, if necessary to complete m cycles of steps a-d;
wherein each $G^1$ is independently selected from O and S each $G^2$ is OH, SH, $O^-M^+$ or $S^-M^+$, wherein each $M^+$ represents a charge equivalent of a cation, m is an integer from 2 to about 200, and DMT is a 4,4'-dimethoxytriphenylmethyl group, SS is a solid support medium, and each NS is an optionally protected nucleoside residue.

In some further embodiments, the present invention provides processes for making a compound of the formula XVIII:

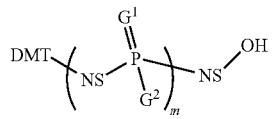

XVIII said process comprising reacting a compound of the formula XVII:

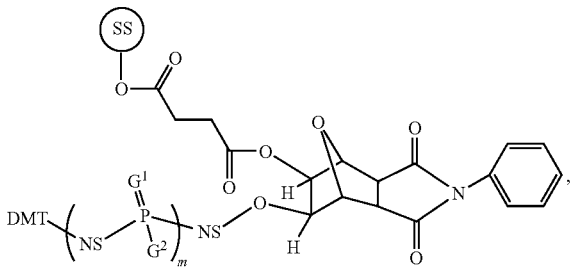

XVII wherein each $G^1$ is independently selected from O and S each $G^2$ is OH, SH, $O^-M^+$ or $S^-M^+$, wherein each $M^+$ represents a charge equivalent of a cation, m is an integer from 2 to about 200, and DMT is a 4,4'-dimethoxytriphenylmethyl group, SS is a solid support medium, and each NS is an optionally protected nucleoside residue;

with a cleaving reagent to form the compound of formula XVIII. In some embodiments, the cleavage is carried out in ammonia at a temperature in the range of about 50° C. to about 60° C. for a period of about 4-14 h.

The present invention also provides compounds of the formula:

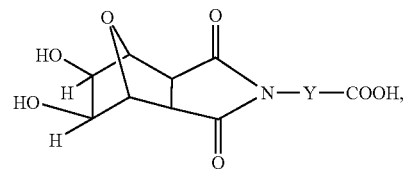

wherein Y is alkylene, cycloalkylene, arylene, heteroarylene, arylalkylene, alkarylene, or alkylenearylalkylene, and compounds of the formula:

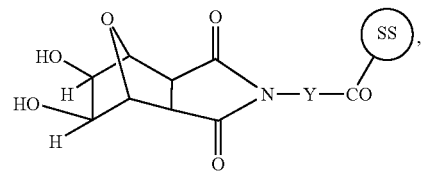

wherein Y is alkylene, cycloalkylene, arylene, heteroarylene, arylalkylene, alkarylene, or alkylenearylalkylene and SS is a solid support medium.

The invention further provides compounds of the formula:

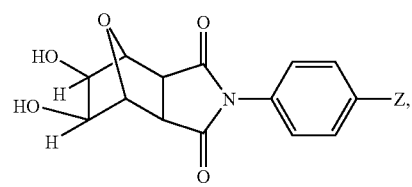

wherein Z is COOH, alk-COOH (wherein alk is a branched or unbranched alkylene) or an AR-COOH group (wherein AR is mono- or bicyclic aryl group, which may be optionally unsaturated), and compounds of the formula:

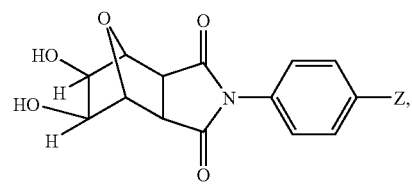

wherein Z is COOH or $CH_2COOH$; and compounds of the formula:

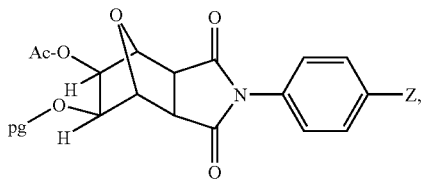

wherein Ac is an acyl, benzoyl or other base-labile protecting group and Z is COOH, alk-COOH (wherein alk is a branched or unbranched alkylene) or an AR-COOH group (wherein AR is mono- or bicyclic aryl group, which may be optionally unsaturated); and compounds of the formula:

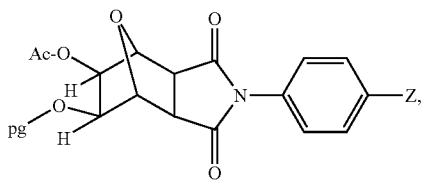

wherein Ac is C(=O)CH$_3$, pg is 4,4'-dimethoxytriphenylmethyl and Z is COOH or CH$_2$COOH; and compounds of the formula:

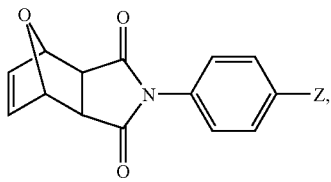

wherein Z is COOH, alk-COOH (wherein alk is a branched or unbranched alkylene) or an AR-COOH group (wherein AR is mono- or bicyclic aryl group, which may be optionally unsaturated); and compounds of the formula:

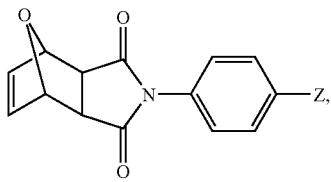

wherein Z is COOH or CH$_2$COOH; and compounds of the formula:

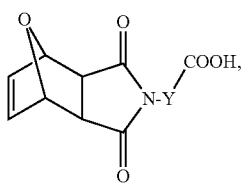

wherein Y is alkylene, cycloalkylene, arylene, heteroarylene, arylalkylene, alkarylene, or alkylenearylalkylene.

In some further embodiments, the present invention provides processes for making a target compound of the formula:

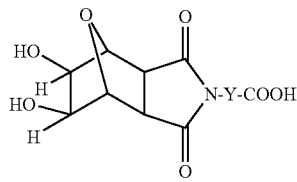

the process comprising reacting furan with maleicanhydride by a diels alder addition to form a first intermediate of the formula:

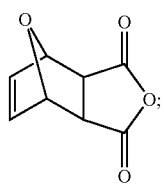

reacting the first intermediate with H$_2$O$_2$ to form a second intermediate of the formula:

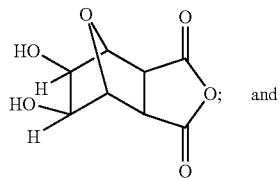 and reacting the second intermediate with a reagent of the formula:

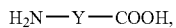

$$H_2N-Y-COOH,$$

wherein Y is alkylene, cycloalkylene, arylene, heteroarylene, arylalkylene, alkarylene, or alkylenearylalkylene, to form the target compound. In some embodiments, Y is phenylene, or Y is 1,4-phenylene, or Y is benzylene, or Y is 1,4-benzylene. In some embodiments, the target compound is of the formula:

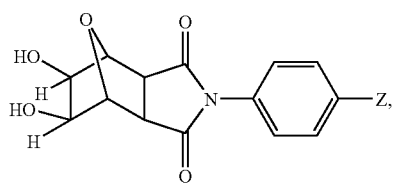

wherein Z is COOH, alk-COOH (wherein alk is a branched or unbranched alkylene) or an AR-COOH group (wherein AR is mono- or bicyclic aryl group, which may be optionally unsaturated). In some further embodiments, the target compound is of the formula:

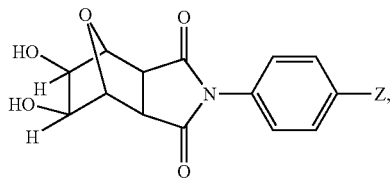

wherein Z is COOH or CH$_2$—COOH.

The present invention further provides compounds of the formula:

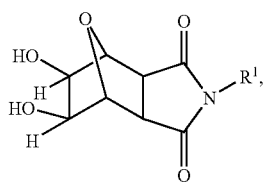

wherein R$^1$ is aryl, cycloalkyl, unsaturated cycloalkyl, alkyl, unsaturated alkyl, heterocyclyl, unsaturated heterocyclyl, heteroaryl or acyl, wherein R$^1$ is optionally substituted with one or more substituents. In some embodiments, R$^1$ is further substituted with from 1 to 5 substituents. In some embodiments, R$^1$ is aryl, which is optionally further substituted. In some further embodiments, R$^1$ is phenyl or naphthyl, which is optionally further substituted. In some further embodiments, R$^1$ is phenyl or naphthyl, which is unsubstituted or substituted with from 1 to about 5 substituents independently selected from the group consisting of F, Cl, Br, I, NO$_2$, C$_1$-C$_{12}$ alkyl and CF$_3$. In some embodiments, R$^1$ is phenyl or naphthyl, which is unsubstituted. In some embodiments, R$^1$ is heterocyclyl, and R$^1$ is optionally further substituted. In some embodiments, R$^1$ is pyridiyl, pyrimidinyl, quinolinyl, isoquinolinyl, quinazolinyl, quinoxalinyl, furanyl, thiophenyl, thiazolyl, pyrrolyl or imidazolyl and R$^1$ is optionally further substituted. In some embodiments, R$^1$ is pyridyl, furanyl or thiophenyl and R$^1$ is optionally further substituted. In some embodiments, R$^1$ is pyridiyl, furanyl, or thiophenyl, and R$^1$ is not further substituted. In some embodiments, R$^1$ is N-alkyl-morpholinyl, N-alkyl-piperidinyl or N,N'-dialkylpiperazinyl, and R$^1$ is optionally further substituted.

The present invention further provides compounds of the formula:

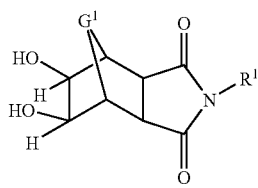

wherein G$^1$ is O, S or NR$^2$, R$^2$ is a substituent and R$^1$ is phenyl. In some embodiments, G$^1$ is O. In some embodiments, G$^1$ is S. In some embodiments, G$^1$ is NR$^2$. In some embodiments, G$^1$ is NR$^2$ and R$^2$ is selected from the group consisting of alkyl, cycloalkyl, aryl, heterocyclyl and heteroaryl, wherein R$^2$ is optionally further substituted and wherein each R$^2$ optionally contains one or more unsaturations. In some embodiments, G$^1$ is NR$^2$ and R$^2$ is selected from the group consisting of alkyl and cycloalkyl, wherein R$^2$ optionally contains one or more unsaturations. In some embodiments, G$^1$ is NR$^2$ and R$^2$ is aryl, which is optionally substituted.

The present invention further provides compounds of the formula:

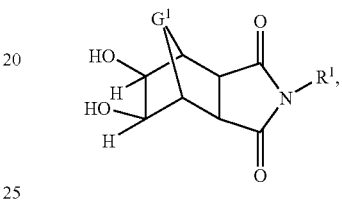

wherein G$^1$ is O, S or NR$^2$; R$^2$ is a substituent and R$^1$ is aryl, cycloalkyl, unsaturated cycloalkyl, alkyl, unsaturated alkyl, heterocyclyl, unsaturated heterocyclyl, heteroaryl or acyl, wherein R$^1$ is optionally substituted with one or more substituents. In some embodiments, R$^1$ is further substituted with from 1 to 5 substituents. In some embodiments, R$^1$ is aryl, which is optionally further substituted. In some embodiments, R$^1$ is phenyl or naphthyl, which is optionally further substituted. In some embodiments, R$^1$ is phenyl or naphthyl, which is unsubstituted or substituted with from 1 to about 5 members selected from the group consisting of F, Cl, Br, I, NO$_2$, C$_1$-C$_{12}$ alkyl and CF$_3$. In some embodiments, R$^1$ is phenyl or naphthyl, which is unsubstituted. In some embodiments, R$^1$ is heterocyclyl, and R$^1$ is optionally further substituted. In some embodiments, R$^1$ is pyridiyl, pyrimidinyl, quinolinyl, isoquinolinyl, quinazolinyl, quinoxalinyl, furanyl, thiophenyl, thiazolyl, pyrrolyl or imidazolyl and R$^1$ is optionally further substituted. In some embodiments, R$^1$ is pyridyl, furanyl or thiophenyl and R$^1$ is optionally further substituted. In some embodiments, R$^1$ is pyridiyl, furanyl, or thiophenyl, and R$^1$ is not further substituted. In some embodiments, R$^1$ is N-alkyl-morpholinyl, N-alkyl-piperidinyl or N,N'-dialkylpiperazinyl, and R$^1$ is optionally further substituted. In some embodiments, G$^1$ is O. In some embodiments, G$^1$ is S. In some embodiments, G$_1$ is NR$^2$. In some embodiments, G$^1$ is NR$^2$ and R$^2$ is selected from the group consisting of alkyl, cycloalkyl, aryl, heterocyclyl and heteroaryl, wherein R$^2$ is optionally further substituted and wherein each R$^2$ optionally contains one or more unsaturations.

In some embodiments, G$^1$ is NR$^2$ and R$^2$ is selected from the group consisting of alkyl and cycloalkyl, wherein R$^2$ optionally contains one or more unsaturations. In some embodiments, G$^1$ is NR$^2$ and R$^2$ is aryl, which is optionally substituted.

In some further embodiments, the present invention provides compounds of formula:

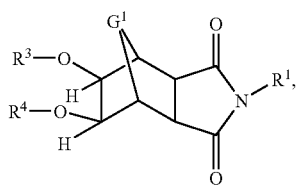

wherein $G^1$ is O, $R^1$ is phenyl, $R^3$ is selected from the group consisting of H, a linker and a linker connected to a solid support medium, and $R^4$ is selected from the group consisting of H, a protecting group, and a nucleoside linked through a phosphodiester, phosphorothioate or phosphoramidate bond, which nucleoside is optionally protected at the 5'-position or linked to one or more further nucleosides through an intra-nucleoside linker. In some embodiments, $R^3$ and $R^4$ are each H. In some embodiments, $R^3$ is H and $R^4$ is a protecting group. In some embodiments, $R^3$ is H and $R^4$ is an acid-labile protecting group. In some embodiments, $R^3$ is a linker and $R^4$ is H. In some embodiments, $R^3$ is a linker and $R^4$ is a protecting group. In some embodiments, $R^3$ is a linker and $R^4$ is an acid-labile protecting group. In some embodiments, $R^3$ is a linker connected to a solid support medium and $R^4$ is H. In some embodiments, $R^3$ is a linker connected to a solid support medium and $R^4$ is a nucleoside, optionally protected with a protecting group. In some embodiments, $R^3$ is a linker connected to a solid support medium and $R^4$ is a nucleoside with a free 5'-OH group. In some embodiments, $R^3$ is a linker connected to a solid support medium and $R^4$ is a 5'-protected nucleoside. In some embodiments, $R^3$ is a linker connected to a solid support medium and $R^4$ is a nucleoside connected to one or more further nucleosides through a suitable intra-nucleoside linker.

In some further embodiments, the present invention provides compounds of formula:

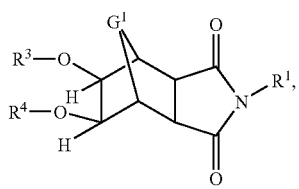

wherein $G^1$ is O, S or $NR^2$; $R^2$ is a substituent and $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, $R^3$ is a member of the group consisting of H, a linker and a linker connected to a solid support medium, and $R^4$ is a member of the group consisting of H, a protecting group, and a nucleoside linked through a phosphodiester, phosphorothioate or phosphoramidate linker, which nucleoside is optionally protected at the 5'-position or linked to one or more further nucleosides through an intra-nucleoside linker.

In some embodiments, the present invention provides compounds of the formula:

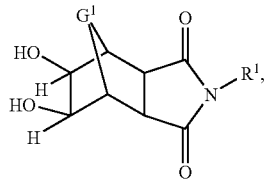

wherein $G^1$ is O, S or $NR^2$, $R^2$ is a substituent and $R^1$ is phenyl. In some embodiments, $G^1$ is O. In some embodiments, $G^1$ is S. In some embodiments, $G^1$ is $NR^2$. In some embodiments, $G^1$ is $NR^2$ and $R^2$ is a member of the group consisting of alkyl, cycloalkyl, aryl, heterocyclyl or heteroaryl, wherein $R^2$ is optionally further substituted and wherein each $R^2$ optionally contains one or more unsaturations. In some embodiments, $G^1$ is $NR^2$ and $R^2$ is a member of the group consisting of alkyl and cycloalkyl, wherein $R^2$ optionally contains one or more unsaturations. In some embodiments, $G^1$ is $NR^2$ and $R^2$ is aryl, which is optionally substituted. In some embodiments, $R^1$ is further substituted with from 1 to 5 substituents. In some embodiments, $R^1$ is aryl, which is optionally further substituted. In some embodiments, $R^1$ is phenyl or naphthyl, which is optionally further substituted. In some embodiments, $R^1$ is phenyl or naphthyl, which is unsubstituted or substituted with from 1 to about 5 members of the group consisting of F, Cl, Br, I, $NO_2$, $C_1$-$C_{12}$ alkyl and $CF_3$. In some embodiments, $R^1$ is phenyl or naphthyl, which is unsubstituted. In some embodiments, $R^1$ is heterocyclyl, and $R^1$ is optionally further substituted. In some embodiments, $R^1$ is pyridiyl, pyrimidinyl, quinolinyl, isoquinolinyl, quinazolinyl, quinoxalinyl, furanyl, thiophenyl, thiazolyl, pyrrolyl or imidazolyl and $R^1$ is optionally further substituted. In some embodiments, $R^1$ is pyridyl, furanyl or thiophenyl and $R^1$ is optionally further substituted. In some embodiments, $R^1$ is pyridiyl, furanyl, or thiophenyl, and $R^1$ is not further substituted. In some embodiments, $R^1$ is N-alkyl-morpholinyl, N-alkyl-piperidinyl or N,N'-dialkylpiperazinyl, and $R^1$ is optionally further substituted. In some embodiments, $G^1$ is O. In some embodiments, $G^1$ is S. In some embodiments, $G^1$ is $NR^2$. In some embodiments, $G^1$ is $NR^2$ and $R^2$ is a member of the group consisting of alkyl, cycloalkyl, aryl, heterocyclyl or heteroaryl, wherein $R^2$ is optionally further substituted and wherein each $R^2$ optionally contains one or more unsaturations. In some embodiments, $G^1$ is $NR^2$ and $R^2$ is a member of the group consisting of alkyl and cycloalkyl, wherein $R^2$ optionally contains one or more unsaturations. In some embodiments, $G^1$ is $NR^2$ and $R^2$ is aryl, which is optionally substituted. In some embodiments, $R^3$ and $R^4$ are each H. In some embodiments, $R^3$ is H and $R^4$ is a protecting group. In some embodiments, $R^3$ is H and $R^4$ is an acid-labile protecting group. In some embodiments, $R^3$ is a linker and $R^4$ is H. In some embodiments, $R^3$ is a linker and $R^4$ is a protecting group.

In some embodiments, $R^3$ is a linker and $R^4$ is an acid-labile protecting group. In some embodiments, $R^3$ is a linker connected to a solid support medium and $R^4$ is H. In some embodiments, $R^3$ is a linker connected to a solid support medium and $R^4$ is a nucleoside, optionally protected with a protecting group. In some embodiments, $R^3$ is a linker connected to a solid support medium and $R^4$ is a nucleoside with a free 5'-OH group. In some embodiments, $R^3$ is a linker connected to a solid support medium and $R^4$ is a 5'-protected nucleoside. In some embodiments, $R^3$ is a linker connected to a solid support medium and $R^4$ is a nucleoside connected to one or more further nucleosides through a suitable intranucleoside linker.

In some further embodiments, the present invention provides processes for making a product of the formula:

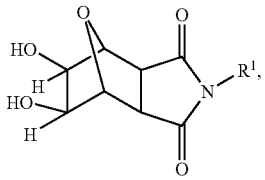

wherein $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

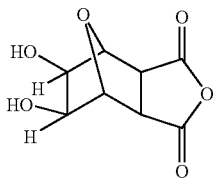

with a compound of formula: $NH_2-R^1$, wherein aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, under conditions sufficient to produce the product.

In some further embodiments, the present invention provides processes of making a product of formula:

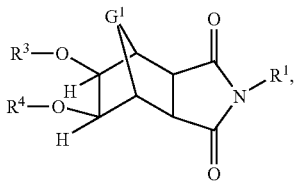

wherein $G^1$ is O, $R^3$ is H, $R^4$ is pg, wherein pg is a protecting group; $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

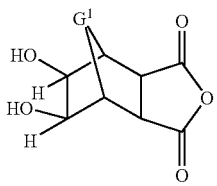

with a reactant of formula: $H_2NR^1$ under conditions suitable to produce an imide intermediate of formula:

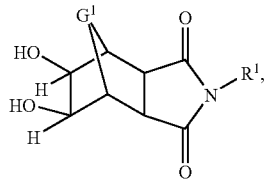

and reacting the imide intermediate with a compound of formula lg-pg, wherein lg is a leaving group and pg is a protecting group, to form the product. In some embodiments, $R^1$ is optionally substituted aryl or alkyl substituted with optionally substituted aryl. In some embodiments, $R^1$ is aryl. In some embodiments, $R^1$ is phenyl. In some embodiments, $R^1$ is alkyl substituted with aryl. In some embodiments, lg is a chloro group and pg is a 4,4'-dimethoxytriphenylmethyl group. In some embodiments, the invention provides processes of making a product of the formula:

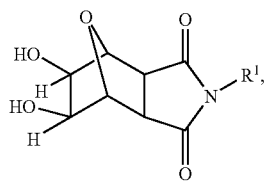

wherein $R^1$ is phenyl, the process comprising reacting an intermediate of formula:

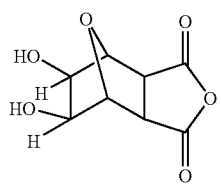

with a compound of formula: $NH_2-R^1$, wherein $R^1$ is phenyl, under conditions sufficient to produce the product.

In some embodiments, the invention provides processes for making a product of formula:

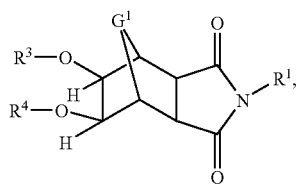

wherein $G^1$ is O, S or $NR^2$, wherein $R^2$ is a member of the group consisting of alkyl, cycloalkyl, aryl, heterocyclyl or heteroaryl, wherein $R^2$ is optionally further substituted and wherein each $R^2$ optionally contains one or more unsaturations; $R^3$ is H, $R^4$ is pg, wherein pg is a protecting group; $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

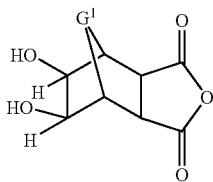

with a reactant of formula: $H_2NR^1$ under conditions suitable to produce an imide intermediate of formula:

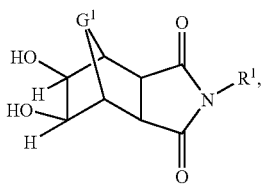

and reacting the imide intermediate with a compound of formula lg-pg, wherein lg is a leaving group and pg is a protecting group, to form the product. In some embodiments, $R^1$ is optionally substituted aryl or alkyl substituted with optionally substituted aryl. In some embodiments, $R^1$ is aryl. In some embodiments, $R^1$ is phenyl. In some embodiments, $R^1$ is alkyl substituted with aryl. In some embodiments, $R^1$ is benzyl. In some embodiments, lg is a chloro group and pg is a 4,4'-dimethoxytriphenylmethyl group.

In some embodiments, the invention provides processes of making a product of formula:

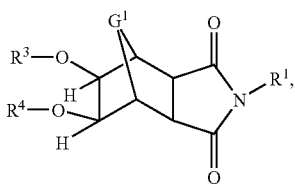

wherein $G^1$ is O, $R^3$ is H, $R^4$ is pg, wherein pg is a protecting group; $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

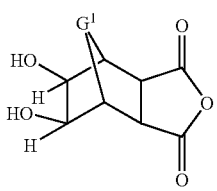

with a reactant of formula: $H_2NR^1$ under conditions suitable to produce an imide intermediate of formula:

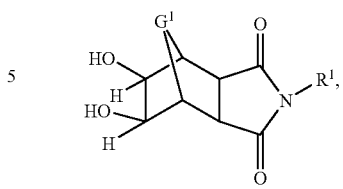

and reacting the imide intermediate with a compound of formula lg-pg, wherein lg is a leaving group and pg is a protecting group, to form the product.

In some embodiments, $R^1$ is optionally substituted aryl or alkyl substituted with optionally substituted aryl. In some embodiments, $R^1$ is aryl. In some embodiments, $R^1$ is phenyl. In some embodiments, $R^1$ is alkyl substituted with aryl. In some embodiments, $R^1$ is benzyl. In some embodiments, lg is a chloro group and pg is a 4,4'-dimethoxytriphenylmethyl group.

In some embodiments, the invention provides processes of making a product of the formula:

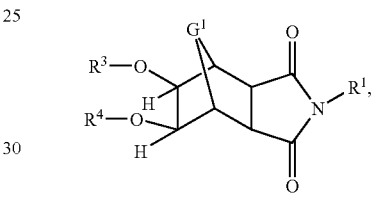

wherein $G^1$ is O, $R^3$ is H, $R^4$ is pg, wherein pg is a protecting group; and $R^1$ is phenyl, the process comprising reacting an intermediate of formula:

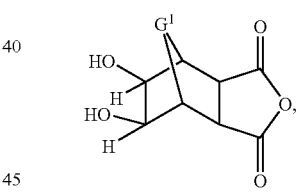

wherein $G^1$ is O;
with a compound of formula: $NH_2$—$R^1$, wherein $R^1$ is phenyl, under conditions sufficient to produce an imide intermediate of formula:

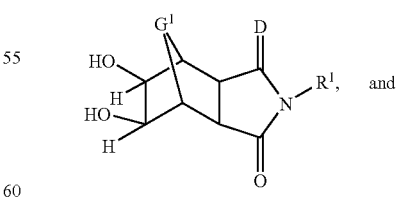

reacting the imide intermediate with a compound of formula: lg-pg, wherein lg is a leaving group and pg is a protecting group under conditions sufficient to produce the product.

In some further embodiments, the invention provides processes of making a product of formula:

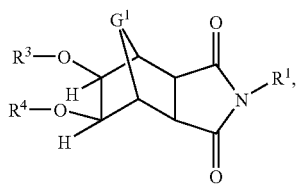

wherein $G^1$ is O, S or $NR^2$, wherein $R^2$ is a member of the group consisting of alkyl, cycloalkyl, aryl, heterocyclyl or heteroaryl, wherein $R^2$ is optionally further substituted and wherein each $R^2$ optionally contains one or more unsaturations; $R^3$ is $L^1$, wherein $L^1$ is a linking moiety, $R^4$ is pg, wherein pg is a protecting group; $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

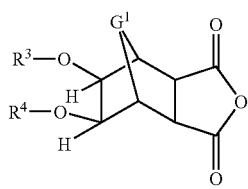

with a reactant of formula: $H_2NR^1$ under conditions suitable to produce an imide intermediate of formula:

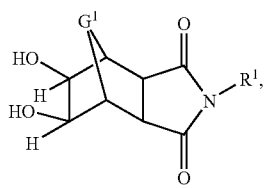

reacting the imide intermediate with a compound of formula lg-pg, wherein lg is a leaving group and pg is a protecting group, to form a protected intermediate of the formula:

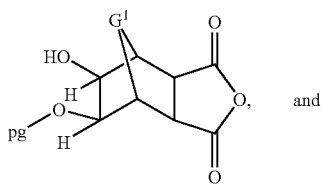
and reacting the protected intermediate with a reagent suitable to introduce the $L^1$ moiety, under conditions suitable to produce the product. In some embodiments, $R^1$ is optionally substituted aryl or alkyl substituted with optionally substituted aryl. In some embodiments, $R^1$ is aryl. In some embodiments, $R^1$ is phenyl. In some embodiments, $R^1$ is alkyl substituted with aryl. In some embodiments, $R^1$ is benzyl. In some embodiments, lg is a chloro group. In some embodiments, pg is a 4,4'-dimethoxytriphenylmethyl group, a 4-methoxytriphenylmethyl group, a pixyl group or a further substituted pixyl group. In some embodiments, the reagent suitable to introduce the $L^1$ moiety is an anhydride. In some embodiments, the reagent suitable to introduce the $L^1$ moiety is a cyclic anhydride. In some embodiments, the reagent suitable to introduce the $L^1$ moiety is succinic anhydride, and the linking moiety $L^1$ is a residue of succinic acid condensed with an hydroxyl group to form an ester bond at one end of $L^1$ and a free carboxylate at the other end.

In some further embodiments, the invention provides processes for making a product of formula:

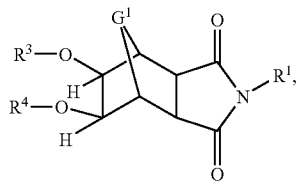

wherein $G^1$ is O; $R^3$ is $L^1$, wherein $L^1$ is a linking moiety, $R^4$ is pg, wherein pg is a protecting group; $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

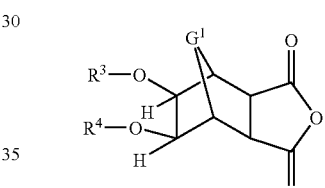

with a reactant of formula: $H_2NR^1$ under conditions suitable to produce an imide intermediate of formula:

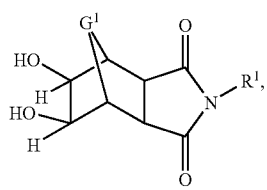

reacting the imide intermediate with a compound of formula lg-pg, wherein lg is a leaving group and pg is a protecting group, to form a protected intermediate of the formula:

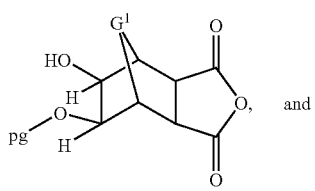
and reacting the protected intermediate with a reagent suitable to introduce the $L^1$ moiety, under conditions suitable to produce the product. In some embodiments, $R^1$ is optionally substituted aryl or alkyl substituted with optionally substituted aryl. In some embodiments, $R^1$ is aryl. In some embodiments, $R^1$ is phenyl. In some embodiments, $R^1$ is alkyl substituted with aryl. In some embodiments, $R^1$ is benzyl. In some embodiments, lg is a chloro group. In some embodiments, pg is a 4,4'-dimethoxytriphenylmethyl group, a 4-methoxytriphenylmethyl group, a pixyl group or a further substituted pixyl group. In some embodiments, the reagent suitable to introduce the $L^1$ moiety is an anhydride. In some embodiments, the reagent suitable to introduce the $L^1$ moiety is a cyclic anhydride. In some embodiments, the reagent suitable to introduce the $L^1$ moiety is succinic anhydride and the linking moiety $L^1$ is a residue of succinic acid condensed with an hydroxyl group to form an ester bond at one end of $L^1$ and a free carboxylate at the other end.

In some further embodiments, the invention provides processes of making a product of formula:

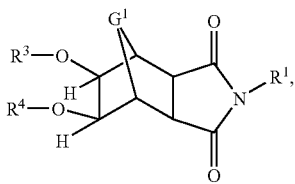

wherein $G^1$ is O, S or $NR^2$, wherein $R^2$ is a member of the group consisting of alkyl, cycloalkyl, aryl, heterocyclyl or heteroaryl, wherein $R^2$ is optionally further substituted and wherein each $R^2$ optionally contains one or more unsaturations; $R^3$ is $L^1$-SS, wherein $L^1$ is a linking moiety and SS is a solid support medium, $R^4$ is pg, wherein pg is a protecting group; $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

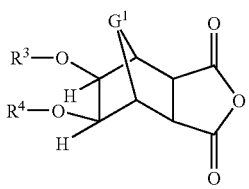

with a reactant of formula: $H_2NR^1$ under conditions suitable to produce an imide intermediate of formula:

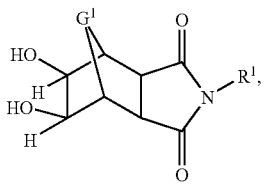

reacting the imide intermediate with a compound of formula lg-pg, wherein lg is a leaving group and pg is a protecting group, to form a protected intermediate of the formula:

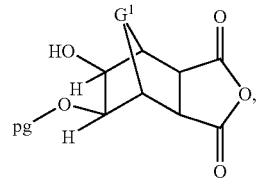

reacting the protected intermediate with a reagent suitable to introduce the $L^1$ moiety, under conditions suitable to produce a support intermediate of the formula:

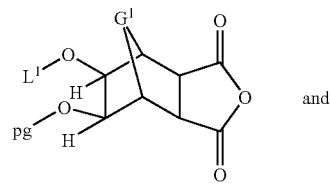 and reacting the support intermediate with a solid support medium under conditions suitable to produce the product. In some embodiments, $R^1$ is optionally substituted aryl or alkyl substituted with optionally substituted aryl. In some embodiments, $R^1$ is aryl. In some embodiments, $R^1$ is phenyl. In some embodiments, $R^1$ is alkyl substituted with aryl. In some embodiments, $R^1$ is benzyl. In some embodiments, lg is a chloro group. In some embodiments, pg is a 4,4'-dimethoxytriphenylmethyl group, a 4-methoxytriphenylmethyl group, a pixyl group or a further substituted pixyl group. In some embodiments, the reagent suitable to introduce the $L^1$ moiety is an anhydride. In some embodiments, the reagent suitable to introduce the $L^1$ moiety is a cyclic anhydride. In some embodiments, the reagent suitable to introduce the $L^1$ moiety is succinic anhydride, and the linking moiety $L^1$ is a residue of succinic acid condensed with an hydroxyl group to form an ester bond at one end of $L^1$ and a free carboxylate at the other end. In some embodiments, SS is controlled pore glass or a polystyrene bead.

In some further embodiments, the invention provides processes for making a product of formula:

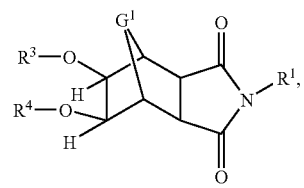

wherein $G^1$ is O; $R^3$ is $L^1$-SS, wherein $L^1$ is a linking moiety and SS is a solid support medium, wherein $L^1$ is a linking moiety, $R^4$ is pg, wherein pg is a protecting group; $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

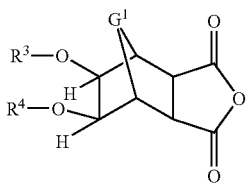

with a reactant of formula: $H_2NR^1$ under conditions suitable to produce an imide intermediate of formula:

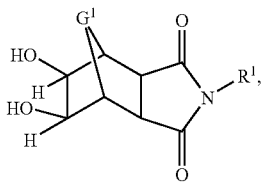

reacting the imide intermediate with a compound of formula lg-pg, wherein lg is a leaving group and pg is a protecting group, to form a protected intermediate of the formula:

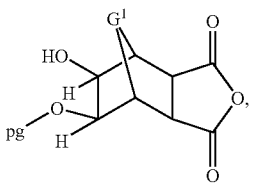

reacting the protected intermediate with a reagent suitable to introduce the $L^1$ moiety, under conditions suitable to produce a support intermediate of formula:

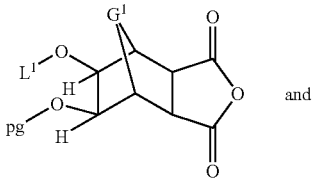

and reacting the support intermediate with a solid support medium having a suitable functional group under conditions suitable to produce the product. In some embodiments, $R^1$ is optionally substituted aryl or alkyl substituted with optionally substituted aryl. In some embodiments, $R^1$ is aryl. In some embodiments, $R^1$ is phenyl. In some embodiments, $R^1$ is alkyl substituted with aryl. In some embodiments, $R^1$ is benzyl. In some embodiments, lg is a chloro group. In some embodiments, pg is a 4,4'-dimethoxytriphenylmethyl group, a 4-methoxytriphenylmethyl group, a pixyl group or a further substituted pixyl group. In some embodiments, the reagent suitable to introduce the $L^1$ moiety is an anhydride. In some embodiments, the reagent suitable to introduce the $L^1$ moiety is a cyclic anhydride. In some embodiments, the reagent suitable to introduce the $L^1$ moiety is succinic anhydride and the linking moiety $L^1$ is a residue of succinic acid condensed with an hydroxyl group to form an ester bond at one end of $L^1$ and a free carboxylate at the other end.

In some further embodiments, the invention provides processes for making a product of formula:

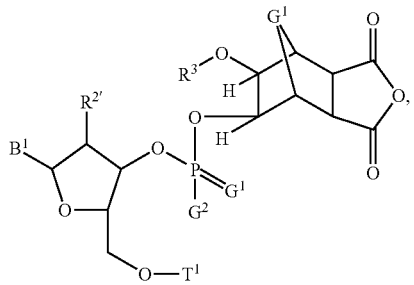

wherein $B^1$ is a nucleobase, $G^1$ is O or S, $G^2$ is $OT^2$, $ST^2$ or $NR^{N'}N^{N'}$, $R^2$ is a H, OH, protected OH or a substituent; $T^1$ is a protecting group, $G^1$ is O, S or $NR^2$, wherein $R^2$ is a member of the group consisting of alkyl, cycloalkyl, aryl, heterocyclyl or heteroaryl, wherein $R^2$ is optionally further substituted and wherein each $R^2$ optionally contains one or more unsaturations; $R^3$ is $L^1$-SS, wherein $L^1$ is a linking moiety and SS is a solid support medium, $R^4$ is pg, wherein pg is a protecting group; $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

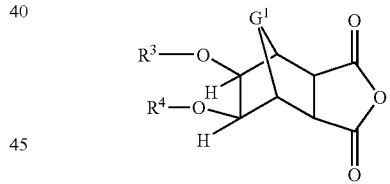

with a reactant of formula: $H_2NR^1$ under conditions suitable to produce an imide intermediate of formula:

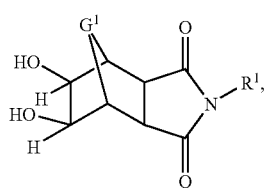

reacting the imide intermediate with a compound of formula lg-pg, wherein lg is a leaving group and pg is a protecting group, to form a protected intermediate of the formula:

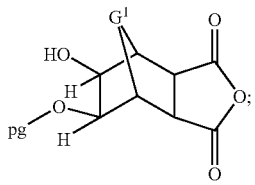

reacting the protected intermediate with a reagent suitable to introduce the $L^1$ moiety, under conditions suitable to produce a support intermediate of the formula:

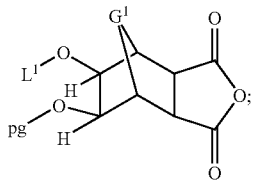

reacting the support intermediate with a solid support medium under conditions suitable to produce an oligonucleotide synthesis support of the formula:

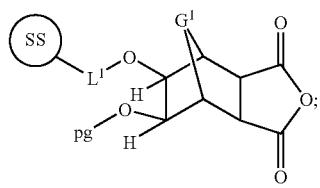

reacting the oligonucleotide synthesis support with an acid to remove pg and form a de-protected oligonucleotide synthesis support, then reacting the deprotected oligonucleotide synthesis support with an activated nucleoside:

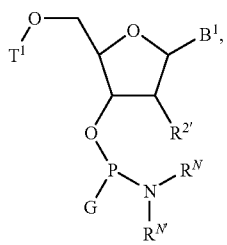

wherein G is $OT^2$, $ST^2$ or $NR^N R^N$, wherein $T^2$ is a blocking group and $R^N$ and $R^N$ independently are alkyl or together with the N to which they are attached form a heterocylic ring structure, under conditions suitable to produce the intermediate:

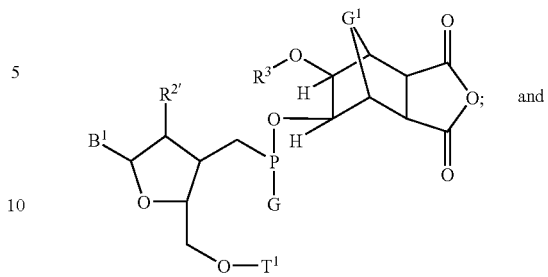

oxidizing the intermediate to form the product. In some embodiments, $R^1$ is optionally substituted aryl or alkyl substituted with optionally substituted aryl. In some embodiments, $R^1$ is aryl. In some embodiments, $R^1$ is phenyl. In some embodiments, $R^1$ is alkyl substituted with aryl. In some embodiments, $R^1$ is benzyl. In some embodiments, 1g is a chloro group. In some embodiments, pg is a 4,4'-dimethoxytriphenylmethyl group, a 4-methoxytriphenylmethyl group, a pixyl group or a further substituted pixyl group. In some embodiments, the reagent suitable to introduce the $L^1$ moiety is an anhydride. In some embodiments, the reagent suitable to introduce the $L^1$ moiety is a cyclic anhydride. In some embodiments, the reagent suitable to introduce the $L^1$ moiety is succinic anhydride, and the linking moiety $L^1$ is a residue of succinic acid condensed with an hydroxyl group to form an ester bond at one end of $L^1$ and a free carboxylate at the other end. In some embodiments, SS is controlled pore glass or a polystyrene bead. In some embodiments, $B^1$ is a member of the group consisting of thyminyl, cytosinyl, uridinyl, 5-methylcytosinyl, guanyl and adeninyl. In some embodiments, $R^{2'}$ is a member of the group consisting of H, OH, F, OMe, $OCH_2CH_2OMe$, $OCH_2CH_2CH_2NH_2$, and OY, wherein Y is a removable protecting group. In some embodiments, $T^1$ is a removable protecting group. In some embodiments, $T^1$ is an acid-labile protecting group. In some embodiments, $T^1$ is selected from the group consisting of 4,4'-dimethoxytriphenylmethyl group, a 4-methoxytriphenylmethyl group, a pixyl group or a further substituted pixyl group. In some embodiments, $T^1$ is a 4,4'-dimethoxytriphenylmethyl group.

In some further embodiments, the invention provides processes for making a product of formula:

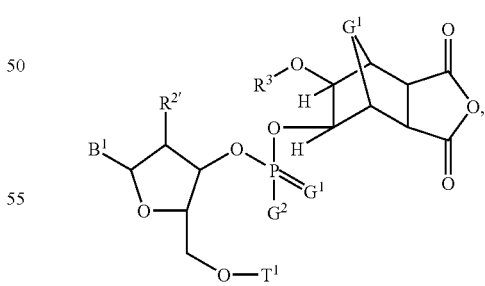

wherein $B^1$ is a nucleobase, $R^{2'}$ is a H, OH, protected OH or a substituent; $T^1$ is a protecting group; $G^1$ is O; $R^3$ is $L^1$-SS, wherein $L^1$ is a linking moiety and SS is a solid support medium, wherein $L^1$ is a linking moiety, $R^4$ is pg, wherein pg is a protecting group; $R^1$ is aryl, cycloalkyl, unsaturated cycloalkyl, alkyl, unsaturated alkyl, heterocyclyl, unsaturated heterocyclyl, heteroaryl or acyl, wherein $R^1$ is optionally substituted with one or more substituents, the process comprising reacting an intermediate of formula:

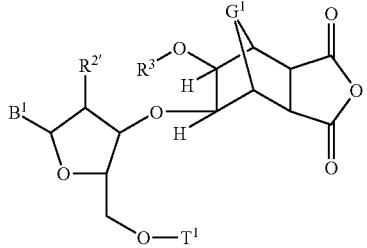

with a reactant of formula: $H_2NR^1$ under conditions suitable to produce an imide intermediate of formula:

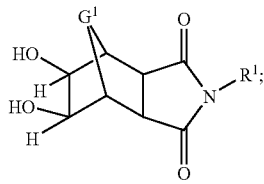

reacting the imide intermediate with a compound of formula lg-pg, wherein lg is a leaving group and pg is a protecting group, to form a protected intermediate of the formula:

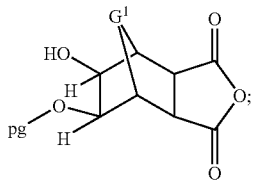

reacting the protected intermediate with a reagent suitable to introduce the $L^1$ moiety, under conditions suitable to produce a support intermediate of formula:

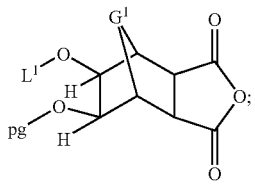

reacting the support intermediate with a solid support medium having a suitable functional group under conditions suitable to produce an oligonucleotide synthesis support of the formula:

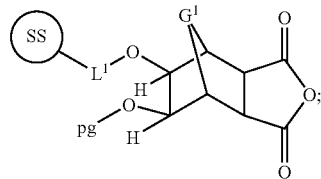

reacting the oligonucleotide synthesis support with an acid to remove pg and form a de-protected oligonucleotide synthesis support, then reacting the deprotected oligonucleotide synthesis support with an activated nucleoside:

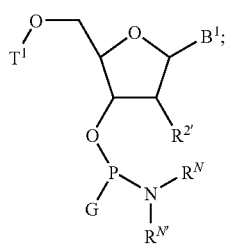

wherein G is $OT^2$, $ST^2$ or $NR^{N}R^{N'}$, wherein $T^2$ is a blocking group and $R^N$ and $R^{N'}$ independently are alkyl or together with the N to which they are attached form a heterocylic ring structure, under conditions suitable to produce the intermediate:

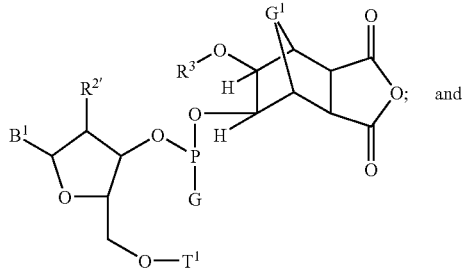

and oxidizing the intermediate to form the product. In some embodiments, $R^1$ is optionally substituted aryl or alkyl substituted with optionally substituted aryl. In some embodiments, $R^1$ is aryl. In some embodiments, $R^1$ is phenyl. In some embodiments, $R^1$ is alkyl substituted with aryl. In some embodiments, $R^1$ is benzyl. In some embodiments, lg is a chloro group. In some embodiments, pg is a 4,4'-dimethoxytriphenylmethyl group, a 4-methoxytriphenylmethyl group, a pixyl group or a further substituted pixyl group. In some embodiments, the reagent suitable to introduce the $L^1$ moiety is an anhydride. In some embodiments, the reagent suitable to introduce the $L^1$ moiety is a cyclic anhydride. In some embodiments, the reagent suitable to introduce the $L^1$ moiety is succinic anhydride and the linking moiety $L^1$ is a residue of succinic acid condensed with an hydroxyl group to form an ester bond at one end of $L^1$ and a free carboxylate at the other end. In some embodiments, $B^1$ is a member of the group consisting of thyminyl, cytosinyl, uridinyl, 5-methylcytosinyl, guanyl and adeninyl. In some embodiments, $R^{2'}$ is a member of the group consisting of H, OH, F, OMe, OCH$_2$CH$_2$OMe, OCH$_2$CH$_2$CH$_2$NH$_2$, and OY, wherein Y is a removable protecting group. In some embodiments, T$^1$ is a removable protecting group. In some embodiments, T$^1$ is an acid-labile protecting group. In some embodiments, T$^1$ is selected from the group consisting of 4,4'-dimethoxytriphenylmethyl group, a 4-methoxytriphenylmethyl group, a pixyl group or a further substituted pixyl group. In some embodiments, T$^1$ is a 4,4'-dimethoxytriphenylmethyl group.

In some further embodiments, the present invention provides processes for making a product of the formula:

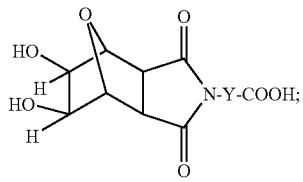

wherein Y is alkylene, cycloalkylene, arylene, heteroarylene, arylalkylene, alkarylene, or alkylenearylalkylene, the process comprising reacting an intermediate of the formula:

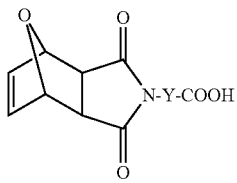

with a suitable oxidizing reagent to form the product. In some embodiments, the suitable oxidizing reagent is H$_2$O$_2$, optionally in the presence of a catalyst.

In some further embodiments, the present invention provides processes of making a product of the formula:

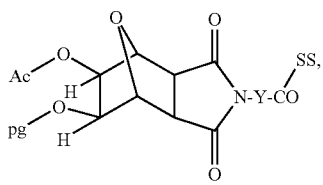

wherein Y is alkylene, cycloalkylene, arylene, heteroarylene, arylalkylene, alkarylene, or alkylenearylalkylene, SS is a solid support medium, Ac is an acyl blocking group and pg is a protecting group the process comprising reacting a compound of formula:

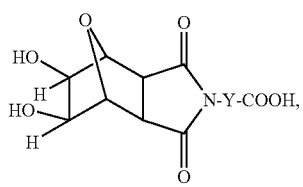

with a protecting reagent of formula lg-pg, wherein lg is a leaving group and pg is a protecting group, to form a protected intermediate of formula:

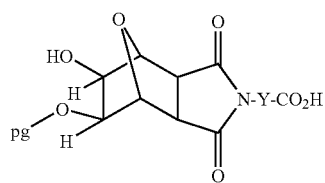

and reacting the protected intermediate with an acylating reagent to form a protected-blocked intermediate of formula:

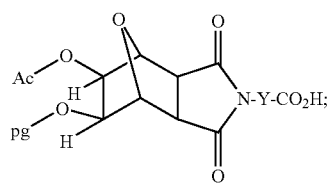

wherein Ac is a blocking group, and reacting the protected-blocked intermediate with a suitable solid support medium to form the product. In some embodiments, pg is an acid labile protecting group. In some embodiments, Ac is a base labile blocking group. In some embodiments, pg and Ac are labile under orthogonal conditions.

In some further embodiments, the invention provides processes for making a product of the formula:

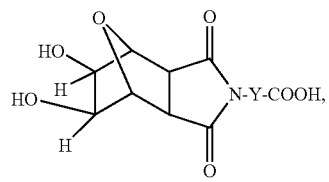

wherein Y is alkylene, cycloalkylene, arylene, heteroarylene, arylalkylene, alkarylene, or alkylenearylalkylene, the process comprising reacting an intermediate of the formula:

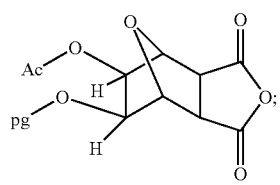

wherein Ac is a blocking group and pg is a protecting group, with a reagent of the formula NH$_2$—Y—COOH under conditions suitable to produce the product.

In some further embodiments, the invention provides processes for making a product of the formula:

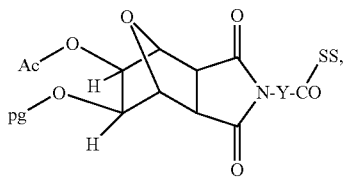

wherein Y is alkylene, cycloalkylene, arylene, heteroarylene, arylalkylene, alkarylene, or alkylenearylalkylene, SS is a solid support medium, Ac is an acyl blocking group and pg is a protecting group the process comprising reacting a compound of formula:

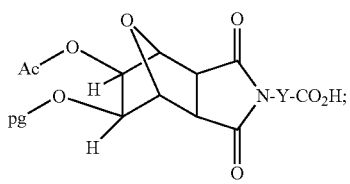

wherein Ac is a blocking group, and reacting the protected-blocked intermediate, with a suitable solid support medium SS to form the product. In some embodiments, pg is an acid labile protecting group. In some embodiments, Ac is a base labile blocking group. In some embodiments, pg and Ac are labile under orthogonal conditions.

The present invention further provides compounds of the formula:

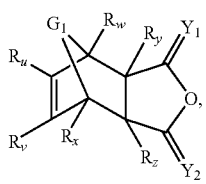

wherein $G^1$ is O, S or $NR^1$, $R^1$ is H or a substituent, each of $R_u$, $R_v$, $R_w$, $R_x$, $R_y$ and $R_z$ is independently H, $C_1$-$C_{12}$ alkyl, aryl, heteroalkyl, arylalkyl; $Y_1$ is O, S, $CH_2$, or $CR_{y1'}R_{y1''}$, wherein each of $R_{y1'}$ and $R_{y1''}$ is independently optionally substituted $C_1$-$C_{12}$ alkyl, $Y_2$ is O, S, $CH_2$, or $CR_{y2'}R_{y2''}$, wherein each of $R_{y2'}$ and $R_{y2''}$ is optionally substituted $C_1$-$C_{12}$ alkyl.

In some further embodiments, the invention provides compounds of the formula:

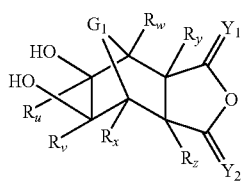

wherein $G^1$ is O, S or $NR^1$, $R^1$ is H or a substituent, each of $R_u$, $R_v$, $R_w$, $R_x$, $R_y$ and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl, $Y_2$ is O, S, $CH_2$, or $CR_{y2'}R_{2''}$, wherein each of $R_{y2'}$ and $R_{y2''}$ is optionally substituted $C_1$-$C_{12}$ alkyl.

In some further embodiments, the invention provides compounds of the formula:

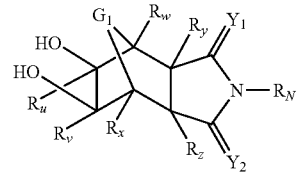

wherein $G^1$ is O, S or $NR^1$, $R^1$ is H or a substituent; each of $R_u$, $R_v$, $R_w$, $R_x$, $R_y$ and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2''}$ wherein each of $R_{y2'}$ and $R_{y2''}$ is optionally substituted $C_1$-$C_2$ alkyl; and $R_N$ is H or a substituent.

In some further embodiments, the invention provides compounds of the formula:

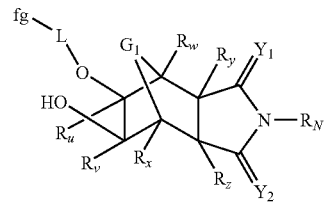

wherein $G^1$ is O, S or $NR^1$, $R^1$ is H or a substituent; each of $R_u$, $R_v$, $R_w$, $R_x$, $R_y$ and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y'}$ and $R_{y1''}$ is independently optionally substituted $C_1$-$C_{12}$ alkyl; $Y_2$ is O, S, $CH_2$, or $CR_{y2'}R_{2''}$ wherein each of $R_{y2'}$ and $R_{y2''}$ is optionally substituted $C_1$-$C_{12}$ alkyl; $R_N$ is H or a substituent; and L is a linking group and fg is a functional group.

In some further embodiments, the invention provides compounds of the formula:

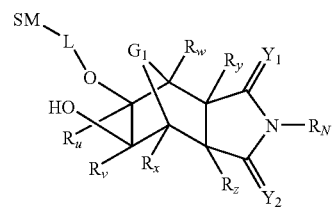

wherein $G^1$ is O, S or $NR^1$, $R^1$ is H or a substituent; each of $R_u$, $R_v$, $R_w$, $R_x$, $R_y$ and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y'}$ and $R_{y1''}$ is independently optionally substituted $C_1$-$C_{12}$ alkyl; $Y_2$ is O, S, $CH_2$, or $CR_{y2'}R_{2''}$ wherein each of $R_{y2'}$ and $R_{y2''}$ is optionally substituted $C_1$-$C_{12}$ alkyl; $R_N$ is H or a substituent; L is a linking group and fg is a functional group; and SM is a support medium.

In some further embodiments, the invention provides compounds of the formula:

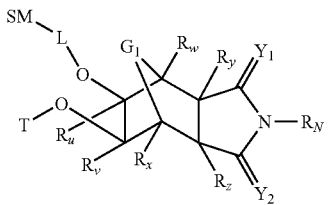

wherein $G^1$ is O, S or $NR^1$, $R^1$ is H or a substituent; each of $R_u$, $R_v$, $R_w$, $R_x$, $R^y$, and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2'''}$, wherein each of $R_{y2'}$ and $R_{y2''}$ is optionally substituted $C_1$-$C_{12}$ alkyl; $R_N$ is H or a substituent; L is a linking group and fg is a functional group; T is a labile protecting group; and SM is a support medium.

In some further embodiments, the invention provides compounds of the formula:

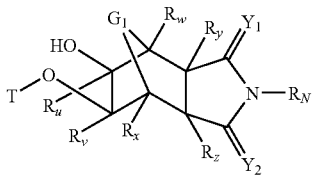

wherein $G^1$ is O, S or $NR^1$, $R^1$ is H or a substituent; each of $R_u$, $R_v$, $R_w$, $R_x$, $R_y$ and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2'''}$, wherein each of $R_{y2'}$ and $R_{y2''}$ is optionally substituted $C_1$-$C_{12}$ alkyl; $R_N$ is H or a substituent; and T is a labile protecting group.

In some further embodiments, the invention provides compounds of the formula:

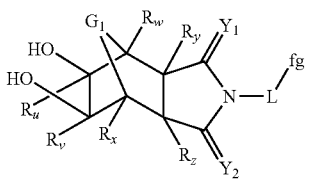

wherein $G^1$ is O, S or $NR^1$, $R^1$ is H or a substituent; each of $R_u$, $R_v$, $R_w$, $R_x$, $R_y$ and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2'''}$, wherein each of $R_{y2'}$ and $R_{y2''}$ is optionally substituted $C_1$-$C_{12}$ alkyl; $R_N$ is H or a substituent; L is a linking group; and fg is a functional group.

In some further embodiments, the invention provides compounds of the formula:

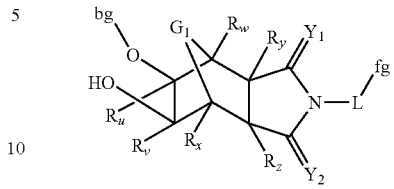

wherein $G^1$ is O, S or $NR^1$, $R^1$ is H or a substituent; each of $R_u$, $R^v$, $R_w$, $R_x$, $R_y$, and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2'''}$, wherein each of $R_{y2'}$ and $R_{y2''}$ is optionally substituted $C_1$-$C_{12}$ alkyl; $R_N$ is H or a substituent; L is a linking group; fg is a functional group; and bg is a blocking group.

In some further embodiments, the invention provides compounds of the formula:

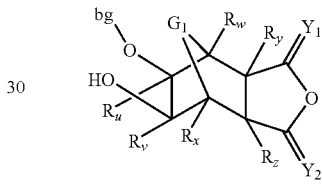

wherein $G^1$ is O, S or $NR^1$; $R^1$ is H or a substituent; each of $R_u$, $R^v$, $R^w$, $R_x$, $R_y$, and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2'''}$, wherein each of $R_{y2'}$ and $R_{y2''}$ is optionally substituted $C_1$-$C_{12}$ alkyl.

In some further embodiments, the invention provides compounds of the formula:

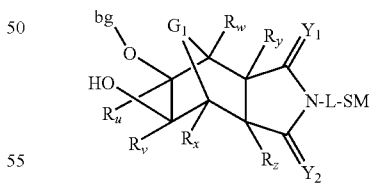

wherein $G^1$ is O, S or $NR^1$, $R^1$ is H or a substituent; each of $R_u$, $R^v$, $R_w$, $R_x$, $R_y$, and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2'''}$, wherein each of $R_{y2'}$ and $R_{y2''}$ is optionally substituted $C_1$-$C_{12}$ alkyl; L is a linking group and fg is a functional group; bg is a blocking group; and SM is a support medium.

In some further embodiments, the invention provides compounds of the formula:

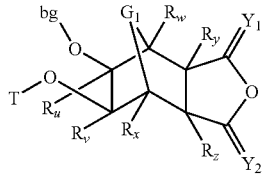

wherein $G^1$ is O, S or $NR^1$, $R^1$ is H or a substituent; each of $R_u$, $R_v$, $R_w$, $R_x$, $R_y$, and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2''}$, wherein each of $R_{y2'}$ and $R_{y2''}$ is optionally substituted $C_1$-$C_{12}$ alkyl; bg is a blocking group and T is a labile protecting group.

In some further embodiments, the invention provides compounds of the formula:

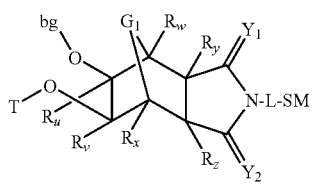

wherein $G^1$ is O, S or $NR^1$, $R^1$ is H or a substituent; each of $R_u$, $R_v$, $R_w$, $R_x$, $R_y$ and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2''}$, wherein each of $R_{y2'}$ and $R_{y2''}$ is optionally substituted $C_1$-$C_{12}$ alkyl; $R_N$ is H or a substituent; L is a linking group and fg is a functional group; bg is a blocking group; SM is a support medium; and T is a labile protecting group.

In some further embodiments, the invention provides compounds of one of the formulae:

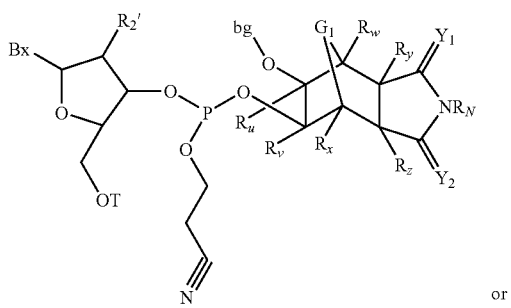

or

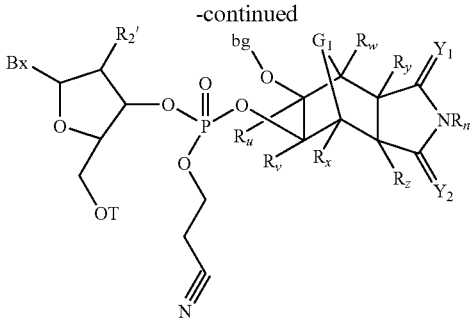

wherein $G^1$ is O, S or $NR^1$, $R^1$ is H or a substituent; each of $R_u$, $R^v$, $R_w$, $R_x$, $R_y$ and $R_z$ is independently H, $C_1$-$C_{12}$ alkyl, aryl, heteroalkyl, arylalkyl; $Y_1$ is O, S, $CH_2$, or $CR_{y'}R_{y''}$, wherein each of $R_{y1'}$ and $R_{y1''}$ is independently optionally substituted $C_1$-$C_{12}$ alkyl; $Y_2$ is O, S, $CH_2$, or $CR_{y2'}R_{2''}$, wherein each of $R_{y2'}$ and $R_{y2''}$ is optionally substituted $C_1$-$C_{12}$ alkyl; $R_N$ is H or a substituent; L is a linking group; fg is a functional group; SM is a support medium; Bx is a nucleobase which is optionally substituted; T is a labile protecting group; and Q is O or S.

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight chain or branched hydrocarbon moieties containing up to twenty four carbon atoms. The terms "$C_1$-$C_6$ alkyl" and "$C_1$-$C_{12}$ alkyl," as used herein, refer to saturated, straight chain or branched hydrocarbon moieties containing one to six carbon atoms and one to twelve carbon atoms respectively. Examples of alkyl groups include, but are not limited to, methyl, ethyl, propyl, isopropyl, n-hexyl, octyl, decyl, dodecyl and the like.

An "aliphatic group," as used herein, is an acyclic, non-aromatic moiety that may contain any combination of carbon atoms, hydrogen atoms, halogen atoms, oxygen, nitrogen, sulfur, phosphorus or other atoms, and optionally contain one or more units of unsaturation, e.g., double and/or triple bonds. An aliphatic group may be straight chained, or branched and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Suitable substituents of the present invention include, but are not limited to, F, Cl, Br, I, OH, protected hydroxy, aliphatic ethers, aromatic ethers, oxo, azido, imino, oximino, $NO_2$, CN, COOH, $C_1$-$C_{12}$ alkyl optionally substituted, $C_2$-$C_{12}$ alkenyl optionally substituted, $C_2$-$C_{12}$ alkynyl optionally substituted, $NH_2$, protected amino, $N(H)C_1$-$C_{12}$ alkyl, $N(H)C_2$-$C_{12}$ alkenyl, $N(H)C_2$-$C_{12}$ alkynyl, $N(H)C_3$-$C_{12}$ cycloalkyl, N(H) aryl, N(H) heteroaryl, N(H) heterocycloalkyl, dialkylamino, diarylamino, diheteroarylamino, $OC_1$-$C_{12}$ alkyl, $OC_2$-$C_{12}$ alkenyl, $OC_2$-$C_{12}$ alkynyl, $OC_3$-$C_{12}$ cycloalkyl, O aryl, O heteroaryl, O heterocycloalkyl, $C(O)C_1$-$C_{12}$ alkyl, $C(O)C_2$-$C_{12}$ alkenyl, $C(O)C_2$-$C_{12}$ alkynyl, $C(O)C_3$-$C_{12}$ cycloalkyl, C(O) aryl, C(O) heteroaryl, C(O) heterocycloalkyl, $C(O)NH_2$, $C(O)N(H)C_1$-$C_{12}$ alkyl, $C(O)N(H)C_2$-$C_{12}$ alkenyl, $C(O)N(H)C_2$-$C_{12}$ alkynyl, $C(O)N(H)C_3$-

$C_{12}$ cycloalkyl, C(O)N(H) aryl, C(O)N(H) heteroaryl, C(O)N(H) heterocycloalkyl, $C(O)OC_1$-$C_{12}$ alkyl, $C(O)OC_2$-$C_{12}$ alkenyl, $C(O)OC_2$-$C_{12}$ alkynyl, $C(O)OC_3$-$C_{12}$ cycloalkyl, C(O)O aryl, C(O)O heteroaryl, C(O)O heterocycloalkyl, $OC(O)NH_2$, $OC(O)N(H)C_1$-$C_{12}$ alkyl, $OC(O)N(H)C_2$-$C_{12}$ alkenyl, $OC(O)N(H)C_2$-$C_{12}$ alkynyl, $OC(O)N(H)C_3$-$C_{12}$ cycloalkyl, OC(O)N(H) aryl, OC(O)N(H) heteroaryl, OC(O)N(H) heterocycloalkyl, $N(H)C(O)C_1$-$C_{12}$ alkyl, $N(H)C(O)C_2$-$C_{12}$ alkenyl, $N(H)C(O)C_2$-$C_{12}$ alkynyl, $N(H)C(O)C_3$-$C_{12}$ cycloalkyl, N(H)C(O) aryl, N(H)C(O) heteroaryl, N(H)C(O) heterocycloalkyl, $N(H)C(O)OC_1$-$C_{12}$ alkyl, $N(H)C(O)OC_2$-$C_{12}$ alkenyl, $N(H)C(O)OC_2$-$C_{12}$ alkynyl, $N(H)C(O)OC_3$-$C_{12}$ cycloalkyl, N(H)C(O)O aryl, N(H)C(O)O heteroaryl, N(H)C(O)O heterocycloalkyl, $N(H)C(O)NH_2$, $N(H)C(O)N(H)C_1$-$C_{12}$ alkyl, $N(H)C(O)N(H)C_2$-$C_{12}$ alkenyl, $N(H)C(O)N(H)C_2$-$C_{12}$ alkynyl, $N(H)C(O)N(H)C_3$-$C_{12}$ cycloalkyl, N(H)C(O)N(H) aryl, N(H)C(O)N(H) heteroaryl, N(H)C(O)N(H) heterocycloalkyl, $N(H)C(S)NH_2$, $N(H)C(S)N(H)C_1$-$C_{12}$ alkyl, $N(H)C(S)N(H)C_2$-$C_{12}$ alkenyl, $N(H)C(S)N(H)C_2$-$C_{12}$ alkynyl, $N(H)C(S)N(H)C_3$-$C_{12}$ cycloalkyl, N(H)C(S)N(H) aryl, N(H)C(S)N(H) heteroaryl, N(H)C(S)N(H) heterocycloalkyl, $N(H)C(NH)NH_2$, $N(H)C(NH)N(H)C_1$-$C_{12}$ alkyl, $N(H)C(NH)N(H)C_2$-$C_{12}$ alkenyl, $N(H)C(NH)N(H)C_2$-$C_{12}$ alkynyl, $N(H)C(NH)N(H)C_3$-$C_{12}$ cycloalkyl, N(H)C(NH)N(H) aryl, N(H)C(NH)N(H) heteroaryl, N(H)C(NH)N(H) heterocycloalkyl, $N(H)C(NH)C_1$-$C_{12}$ alkyl, $N(H)C(NH)C_2$-$C_{12}$ alkenyl, $N(H)C(NH)C_2$-$C_{12}$ alkynyl, $N(H)C(NH)C_3$-$C_{12}$ cycloalkyl, N(H)C(NH) aryl, N(H)C(NH) heteroaryl, N(H)C(NH) heterocycloalkyl, $C(NH)NH_2$, $C(NH)N(H)C_1$-$C_{12}$ alkyl, $C(NH)N(H)C_2$-$C_{12}$ alkenyl, $C(NH)N(H)C_2$-$C_{12}$ alkynyl, $C(NH)N(H)C_3$-$C_{12}$ cycloalkyl, C(NH)N(H) aryl, C(NH)N(H) heteroaryl, C(NH)N(H) heterocycloalkyl, $S(O)C_1$-$C_{12}$ alkyl, $S(O)C_2$-$C_{12}$ alkenyl, $S(O)C_2$-$C_{12}$ alkynyl, $S(O)C_3$-$C_{12}$ cycloalkyl, S(O) aryl, S(O) heteroaryl, S(O) heterocycloalkyl, $SO_2NH_2$, $SO_2N(H)C_1$-$C_{12}$ alkyl, $SO_2N(H)C_2$-$C_{12}$ alkenyl, $SO_2N(H)C_2$-$C_{12}$ alkynyl, $SO_2N(H)C_3$-$C_{12}$ cycloalkyl, $SO_2N(H)$ aryl, $SO_2N(H)$ heteroaryl, $SO_2N(H)$ heterocycloalkyl, $N(H)SO_2$—$C_1$-$C_{12}$ alkyl, $N(H)SO_2$—$C_2$-$C_{12}$ alkenyl, $N(H)SO_2$—$C_2$-$C_{12}$ alkynyl, $N(H)SO_2$—$C_3$-$C_{12}$ cycloalkyl, $N(H)SO_2$ aryl, $N(H)SO_2$ heteroaryl, $N(H)SO_2$ heterocycloalkyl, $CH_2NH_2$, $CH_2SO_2CH_3$, aryl, arylalkyl, heteroaryl, heteroarylalkyl, heterocycloalkyl, $C_3$-$C_{12}$ cycloalkyl, polyalkoxyalkyl, polyalkoxy, methoxymethoxy, methoxyethoxy, SH, $SC_1$-$C_{12}$ alkyl, $SC_2$-$C_{12}$ alkenyl, $SC_2$-$C_{12}$ alkynyl, $SC_3$-$C_{12}$ cycloalkyl, S aryl, S heteroaryl, S heterocycloalkyl, or methylthiomethyl. It is understood that the aryls, heteroaryls, alkyls and the like can be further substituted.

The term "alkenyl," as used herein, refers to a straight chain or branched hydrocarbon moiety containing up to twenty four carbon atoms having at least one carbon-carbon double bond. The terms "$C_2$-$C_6$ alkenyl" and "$C_2$-$C_{12}$ alkenyl," as used herein, refer to straight chain or branched hydrocarbon moieties containing two to six carbon atoms and two to twelve carbon atoms respectively and having at least one carbon-carbon double bond. Examples of alkenyl groups include, but are not limited to, ethenyl, propenyl, butenyl, 1-methyl-2-buten-1-yl, alkadienes and the like.

The term "substituted alkenyl," as used herein, refers to an "alkenyl" or "$C_2$-$C_{12}$ alkenyl" or "$C_2$-$C_6$ alkenyl," group as previously defined, substituted by one, two, three or more substituents.

The term "alkynyl," as used herein, refers to a straight chain or branched hydrocarbon moiety containing up to twenty four carbon atoms and having at least one carbon-carbon triple bond. The terms "$C_2$-$C_6$ alkynyl" and "$C_2$-$C_{12}$ alkynyl," as used herein, refer to straight chain or branched hydrocarbon moieties containing two to six carbon atoms and two to twelve carbon atoms respectively and having at least one carbon-carbon triple bond. Examples of alkynyl groups include, but are not limited to, ethynyl, 1-propynyl, 1-butynyl, and the like.

The term "substituted alkynyl," as used herein, refers to an "alkynyl" or "$C_2$-$C_6$ alkynyl" or "$C_2$-$C_{12}$ alkynyl," group as previously defined, substituted by one, two, three or more substituents.

The term "alkoxy," as used herein, refers to an aliphatic group, as previously defined, attached to the parent molecular moiety through an oxygen atom. Examples of alkoxy include, but are not limited to, methoxy, ethoxy, propoxy, isopropoxy, n-butoxy, sec-butoxy, tert-butoxy, n-pentoxy, neopentoxy, n-hexoxy and the like.

The term "substituted alkoxy," as used herein, refers to an alkoxy group as previously defined substituted with one, two, three or more substituents.

The terms "halo" and "halogen," as used herein, refer to an atom selected from fluorine, chlorine, bromine and iodine.

The terms "aryl" or "aromatic," as used herein, refer to a mono- or polycyclic carbocyclic ring system having one or more aromatic rings. Examples of aryl groups include, but not limited to, phenyl, naphthyl, tetrahydronaphthyl, indanyl, idenyl and the like.

The terms "substituted aryl" or "substituted aromatic," as used herein, refer to an aryl or aromatic group as previously defined substituted by one, two, three or more substituents.

The term "arylalkyl," as used herein, refers to an aryl group attached to the parent molecular moiety via a $C_1$-$C_3$ alkyl or $C_1$-$C_6$ alkyl residue. Examples include, but are not limited to, benzyl, phenethyl and the like.

The term "substituted arylalkyl," as used herein, refers to an arylalkyl group as previously defined, substituted by one, two, three or more substituents.

The terms "heteroaryl" or "heteroaromatic," as used herein, refer to a mono-, bi-, or tri-cyclic aromatic radical or ring having from five to ten ring atoms of which at least one ring atom is selected from S, O and N; zero, one, two or three ring atoms are additional heteroatoms independently selected from S, O and N; and the remaining ring atoms are carbon, wherein any N or S contained within the ring may be optionally oxidized. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the parent molecular moiety through a carbon or hetero atom.

The terms "substituted heteroaryl" or "substituted heteroaromatic," as used herein, refer to a heteroaryl or heteroaromatic group as previously defined, substituted by one, two, three, or more substituents.

The term "alicyclic," as used herein, denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, bicyclo[2.2.2]octyl and the like.

The term "substituted alicyclic," as used herein, refers to an alicyclic group as previously defined, substituted by one, two, three or more substituents.

The terms "heterocyclic," or "heterocycloalkyl" as used herein, refer to a non-aromatic ring, comprising three or more ring atoms, or a bi- or tri-cyclic fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Examples of heterocyclic groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like.

The term "substituted heterocyclic," as used herein, refers to a heterocyclic group, as previously defined, substituted by one, two, three or more substituents.

The term "heteroarylalkyl," as used herein, refers to a heteroaryl group as previously defined, attached to the parent molecular moiety via an alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by one, two, three or more substituents.

The term "alkylamino," as used herein, refers to a group having the structure —NH-alkyl.

The term "dialkylamino," as used herein, refers to a group having the structure N(alkyl)$_2$ and cyclic amines. Examples of dialkylamino include, but are not limited to, dimethylamino, diethylamino, methylethylamino, piperidino, morpholino and the like.

The term "alkoxycarbonyl," as used herein, refers to an ester group. i.e., an alkoxy group attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula COOH.

The term "carboxamide," as used herein, refers to a group of formula C(O)NH$_2$, C(O)N(H) alkyl or C(O)N (alkyl)$_2$, N(H)C(O) alkyl, N(alkyl)C(O) alkyl and the like.

The term "protecting group" (or "blocking group)" as used herein, refers to a labile chemical moiety which is known in the art to protect a hydroxyl, amino or thiol group against undesired reactions during synthetic procedures. After said synthetic procedure(s) the protecting group as described herein may be selectively removed. Protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include, but are not limited to, benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl (BOC), isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl (Alloc), acetyl (Ac), formyl, chloroacetyl, trifluoroacetyl, methoxyacetyl, phenoxyacetyl, benzoyl (Bz), methyl, t-butyl, 2,2,2-trichloroethyl, 2-trimethylsilyl ethyl, 1,1-dimethyl-2-propenyl, 3-methyl-3-butenyl, allyl, benzyl (Bn), para-methoxybenzyldiphenylmethyl, triphenylmethyl (trityl), 4,4'-dimethoxytriphenylmethyl (DMT), substituted or unsubstituted 9-(9-phenyl)xanthenyl (pixyl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like.

Preferred hydroxyl protecting groups for the present invention are DMT and substituted or unsubstituted pixyl.

Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl (BOC), 9-fluorenylmethoxycarbonyl (Fmoc), benzyloxycarbonyl, and the like.

Thiol protecting groups as known in the art are described generally in T. H. Greene and P. G. M. Wuts, *Protective Groups in Organic Synthesis,* 3rd edition, John Wiley & Sons, New York (1999). Examples of thiol protecting groups include, but are not limited to, triphenylmethyl (Trt), benzyl (Bn), and the like.

The term "protected hydroxyl group," as used herein, refers to a hydroxyl group protected with a protecting group, as previously defined.

The term "protected amino group," as used herein, refers to an amino group protected with a protecting group, as previously defined.

The term "protected thiol group," as used herein, refers to a thiol group protected with a protecting group, as previously defined.

The term "acyl," as used herein, refers to residues derived from substituted or unsubstituted acids including, but not limited to, carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates, aliphatic phosphates and the like.

The term "aprotic solvent," as used herein, refers to a solvent that is relatively inert to proton activity, i.e., not acting as a proton-donor. Examples include, but are not limited to, hydrocarbons, such as hexane, toluene and the like, halogenated hydrocarbons, such as methylene chloride, ethylene chloride, chloroform, and the like, heterocyclic compounds, such as tetrahydrofuran, N-methylpyrrolidinone and the like, and ethers such as diethyl ether, bis-methoxymethyl ether and the like. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: Organic Solvents Physical Properties and Methods of Purification, 4th ed., edited by John A. Riddick et al, Vol. II, in the Techniques of Chemistry Series, John Wiley & Sons, NY, 1986. Aprotic solvents useful in the processes of the present invention include, but are not limited to, toluene, acetonitrile, DMF, THF, dioxane, MTBE, diethylether, NMP, acetone, hydrocarbons, and haloaliphatics.

The term "protic solvent" or "protogenic solvent," as used herein, refers to a solvent that tends to provide protons, such as an alcohol, for example, methanol, ethanol, propanol, isopropanol, butanol, t-butanol, and the like. Those skilled in the art are familiar with such solvents, and will know that individual solvents or mixtures thereof may be preferred for specific compounds and reaction conditions, depending upon such factors as the solubility of reagents, reactivity of reagents and preferred temperature ranges, for example. Further discussions of protic solvents may be found in organic chemistry textbooks or in specialized monographs, for example: Organic Solvents Physical Properties and Methods of Purification, 4th ed., edited by John A. Riddick et al., Vol. II, in the Techniques of Chemistry Series, John Wiley & Sons, NY, 1986

The synthesized compounds can be separated from a reaction mixture and further purified by a method such as column chromatography, high pressure liquid chromatography, precipitation, or recrystallization. Further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Nucleobases

The nucleobases Bx may be the same or different, and include naturally occurring nucleobases adenine (A), guanine (G), thymine (T), uracil (U) and cytosine (C), as well as modified nucleobases. Modified nucleobases include heterocyclic moieties that are structurally related to the naturally-occurring nucleobases, but which have been chemically modified to impart some property to the modified nucleobase that is not possessed by naturally-occurring nucleobases. The term "nucleobase," as used herein, is intended to by synonymous with "nucleic acid base or mimetic thereof." In general, a nucleobase is any substructure that contains one or more atoms or groups of atoms capable of hydrogen bonding to a base of an oligonucleotide.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-5-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylaminocarbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

In some embodiments of the invention, oligomeric compounds, e.g. oligonucleotides, are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

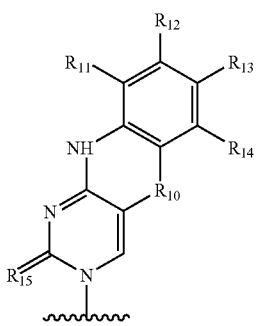

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., Nucleosides and Nucleotides, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155, 920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—(CH$_2$)$_2$—NH$_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety. Such compounds include those having the formula:

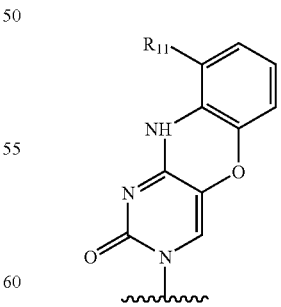

Wherein $R_{11}$ includes (CH$_3$)$_2$N—(CH$_2$)$_2$—O—; H$_2$N—(CH$_2$)$_3$—; Ph-CH$_2$—O—C(=O)—N(H)—(CH$_2$)$_3$—; H$_2$N—; Fluorenyl-CH$_2$—O—C(=O)—N(H)—(CH$_2$)$_3$—; Phthalimidyl-CH$_2$—O—C(=O)—N(H)—(CH$_2$)$_3$—; Ph-CH$_2$—O—C(=O)—N(H)—(CH$_2$)$_2$—O—; Ph-CH$_2$—

O—C(=O)—N(H)—(CH$_2$)$_3$—O—; (CH$_3$)$_2$N—N(H)—(CH$_2$)$_2$—O—; Fluorenyl-CH$_2$—O—C(=O)—N(H)—(CH$_2$)$_2$—O—; Fluorenyl-CH$_2$—O—C(=O)—N(H)—(CH$_2$)$_3$—O—; H$_2$N—(CH$_2$)$_2$—O—CH$_2$—; N$_3$—(CH$_2$)$_2$—O—CH$_2$—; H$_2$N—(CH$_2$)$_2$—O—, and NH$_2$C(=NH)NH—.

Also disclosed are tricyclic heterocyclic compounds of the formula:

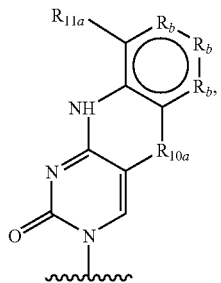

wherein:

$R_{10a}$ is O, S or N—CH$_3$; $R_{11a}$ is A(Z)$_{x1}$, wherein A is a spacer and Z independently is a label bonding group bonding group optionally bonded to a detectable label, but $R_{11a}$ is not amine, protected amine, nitro or cyano; X1 is 1, 2 or 3; and $R_b$ is independently —CH=, —N=, —C(C$_{1-8}$ alkyl)= or —C(halogen)=, but no adjacent $R_b$ are both —N=, or two adjacent $R_b$ are taken together to form a ring having the structure:

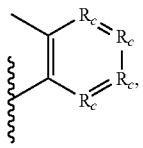

where $R_c$ is independently —CH=, —N=, —C(C$_{1-8}$ alkyl)= or —C(halogen)=, but no adjacent $R_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

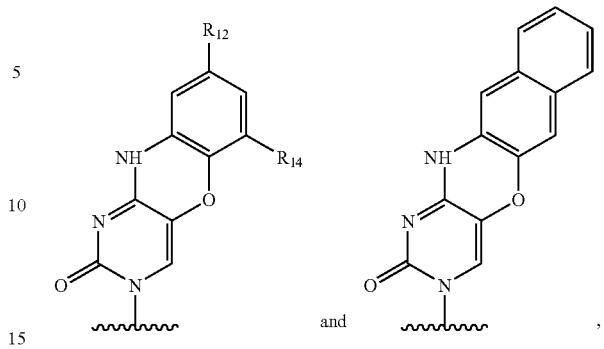

wherein $R_{14}$ is NO$_2$ or both $R_{14}$ and $R_{12}$ are independently —CH$_3$. The synthesis of these compounds is disclosed in U.S. Pat. No. 5,434,257, which issued on Jul. 18, 1995, U.S. Pat. No. 5,502,177, which issued on Mar. 26, 1996, and U.S. Pat. No. 5,646,269, which issued on Jul. 8, 1997, the contents of which are commonly assigned with this application and are incorporated herein in their entirety.

Further tricyclic heterocyclic compounds amenable to the present invention also disclosed in the "257, 177 and 269" patents include those having the formula:

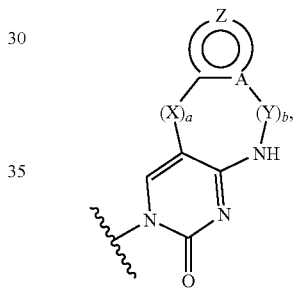

wherein a and b are independently 0 or 1 with the total of a and b being 0 or 1; A is N, C or CH; X is S, O, C=O, NH or NCH$_2$, R$^6$; Y is C=O; Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least 1 nonbridging ring carbon atom is substituted with R$^{20}$ or =O; or Z is taken together with A to form an aryl ring structure comprising 6 ring atoms wherein the aryl ring carbon atoms are unsubstituted with other than H or at least 1 nonbridging ring carbon atom is substituted with R$^6$ or =O; R$^6$ is independently H, C$_{1-6}$ alkyl, C$_{2-6}$ alkenyl, C$_{2-6}$ alkynyl, NO$_2$, N(R$^3$)$_2$, CN or halo, or an R$^6$ is taken together with an adjacent Z group R$^6$ to complete a phenyl ring; R$^{20}$ is, independently, H, C$_{1-6}$ alkyl, C$_{2-6}$ alkyl, C$_{2-6}$ alkenyl, C$_{2-6}$ alkynyl, NO$_2$, N(R$^{21}$)$_2$, CN, or halo, or an R$^{20}$ is taken together with an adjacent R$^{20}$ to complete a ring containing 5 or 6 ring atoms, and tautomers, solvates and salts thereof; R$^{21}$ is, independently, H or a protecting group; R$^3$ is a protecting group or H; and tautomers, solvates and salts thereof.

More specific examples of bases included in the "257, 177 and 269" patents are compounds of the formula:

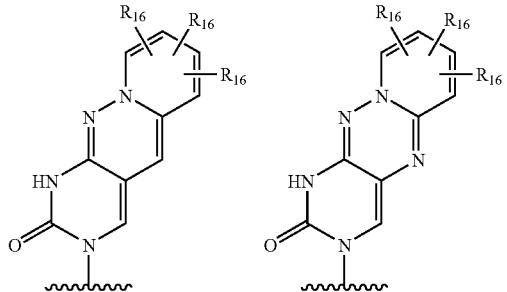

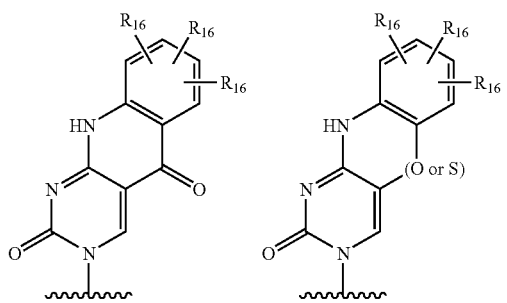

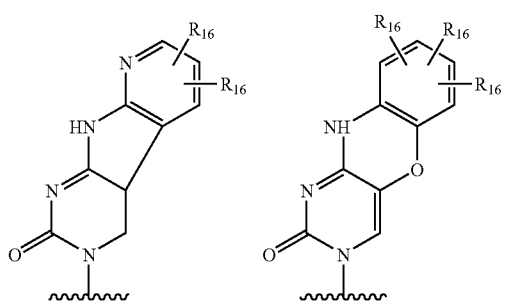

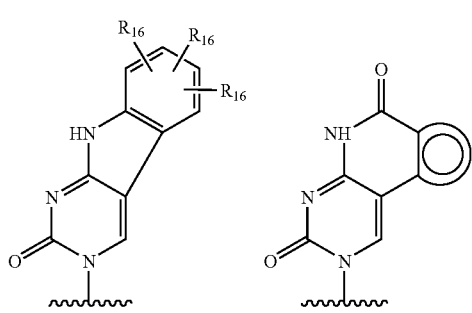

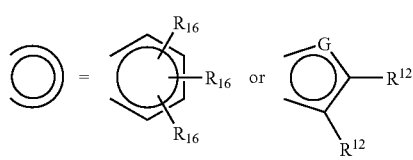

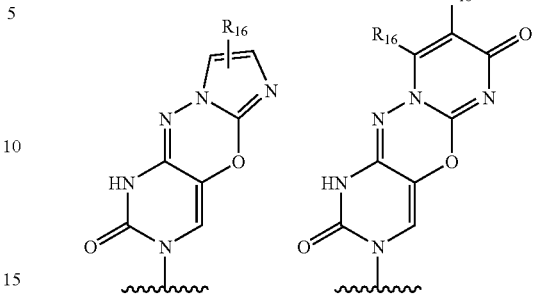

wherein each $R_{16}$, is, independently, selected from hydrogen and various substituent groups. Further polycyclic base moieties having the formula:

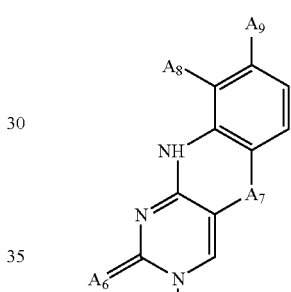

wherein: $A_6$ is O or S; $A_7$ is $CH_2$, N—$CH_3$, O or S; each $A_8$ and $A_9$ is hydrogen or one of $A_8$ and $A_9$ is hydrogen and the other of $A_8$ and $A_9$ is selected from the group consisting of:

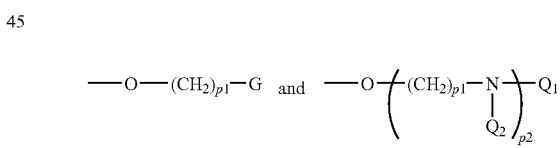

wherein: G is —CN, —$OA_{10}$, —$SA_{10}$, —N(H)$A_{10}$, —ON(H)$A_{10}$ or —C(=NH)N(H)$A_{10}$; $Q_1$ is H, —NH$A_{10}$, —C(=O)N(H)$A_{10}$, —C(=S)N(H)$A_{10}$ or —C(=NH)N(H)$A_{10}$; each $Q_2$ is, independently, H or Pg; $A_{10}$ is H, Pg, substituted or unsubstituted $C_1$-$C_{10}$ alkyl, acetyl, benzyl, —(CH$_2$)$_{p3}$NH$_2$, —(CH$_2$)$_{p3}$N(H)Pg, a D or L α-amino acid, or a peptide derived from D, L or racemic α-amino acids; Pg is a nitrogen, oxygen or thiol protecting group; each p1 is, independently, from 2 to about 6; p2 is from 1 to about 3; and p3 is from 1 to about 4; are disclosed in U.S. patent application Ser. No. 09/996,292 filed Nov. 28, 2001, which is commonly owned with the instant application, and is herein incorporated by reference.

Sugars and Sugar Substituents

The sugar moiety:

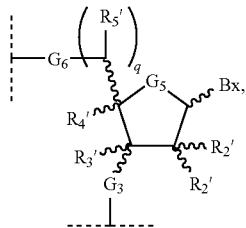

wherein each dashed line (----) indicates a point of attachment to an adjacent phosphorus atom, represents the sugar portion of a general nucleoside or nucleotide as embraced by the present invention.

Suitable 2'-substituents corresponding to $R_{12}$ include: OH, F, O-alkyl (e.g. O-methyl), S-alkyl, N-alkyl, O-alkenyl, S-alkenyl, N-alkenyl; O-alkynyl, S-alkynyl, N-alkynyl; O-alkyl-O-alkyl, wherein the alkyl, alkenyl and alkynyl may be substituted or unsubstituted $C_1$ to $C_{10}$ alkyl or $C_2$ to $C_{10}$ alkenyl or alkynyl, respectively. Particularly preferred are $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3]_2$, where g and h are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred 2'-modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504). A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples hereinbelow.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide.

Further representative substituent groups include groups of formula $I_a$ or $II_a$:

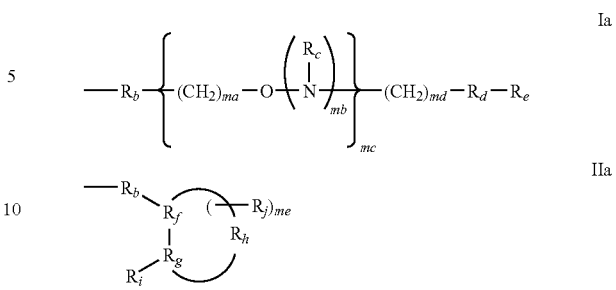

wherein: $R_b$ is O, S or NH; $R_d$ is a single bond, O or C(=O); $R_e$ is $C_1$-$C_{10}$ alkyl, $N(R_k)(R_m)$, $N(R_k)(R_n)$, N=C$(R_p)(R_q)$, N=C$(R_p)(R_r)$ or has formula $III_a$;

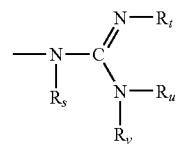

Each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl; or optionally, $R_u$ and $R_v$, together form a phthalimido moiety with the nitrogen atom to which they are attached; each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl; $R_k$ is hydrogen, a nitrogen protecting group or —$R_x$—$R_y$; $R_p$ is hydrogen, a nitrogen protecting group or —$R_x$—$R_y$; $R_x$ is a bond or a linking moiety; $R_y$ is a chemical functional group, a conjugate group or a solid support medium; each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester; or $R_m$ and $R_n$, together, are a nitrogen protecting group, are joined in a ring structure that optionally includes an additional heteroatom selected from N and O or are a chemical functional group; $R_i$ is $OR_z$, $SR_z$, or $N(R_z)_2$; each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$; $R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN; $m_a$ is 1 to about 10;

each mb is, independently, 0 or 1; mc is 0 or an integer from 1 to 10; md is an integer from 1 to 10; me is from 0, 1 or 2; and provided that when mc is 0, md is greater than 1.

Representative substituents groups of Formula I are disclosed in U.S. Pat. No. 6,172,209. Representative cyclic substituent groups of Formula II are disclosed in U.S. Pat. No. 6,271,358.

Particularly useful sugar substituent groups include O[(CH$_2$)$_g$O]$_h$CH$_3$, O(CH$_2$)$_g$OCH$_3$, O(CH$_2$)$_g$NH$_2$, O(CH$_2$)$_g$CH$_3$, O(CH$_2$)$_g$ONH$_2$, and O(CH$_2$)$_g$ON[(CH$_2$)$_g$CH$_3$)]$_2$, where g and h are from 1 to about 10.

Some particularly useful oligomeric compounds of the invention contain at least one nucleoside having one of the following substituent groups: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxy-ethoxy [2'-O—CH$_2$CH$_2$OCH$_3$, also known as 2'-O-(2-methoxyethyl) or 2'-MOE] (Martin et al., Helv. Chim. Acta, 1995, 78, 486), i.e., an alkoxyalkoxy group. A further preferred modification is 2'-dimethylaminooxy-ethoxy, i.e., a O(CH$_2$)$_2$ON(CH$_3$)$_2$ group, also known as 2'-DMAOE. Representative aminooxy substituent groups are described in co-owned U.S. patent application Ser. No. 09/344,260, filed Jun. 25, 1999, now U.S. Pat. No. 6,576,752, entitled "Aminooxy-Functionalized Oligomers"; and U.S. patent application Ser. No. 09/370,541, filed Aug. 9, 1999, now U.S. Pat. No. 6,639,062, entitled "Aminooxy-Functionalized Oligomers and Methods for Making Same;" hereby incorporated by reference in their entirety.

Other particularly advantageous 2'-modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula III and IV are disclosed in co-owned U.S. patent application Ser. No. 09/349,040, now U.S. Pat. No. 6,593,466 entitled "Functionalized Oligomers", filed Jul. 7, 1999, issue fee paid on Oct. 23, 2002.

Representative acetamido substituent groups are disclosed in U.S. Pat. No. 6,147,200 which is hereby incorporated by reference in its entirety. Representative dimethylaminoethyloxyethyl substituent groups are disclosed in International Patent Application PCT/US99/17895, entitled "2'-O-Dimethylamino-ethyloxyethyl-Modified Oligonucleotides", filed Aug. 6, 1999, hereby incorporated by reference in its entirety. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

While the present invention may be adapted to produce oligonucleotides for any desired end use (e.g. as probes for us in the polymerase chain reaction), one preferred use of the oligonucleotides is in antisense therapeutics. One mode of action that is often employed in antisense therapeutics is the so-called RNAse H mechanism, whereby a strand of DNA is introduced into a cell, where the DNA hybridizes to a strand of RNA. The DNA-RNA hybrid is recognized by an endonuclease, RNAse H, which cleaves the RNA strand. In normal cases, the RNA strand is messenger RNA (mRNA), which, after it has been cleaved, cannot be translated into the corresponding peptide or protein sequence in the ribosomes. In this way, DNA may be employed as an agent for modulating the expression of certain genes.

It has been found that by incorporating short stretches of DNA into an oligonucleotide, the RNAse H mechanism can be effectively used to modulate expression of target peptides or proteins. In some embodiments of the invention, an oligonucleotide incorporating a stretch of DNA and a stretch of RNA or 2'-modified RNA can be used to effectively modulate gene expression. In preferred embodiments, the oligonucleotide comprises a stretch of DNA flanked by two stretches of 2'-modified RNA. Preferred 2'-modifications include 2'-MOE as described herein.

The ribosyl sugar moiety has also been extensively studied to evaluate the effect its modification has on the properties of oligonucleotides relative to unmodified oligonucleotides. The 2'-position of the sugar moiety is one of the most studied sites for modification. Certain 2'-substituent groups have been shown to increase the lipohpilicity and enhance properties such as binding affinity to target RNA, chemical stability and nuclease resistance of oligonucleotides. Many of the modifications at the 2'-position that show enhanced binding affinity also force the sugar ring into the C$_3$-endo conformation.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry*, 1996, 35, 8489-8494).

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of a DNA:RNA hybrid is central to antisense therapies as the mechanism requires the binding of a modified DNA strand to a mRNA strand. To effectively inhibit the mRNA, the antisense DNA should have a very high binding affinity with the mRNA. Otherwise the desired interaction between the DNA and target mRNA strand will occur infrequently, thereby decreasing the efficacy of the antisense oligonucleotide.

Various synthetic modifications have been proposed to increase nuclease resistance, or to enhance the affinity of the antisense strand for its target mRNA (Crooke et al., *Med. Res. Rev.*, 1996, 16, 319-344; De Mesmaeker et al., *Acc. Chem. Res.*, 1995, 28, 366-374). A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2=hydroxyl in RNA biases the sugar toward a C3=endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2=hydroxyl groups of RNA can form a network of water mediated hydrogen bonds that help stabilize the RNA duplex (Egli et al., *Biochemistry*, 1996, 35, 8489-8494).

DNA:RNA hybrid duplexes, however, are usually less stable than pure RNA:RNA duplexes and, depending on their sequence, may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of a DNA:RNA hybrid a significant aspect of antisense therapies, as the proposed mechanism requires the binding of a modified DNA strand to a mRNA strand. Ideally, the antisense DNA should have a very high binding affinity with the mRNA. Otherwise, the desired interaction between the DNA and target mRNA strand will occur infrequently, thereby decreasing the efficacy of the antisense oligonucleotide.

One synthetic 2'-modification that imparts increased nuclease resistance and a very high binding affinity to nucleotides is the 2=-methoxyethoxy (MOE, 2'-OCH$_2$CH$_2$OCH$_3$) side chain (Baker et al., *J. Biol. Chem.*, 1997, 272, 11944-12000; Freier et al., *Nucleic Acids Res.*, 1997, 25, 4429-4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429-4443). 2=-O-Methoxyethyl-substituted oligonucleotides also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, they display improved RNA affinity and higher nuclease resistance. Chimeric oligonucleotides with 2=-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

LNAs (oligonucleotides wherein the 2' and 4' positions are connected by a bridge) also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

LNAs in which the 2'-hydroxyl group is linked to the 4' carbon atom of the sugar ring thereby forming a 2'-C,4'-C-oxymethylene linkage thereby forming a bicyclic sugar moiety. The linkage may be a methelyne (—CH$_2$—)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Other preferred bridge groups include the 2'-deoxy-2'-CH$_2$OCH$_2$-4' bridge.

Alternative Internucleoside Linkers

In addition to phosphate diester and phosphorothioate diester linkages, other linkers are known in the art. While the primary concern of the present invention has to do with phosphate diester and phosphorothioate diester oligonucleotides, chimeric compounds having more than one type of linkage, as well as oligomers having non-phosphate/phosphorothioate diester linkages as described in further detail below, are also contemplated in whole or in part within the context of the present invention.

Exemplary non-phosphate/phosphorothioate diester linkages contemplated within the skill of the art include: phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates. Additional linkages include: thiodiester (—O—C(O)—S—), thionocarbamate (—O—C(O)(NJ)-S—), siloxane (—O—Si(J)$_2$-O—), carbamate (—O—C(O)—NH— and —NH—C(O)—O—), sulfamate (—O—S(O)(O)—N— and —N—S(O)(O)—N—, morpholino sulfamide (—O—S(O)(N(morpholino)-), sulfonamide (—O—SO$_2$—NH—), sulfide (—CH$_2$—S—CH$_2$—), sulfonate (—O—SO$_2$—CH$_2$—), N,N'-dimethylhydrazine (—CH$_2$—N(CH$_3$)—N(CH$_3$)—), thioformacetal (—S—CH$_2$—O—), formacetal (—O—CH$_2$—O—), thioketal (—S—C(J)$_2$-O—), ketal (—O—C(J)$_2$-O—), amine (—NH—CH$_2$—CH$_2$—), hydroxylamine (—CH$_2$—N(J)-O—), hydroxylimine (—CH=N—O—), and hydrazinyl (—CH$_2$—N(H)—N(H)—).

In each of the foregoing substructures relating to internucleoside linkages, J denotes a substituent group which is commonly hydrogen or an alkyl group or a more complicated group that varies from one type of linkage to another.

In addition to linking groups as described above that involve the modification or substitution of the —O—P—O— atoms of a naturally occurring linkage, included within the scope of the present invention are linking groups that include modification of the 5'-methylene group as well as one or more of the —O—P—O— atoms. Linkages of this type are well documented in the prior art and include without limitation the following: amides (—CH$_2$—CH$_2$—N(H)—C(O)) and —CH$_2$—O—N=CH—; and alkylphosphorus (—C(J)$_2$-P(=O)(OJ)-C(J)$_2$-C(J)$_2$-). J is as described above.

Oligonucleotide Synthesis

Oligonucleotides are generally prepared, as described above, on a solid support medium, e.g. a solid support medium. In general a first synthon (e.g. a monomer, such as a nucleoside) is first attached to a solid support medium, and the oligonucleotide is then synthesized by sequentially coupling monomers to the solid support-bound synthon. This iterative elongation eventually results in a final oligomeric compound or other polymer such as a polypeptide. Suitable solid support media can be soluble or insoluble, or may possess variable solubility in different solvents to allow the growing solid support bound polymer to be either in or out of solution as desired. Traditional support media such as solid support media are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489-510).

The term support medium is intended to include all forms of support known to the art skilled for the synthesis of oligomeric compounds and related compounds such as peptides. Some representative support medium that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support medium, polyethylene glycol PEG's (see Bonora et al., Organic Process Research & Development, 2000, 4, 225-231).

In particular embodiments of the invention, SM is a solid support medium.

In particular embodiments of the invention, SM is a semi-solid support medium such as polyethylene glycol, chiotosan, etc. One advantage to chitosan as a support medium is that it naturally possesses a terminal amino group, which is convenient for linking to a terminal acid group as described in reference to formula CC, above.

Further support media amenable to the present invention include without limitation PEPS support a polyethylene (PE) film with pendant long-chain polystyrene (PS) grafts (molecular weight on the order of $10^6$, (see Berg, et al., J. Am. Chem. Soc., 1989, 111, 8024 and International Patent Application WO 90/02749)). The loading capacity of the film is as high as that of a beaded matrix with the additional flexibility to accommodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell-plates have not indicated any limitations of the synthetic efficacy.

Further support media amenable to the present invention include without limitation particles based upon copolymers of dimethylacrylamide cross-linked with N,N'-bisacryloyl-ethylenediamine, including a known amount of N-tertbutoxy-carbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., J. Am. Chem. Soc., 1975, 97, 6584, Bioorg. Chem. 1979, 8, 351, and J. C. S. Perkin I 538 (1981)).

Further support media amenable to the present invention include without limitation a composite of a resin and another material that is also substantially inert to the organic synthesis reaction conditions employed. One exemplary composite (see Scott, et al., *J. Chrom. Sci.,* 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in Peptides 1974, Y. Wolman, Ed., Wiley and Sons, New York, 1975, pp. 113-116). Contiguous solid support media other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis. (Geysen, et al., *Proc. Natl. Acad. Sci. USA,* 1984, 81, 3998). A "tea bag" containing traditionally-used polymer beads. (Houghten, *Proc. Natl. Acad. Sci. USA,* 1985, 82, 5131). Simultaneous use of two different supports with different densities (Tregear, Chemistry and Biology of Peptides, J. Meienhofer, ed., Ann Arbor Sci. Publ., Ann Arbor, 1972 pp. 175-178). Combining of reaction vessels via a manifold (Gorman, *Anal. Biochem.,* 1984, 136, 397). Multicolumn solid-phase synthesis (e.g., Krchnak, et al, *Int. J. Peptide Protein Res.,* 1989, 33, 209), and Holm and Meldal, in "Proceedings of the 20th European Peptide Symposium", G. Jung and E. Bayer, eds., Walter de Gruyter & Co., Berlin, 1989 pp. 208-210). Cellulose paper (Eichler, et al., *Collect. Czech. Chem. Commun.,* 1989, 54, 1746). Support mediated synthesis of peptides have also been reported (see, *Synthetic Peptides: A User's Guide,* Gregory A. Grant, Ed. Oxford University Press 1992; U.S. Pat. Nos. 4,415,732; 4,458,066; 4,500,707; 4,668,777; 4,973,679; 5,132,418; 4,725,677 and Re 34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Köster U.S. Pat. Nos. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

In general, the phosphorus protecting group (pg) is an alkoxy or alkylthio group or O or S having a β-eliminable group of the formula $-CH_2CH_2-G_w$, wherein $G_w$ is an electron-withdrawing group. Suitable examples of pg that are amenable to use in connection with the present invention include those set forth in the Caruthers U.S. Pat. Nos. 4,415,732; 4,458,066; 4,500,707; 4,668,777; 4,973,679; and 5,132,418; and Köster U.S. Pat. Nos. 4,725,677 and Re. 34,069. In general the alkyl or cyanoethyl withdrawing groups are preferred, as commercially available phosphoramidites generally incorporate either the methyl or cyanoethyl phosphorus protecting group.

The method for removal of pg depends upon the specific pg to be removed. The β-eliminable groups, such as those disclosed in the Köster et al. patents, are generally removed in a weak base solution, whereby an acidic β-hydrogen is extracted and the $-CH_2CH_2-G_w$ group is eliminated by rearrangement to form the corresponding acrylo-compound $CH_2=CH-G_w$. In contrast, an alkyl group is generally removed by nucleophilic attack on the α-carbon of the alkyl group. Such PGs are described in the Caruthers et al. patents, as cited herein.

The person skilled in the art will recognize that oxidation of P(III) to P(V) can be carried out by a variety of reagents. Furthermore, the person skilled in the art will recognize that the P(V) species can exist as phosphate triesters, phosphorothioate diesters, or phosphorodithioate diesters. Each type of P(V) linkage has uses and advantages, as described herein. Thus, the term "oxidizing agent" should be understood broadly as being any reagent capable of transforming a P(III) species (e.g. a phosphite) into a P(V) species. Thus the term "oxidizing agent" includes "sulfurizing agent," which is also considered to have the same meaning as "thiation reagent." Oxidation, unless otherwise modified, indicates introduction of oxygen or sulfur, with a concomitant increase in P oxidation state from III to V. Where it is important to indicate that an oxidizing agent introduces an oxygen into a P(III) species to make a P(V) species, the oxidizing agent will be referred to herein is "an oxygen-introducing oxidizing reagent."

Oxidizing reagents for making phosphate diester linkages (i.e. oxygen-introducing oxidizing reagents) under the phosphoramidite protocol have been described by e.g. Caruthers et al. and Köster et al., as cited herein. Examples of sulfurization reagents which have been used to synthesize oligonucleotides containing phosphorothioate bonds include elemental sulfur, dibenzoyltetrasulfide, 3-H-1,2-benzidithiol-3-one 1,1-dioxide (also known as Beaucage reagent), tetraethylthiuram disulfide (TETD), and bis(O,O-diisopropoxy phosphinothioyl) disulfide (known as Stec reagent). Oxidizing reagents for making phosphorothioate diester linkages include phenylacetyldisulfide (PADS), as described by Cole et al. in U.S. Pat. No. 6,242,591. In some embodiments of the invention, the phosphorothioate diester and phosphate diester linkages may alternate between sugar subunits. In other embodiments of the present invention, phosphorothioate linkages alone may be employed. In some embodiments, the thiation reagent may be a dithiuram disulfides. See U.S. Pat. No. 5,166,387 for disclosure of some suitable dithiuram disulfides. It has been surprisingly found that one dithiuram disulfide may be used together with a standard capping reagent, so that capping and oxidation may be conducted in the same step. This is in contrast to standard oxidative reagents, such as Beaucage reagent, which require that capping and oxidation take place in separate steps, generally including a column wash between steps.

The 5'-protecting group bg or T' is a protecting group that is orthogonal to the protecting groups used to protect the nucleobases, and is also orthogonal, where appropriate to 2'-O-protecting groups, as well as to the 3'-linker to the solid support medium. In some embodiments of the invention, the 5'-protecting group is acid labile. In some embodiments according to the invention, the 5'-protecting group is selected from an optionally substituted trityl group and an optionally substituted pixyl group. In some embodiments, the pixyl group is substituted with one or more substituents selected from alkyl, alkoxy, halo, alkenyl and alkynyl groups. In some embodiments, the trityl groups are substituted with from about 1 to about 3 alkoxy groups, specifically about 1 to about 3 methoxy groups. In particular embodiments of the invention, the trityl groups are substituted with 1 or 2 methoxy groups at the 4- and (if applicable) 4'-positions. A particularly acceptable trityl group is 4,4'-dimethoxytrityl (DMT or DMTr).

In the context of the present invention, the term "reagent push" has the meaning of a volume of solvent that is substantially free of any active compound (i.e. reagent, activator, by-product, or other substance other than solvent), which volume of solvent is introduced to the column for the purpose, and with the effect, of pushing a reagent solution onto and through the column ahead of a subsequent reagent solution. A reagent push need not be an entire column volume, although in some cases it may include one or more column volumes. In some embodiments, a reagent push comprises at least the minimum volume necessary to substantially clear reagent, by-products and/or activator from a cross-section of the column immediately ahead of the front formed by the reagent solution used for the immediately subsequent synthetic step. An active compound, whether a reagent, by-product or activator, is considered substantially cleared if the concentration of the compound in a cross-section of the column at which the following reagent solution front is located, is low enough that it does not substantially affect the activity of the following reagent solution. The person skilled in the art will recognize that this the volume of solvent required for a "reagent push" will vary depending upon the solvent, the solubility in the solvent of the reagents, activators, by-products, etc., that are on the column, the amounts of reagents, activators, by-products, etc. that are to be cleared from the column, etc. It is considered within the skill of the artisan to select an appropriate volume for each reagent push, especially with an eye toward the Examples, below.

As used herein, unless "column wash" is otherwise modified, it has the same meaning as "reagent push." In some embodiments of the invention, column wash may imply that at least one column volume is permitted to pass through the column before the subsequent reagent solution is applied to the column. Where a column volume (CV) of the column wash is specified, this indicates that a volume of solvent equivalent to the interior volume of the unpacked column is used for the column wash.

In the context of the present invention, a wash solvent is a solvent containing substantially no active compound that is applied to a column between synthetic steps. A "wash step" is a step in which a wash solvent is applied to the column. Both "reagent push" and "column wash" are included within this definition of "wash step".

A wash solvent may be a pure chemical compound or a mixture of chemical compounds, the solvent being capable of dissolving an active compound.

In some embodiments according to the present invention, a wash solvent used in one of the wash steps may comprise some percentage of acetonitrile, not to exceed 50% v/v.

The sequence of capping and oxidation steps may be reversed, if desired. That is, capping may precede or follow oxidation. Also, with selection of a suitable thiation reagent, the oxidation and capping steps may be combined into a single step. For example, it has been surprisingly found that capping with acetic anhydride may be conducted in the presence of N,N'-dimethyldithiuram disulfide.

Various solvents may be used in the oxidation reaction. Suitable solvents are identified in the Caruthers et al. and Köster et al. patents, cited herein. The Cole et al. patent describes acetonitrile as a solvent for phenylacetyldisulfide. Other suitable solvents include toluene, xanthenes, dichloromethane, etc.

Reagents for cleaving an oligonucleotide from a support are set forth, for example, in the Caruthers et al. and Köster et al. patents, as cited herein. It is considered good practice to cleave oligonucleotide containing thymidine (T) nucleotides in the presence of an alkylated amine, such as triethylamine, when the phosphorus protecting group is $O-CH_2CH_2CN$, because this is now known to avoid the creation if cyanoethylated thymidine nucleotides (CNET). Avoidance of CNET adducts is described in general in U.S. Pat. No. 6,465,628, which is incorporated herein by reference, and especially the Examples in columns 20-30, which are specifically incorporated by reference. In other preferred embodiments, one may remove phosphorus protecting groups in the presence of an alkylated amine, which effectively removes the protecting group under conditions that will not cause CNET formation (e.g. room temperature). This phosphorus deprotection step may then be followed by a wash step. The phosphorus deprotection, or optional wash step, is then followed by the cleaving step, e.g. removal of exocyclic amine protecting groups (e.g. isobutyryl and/or benzoyl groups) and cleavage of the oligonucleotide from the support under standard conditions (strong base and heat).

The oligonucleotide may be worked up by standard procedures known in the art, for example by size exclusion chromatography, high performance liquid chromatography (e.g. reverse-phase HPLC), differential precipitation, etc. In some embodiments according to the present invention, the oligonucleotide is cleaved from a solid support medium while the 5'-OH protecting group is still on the ultimate nucleoside. This so-called DMT-on (or trityl-on) oligonucleotide is then subjected to chromatography, after which the DMT group is removed by treatment in an organic acid, after which the oligonucleotide is de-salted and further purified to form a final product. This procedure will also work well where the acid-labile protecting group is pixyl or substituted pixyl, as the pixyl-on oligonucleotide is conveniently separated from capped shortmer (failure) sequences by reverse phase HPLC.

The 5'-hydroxyl protecting groups may be any groups that are selectively removed under suitable conditions. In particular, the 4,4'-dimethoxytriphenylmethyl (DMT) group is a favored group for protecting at the 5'-position, because it is readily cleaved under acidic conditions (e.g. in the presence of dichloracetic acid (DCA), trichloroacetic acid (TCA), or acetic acid. Removal of DMT from the support-bound oligonucleotide is generally performed with DCA (e.g. about 3 to about 10 percent DCA (v/v) in a suitable solvent. Removal of oligonucleotide after cleavage from the support is generally performed with acetic acid. Where the 5-hydroxyl protecting group is pixyl or substituted pixyl, an acid with a higher pKa than DCA may be used, as pixyl groups are generally labile to higher pKa acids than are trityl groups. In some embodiments, pixyl or substituted pixyl groups may be removed with acetic acid.

As described herein, oligonucleotides can be prepared as chimeras with other oligomeric moieties. In the context of this invention, the term "oligomeric compound" refers to a polymeric structure capable of hybridizing a region of a nucleic acid molecule, and an "oligomeric moiety" a portion of such an oligomeric compound. Oligomeric compounds include oligonucleotides, oligonucleosides, oligonucleotide analogs, modified oligonucleotides and oligonucleotide mimetics. Oligomeric compounds can be linear or circular, and may include branching. They can be single stranded or double stranded, and when double stranded, may include overhangs. In general an oligomeric compound comprises a backbone of linked monomeric subunits where each linked monomeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras. As is known in the art, a nucleoside is a base-sugar combination. The base portion of the nucleoside is normally a heterocyclic base moiety. The two most common classes of such heterocyclic bases are purines and pyrimidines. In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Synthetic schemes for the synthesis of the substitute internucleoside linkages described above are disclosed in: U.S. Pat. Nos. 5,466,677; 5,034,506; 5,124,047; 5,278,302; 5,321,131; 5,519,126; 4,469,863; 5,455,233; 5,214,134; 5,470,967; 5,434,257. Additional background information relating to internucleoside linkages can be found in: WO 91/08213; WO 90/15065; WO 91/15500; WO 92/20822; WO 92/20823; WO 91/15500; WO 89/12060; EP 216860; PCT/US 92/64294; PCT/US 90/03138; PCT/US 91/06855; PCT/US 92/03385; PCT/US 91/03680; U.S. application Ser. Nos. 07/990,848; 07,892,902; now U.S. Pat. No. 5,817,791; Ser. Nos. 07/806,710; 07/763,130; now U.S. Pat. No. 5,596,086; Ser. No. 07/690,786; now U.S. Pat. No. 5,264,562; Stirchak, E. P., et al., Nucleic Acid Res., 1989, 17, 6129-6141; Hewitt, J. M., et al., 1992, 11, 1661-1666; Sood, A., et al., J. Am. Chem. Soc., 1990, 112, 9000-9001; Vaseur, J. J. et al., J. Amer. Chem. Soc., 1992, 114, 4006-4007; Musichi, B., et al., J. Org. Chem., 1990, 55, 4231-4233; Reynolds, R. C., et al., J. Org. Chem., 1992, 57, 2983-2985; Mertes, M. P., et al., J. Med. Chem., 1969, 12, 154-157; Mungall, W. S., et al., J. Org. Chem., 1977, 42, 703-706; Stirchak, E. P., et al., J. Org. Chem., 1987, 52, 4202-4206; Coull, J. M., et al., Tet. Lett., 1987, 28, 745; and Wang, H., et al., Tet. Lett., 1991, 32, 7385-7388.

Phosphoramidites used in the synthesis of oligonucleotides are available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.). These commercial sources sell high purity phosphoramidites generally having a purity of better than 98%. Those not offering an across the board purity for all amidites sold will in most cases include an assay with each lot purchased giving at least the purity of the particular phosphoramidite purchased. Commercially available phosphoramidites are prepared for the most part for automated DNA synthesis and as such are prepared for immediate use for synthesizing desired sequences of oligonucleotides. Phosphoramidites may be prepared by methods disclosed by e.g. Caruthers et al. (U.S. Pat. Nos. 4,415,732; 4,458,066; 4,500,707; 4,668,777; 4,973,679; and 5,132,418) and Köster et al. (U.S. Pat. No. RE 34,069).

Double stranded oligonucleotides, such as double-stranded RNA, may be manufactured according to methods according to the present invention, as described herein. In the case of RNA synthesis, it is necessary to protect the 2'-OH of the amidite reagent with a suitable removable protecting groups. Suitable protecting groups for 2'-OH are described in U.S. Pat. Nos. 6,008,400, 6,111,086 and 5,889,136. A particularly suitable 2'-protecting group for RNA synthesis is the ACE protecting group as described in U.S. Pat. No. 6,111,086. In some embodiments, it is considered advantageous to use a different 5'-protecting group for amidites used in RNA synthesis. Suitable 5'-protecting groups are set forth in U.S. Pat. No. 6,008,400. A particularly suitable 5'-protecting group is the trimethylsilyloxy (TMSO) group as taught in U.S. Pat. No. 6,008,400. See especially example 1, columns 10-13. The separate strands of the double stranded RNA may be separately synthesized and then annealed to form the double stranded (duplex) oligonucleotide.

Oligonucleotide Use

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly preferred antisense compounds are represented by DNA or RNA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). One having skill in the art, once armed with the empirically-derived preferred antisense compounds illustrated herein will be able, without undue experimentation, to identify further preferred antisense compounds.

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention. Additional preferred antisense compounds may be identified by one having ordinary skill.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

RNAse H-Dependent Antisense

One method for inhibiting specific gene expression involves using oligonucleotides or oligonucleotide analogs as "antisense" agents. Antisense technology involves directing oligonucleotides, or analogs thereof, to a specific, target messenger RNA (mRNA) sequence. The interaction of exogenous "antisense" molecules and endogenous mRNA modulates transcription by a variety of pathways. Such pathways include transcription arrest, RNAse H recruitment, and RNAi (e.g. siRNA). Antisense technology permits modulation of specific protein activity in a relatively predictable manner.

EXAMPLES

The present invention may be further understood with reference to the following, no-limiting, illustrative examples, which may be carried out by methods generally described hereinabove.

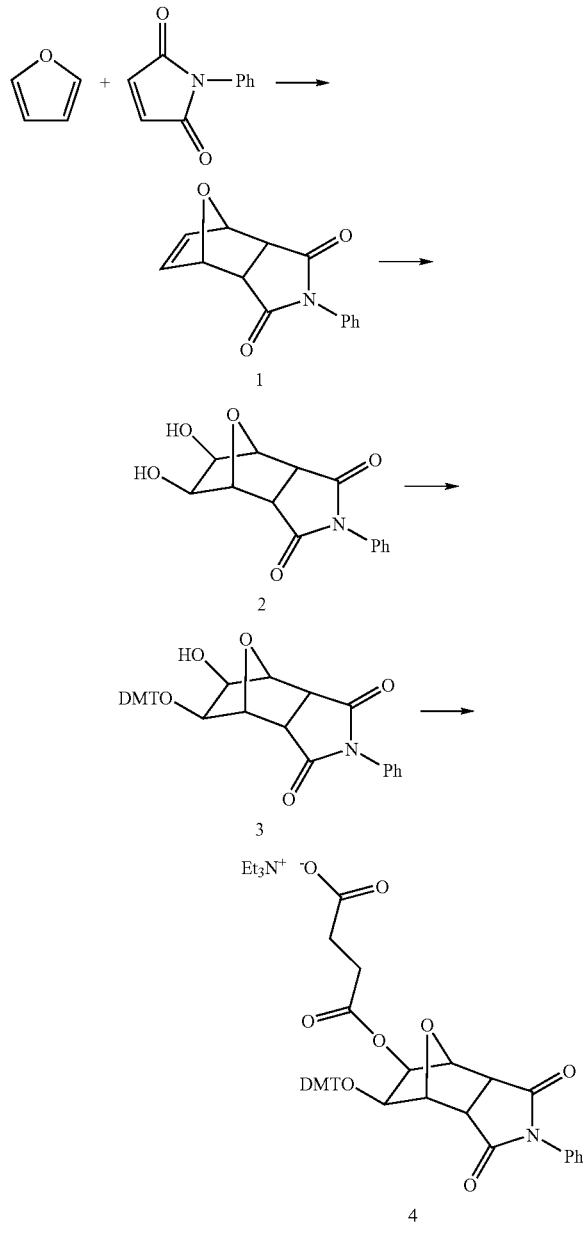

Experiment 1

Diels-Alder reaction between furan and N-phenylmaleimide to give adduct 1: N-Phenylmaleimide (500 g; 2.887 mole) was taken in acetonitrile (1600 mL) and furan (500 mL) was added and heated under reflux using a heating mantle and ice-water cooling condenser in a 5 L three-necked round bottomed flask provided with magnetic stirring. After refluxing for 5 hours, the reaction mixture was analyzed by HPLC for absence of starting material (viz N-phenyl maleimide). Then the reaction mixture was cooled to room temperature when colorless solid precipitates out. The material was filtered, washed with acetonitrile (500 mL). The filtrate solution was concentrated to afford more of product which was also filtered and washed with acetonitrile (300 mL). The solid 1 was dried under high vacuum at room temperature overnight. Yield: 541 g (78%). $^1$H NMR (DMSO-d6): 3.055 (s, 2H), 5.223 (s, 2H), 6.580 (s, 2H), 7-18-7.58 (m, 5H).

Experiment 2

Osmium tetroxide catalyst solution: The content of a 1 g sealed vial of osmium tetroxide was dissolved in 200 mL of purified t-butyl alcohol. The pale green solution was treated with 3-5 drops of 30% hydrogen peroxide and allowed to remain at room temperature for 1 day. If the solution became dark, the dropwise addition of 30% hydrogen peroxide was repeated until the pale green color persisted. This solution is stable for at least one year at room temperature. Each mL contains $2 \times 10^{-5}$ mole of osmium tetroxide.

Experiment 3 cis-Dihydroxylation of Diels-Alder adduct to give diol 2: The olefin 1 obtained from above Diels-Alder reaction (225 g, 0.934 mole) was taken in a 5 L three-necked flask fitted with a mechanical stirrer, reflux condenser with ice-water cooling and a heating mantle. Acetone (2500 mL) was added and stirred. A 30% Hydrogen peroxide solution (500 mL) was added followed by osmium tetroxide solution prepared earlier (180 mL). Warning: For larger scales the reaction could be exothermic!! Slow addition (1-2 hour) of osmium tetroxide solution is recommended. Gentle refluxing of reaction mixture with stirring was maintained for 7-8 h. During the period, reaction color changed from brown to pale brown to colorless and solid started crashing out. Vigorous stirring was maintained through out the period. The reaction mixture was analyzed by HPLC for absence of starting material. The reaction mixture was cooled to room temperature and filtered. The solid 2 was washed with ether (2000 mL) and dried in vacuum oven at room temperature overnight. The acetone filtrate solution was concentrated and ether (1000 mL) was added when solid precipitated out which was filtered, washed with ether (300 ml) and dried in over at 45 deg C. for two days. Yield of 2=179 g (first crop)+32 g (second crop)=211 g (82%). $^1$H NMR (DMSO-d6): 3.14 (s, 2H), 3.88 (d, 2H), 4.39 (s, 2H), 5.1 (d, 2H), 7-18-7.58 (m, 5H).

Experiment 4

Mono protection of diol with DMT chloride to form 3: The dihydroxy compound 3 (FW 275; 275 g; 1 mole) was taken in a 5 L round-bottomed flask and co-evaporated with anhydrous pyridine (1200 mL). This step was repeated one more time to render the diol anhydrous. Pyridine (3000 mL) was added and stirred using magnetic stirrer at room temperature. Dimethoxytrityl chloride (FW 338.82; 508.2 g, 1.5 equivalents) was slowly added as solid over a period of 2 hours. Solution was stirred overnight. Tlc indicated almost disappearance of starting material. All volatiles were removed under vacuum using rotavap. Toluene (2000 mL) was added and rotavaped. This step was repeated one more time. The remaining crude material was purified by flash silica gel chromatography using hexane, 20% ethyl acetate-hexane, then 40% ethyl acetate-hexane and finally 100% ethyl acetate. 1% Triethylamine was used through out purification. Yield of 3: 398 g (71%).

Experiment 5

Succinylation of DMT protected compound 3: DMT protected hydroxy compound 3 (FW 578; 49.13 g; 85 mmole) was dissolved in a mixture ethyl acetate:methylene chloride (600:66=666 mL). Triethyl amine (FW 101.19; 51.61 g; 71 mL; 0.51 mole; 6 equivalent with respect to starting DMT compound) was added and stirred magnetically at room temperature. To this clear solution, succinic anhydride (FW 100.07; 34.02 g; 0.34 mole, 4 equivalents with respect to starting DMT compound) was added as solid all at once. Stirring was continued overnight. TLC indicated disappearance of starting material. If starting material is seen, more of succinic anhydride is added till completion of reaction. The reaction mixture was diluted with ethyl acetate (300 mL) and washed with water (2×200 mL), brine (120 mL) and dried with magnesium sulfate. If the product is colored, the material is passed through a short pad of silica gel eluting with methylene chloride and then 5% methanol:95% methylene chloride to afford the product as a colorless product. Yield of 4: 60.5 g (91%).

Experiment 6

Synthesis of substituted pixyl alcohol: To a stirred mixture of 4',4'-dimethyldiphenylether (200 g; 1.01 mole), p-methybenzoic acid (154 g; 1.13 mole) and anhydrous zinc chloride (400 g; 2.94 mole) was added phosphorousoxy trichloride (300 ml; 3.27 mole) slowly using an addition funnel. The reaction mixture was then slowly heated to 95° C. when the reaction starts and monitored by tlc. After the reaction is complete, ethyl acetate (500 ml) was added, followed by water (200 ml) slowly. An additional amount of water (2500 ml) was added at a faster rate. Stirred overnight at room temperature when solid comes out. It was filtered and recrystallized from methanol to afford the substituted pixyl alcohol product.

Experiment 7

Synthesis of substituted pixyl chloride: To a stirred solution of substituted pixyl alcohol (310 g; 0.982 mole) in dichloromethane (1000 ml) was added thionyl chloride (102 ml; 1.1 mole) slowly with cooling. The reaction was monitored by tlc. When complete, the reaction was concentrated, toluene added followed by hexane to afford the desired product as colorless solid.

Experiment 8

Mono protection of diol 2 with substituted pixyl chloride to form the substituted pixyl analog of 3 (3'): The dihydroxy compound (FW 275; 0.1 mole) was taken in a round-bottomed flask and co-evaporated with anhydrous pyridine. This step was repeated one more time to render the diol anhydrous. Pyridine (200 mL) was added and stirred using magnetic stirrer at room temperature. Trimethyl substituted pixyl chloride (1.5 equivalents) was slowly added as solid over a period of 30 minutes. Solution was stirred overnight. Tlc indicated almost disappearance of starting material. All volatiles were removed under vacuum using rotavap. Toluene was added and rotavaped. This step was repeated one more time. The remaining crude material was purified by flash silica gel chromatography using hexane, 20% ethyl acetate-hexane, then 40% ethyl acetate-hexane and finally 100% ethyl acetate. 1% Triethylamine was used through out purification. The product 3' was obtained as a colorless solid.

Experiment 9

Succinylation of substituted pixyl protected compound 3' to form the substituted pixyl analog of 4 (4'): Substituted pixyl protected hydroxy compound 3' (85 mmole) was dissolved in a mixture ethyl acetate:methylene chloride (600:66=666 mL). Triethyl amine (FW 101.19; 51.61 g; 71 mL; 0.51 mole; 6 equivalent with respect to starting compound) was added and stirred magnetically at room temperature. To this clear solution, succinic anhydride (FW 100.07; 34.02 g; 0.34 mole, 4 equivalents with respect to starting compound) was added as solid all at once. Stirring was continued overnight. TLC indicated disappearance of starting material. If starting material is seen, more of succinic anhydride is added till completion of reaction. The reaction mixture was diluted with ethyl acetate (300 mL) and washed with water (2×200 mL), brine (120 mL) and dried with magnesium sulfate. If the product is colored, the material is passed through a short pad of silica gel eluting with methylene chloride and then 5% methanol:95% methylene chloride to afford the product as a colorless product. Yield of 4':93%.

Experiment 10

Loading of DMT protected succinate 4 to controlled pore glass: Loading of the succinate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=40 micromole/gram.

Experiment 11

Loading of substituted pixyl protected succinate 4' to controlled pore glass: Loading of the succinate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=38 micromole/gram.

Experiment 12

Loading of DMT protected succinate 4 to HL30 amino-derivatized primer support: Loading of the succinate molecule was performed similar to nucleoside succinate using HBTU as activator and Hunig's base in acetonitrile as solvent. The unreacted sites were capped with acetic anhydride

Experiment 13

Loading of substituted pixyl protected succinate 4' to HL30 amino-derivatized primer support: Loading of the succinate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=93 micromole/gram.

Experiment 14

Loading of DMT protected succinate 4 to OligoPrep: Loading of the succinate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=244 micromole/gram.

Experiment 15

Loading of substituted pixyl protected succinate 4' to OligoPrep: Loading of the succinate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=253 micromole/gram.

Experiment 16

Loading of DMT protected succinate 4 to Nittomar 250 solid support: Loading of the succinate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=240 micromole/gram.

Experiment 17

Loading of substituted pixyl protected succinate 4' to Nittomar 250 solid support: Loading of the succinate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=250 micromole/gram.

Experiment 18

Synthesis of fully-modified 5'-d(TCC-CGC-CTG-TGA-CAT-GCA-TT)-3' (SEQ ID NO: 1) phosphorothioate 20-mer using 4: Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 19

Synthesis of fully-modified 5'-d(TCC-CGC-CTG-TGA-CAT-GCA-TT)-3' (SEQ ID NO: 1) phosphorothioate 20-mer using 4': Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 20

Synthesis of fully-modified 5'-d(GCC-CAA-GCT-GGC-ATC-CGT-CA)-3' (SEQ ID NO: 2) phosphorothioate 20-mer using 4: Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 21

Synthesis of fully-modified 5'-d(GCC-CAA-GCT-GGC-ATC-CGT-CA)-3' (SEQ ID NO: 2) phosphorothioate 20-mer using 4': Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 22

Synthesis of 5'-d(TCC-CGC-CTG-TGA-CAT-GCA-TT)-3' (SEQ ID NO: 1) DNA 20-mer using 4: Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 23

Synthesis of 5'-d(TCC-CGC-CTG-TGA-CAT-GCA-TT)-3' (SEQ ID NO: 1) DNA 20-mer using 4': Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 24

Synthesis of 5'-d(GCC-CAA-GCT-GGC-ATC-CGT-CA)-3' (SEQ ID NO: 2) DNA 20-mer using 4: Synthesis of above sequence was performed on an ABI 390Z DNA/RNA Synthesizer on a micromole scale using cyanoethyl phosphoramidites and the above prepared CPG solid support. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 25

Synthesis of 5'-d(GCC-CAA-GCT-GGC-ATC-CGT-CA)-3' (SEQ ID NO: 2) DNA 20-mer using 4': Synthesis of above sequence was performed on an ABI 390Z DNA/RNA Synthesizer on a micromole scale using cyanoethyl phosphoramidites and the above prepared CPG solid support. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 26

Synthesis of fully-modified 5'-d(TCC-CGC-CTG-TGA-CAT-GCA-TT)-3' (SEQ ID NO: 1) phosphorothioate 20-mer using 4: Synthesis of above sequence was performed on an Amersham Biosciences' Akta OligoPilot DNA/RNA Synthesizer on a 172 micromole scale using cyanoethyl phosphoramidites and the above prepared HL30 Primer solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 27

Synthesis of fully-modified 5'-d(TCC-CGC-CTG-TGA-CAT-GCA-TT)-3' (SEQ ID NO: 2) phosphorothioate 20-mer using 4': Synthesis of above sequence was performed on an Amersham Biosciences' Akta OligoPilot DNA/RNA Synthesizer on a 175 micromole scale using cyanoethyl phosphoramidites and the above prepared HL30 Primer solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 28

Synthesis of fully-modified 5'-d(GCC-CAA-GCT-GGC-ATC-CGT-CA)-3' (SEQ ID NO: 2) phosphorothioate 20-mer using 4: Synthesis of above sequence was performed on an Amersham Biosciences' Akta OligoPilot DNA/RNA Synthesizer on a 178 micromole scale using cyanoethyl phosphoramidites and the above prepared HL30 Primer solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 29

Synthesis of fully-modified 5'-d(GCC-CAA-GCT-GGC-ATC-CGT-CA)-3' (SEQ ID NO: 2) phosphorothioate 20-mer using 4': Synthesis of above sequence was performed on an Amersham Biosciences' Akta OligoPilot DNA/RNA Synthesizer on a 181 micromole scale using cyanoethyl phosphoramidites and the above prepared HL30 Primer solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 30

Synthesis of 5'-d(TCC-CGC-CTG-TGA-CAT-GCA-TT)-3' (SEQ ID NO: 1) DNA 20-mer using 4: Synthesis of above sequence was performed on an Amersham Biosciences' Akta OligoPilot DNA/RNA Synthesizer on a 184 micromole scale using cyanoethyl phosphoramidites and the above prepared HL30 Primer solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 31

Synthesis of 5'-d(TCC-CGC-CTG-TGA-CAT-GCA-TT)-3' (SEQ ID NO: 1) DNA 20-mer using 4': Synthesis of above sequence was performed on an Amersham Biosciences' Akta OligoPilot DNA/RNA Synthesizer on a 179 micromole scale using cyanoethyl phosphoramidites and the above prepared HL30 Primer solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 32

Synthesis of 5'-d(GCC-CAA-GCT-GGC-ATC-CGT-CA)-3' (SEQ ID NO: 2) DNA 20-mer using 4: Synthesis of above sequence was performed on an Amersham Biosciences' Akta OligoPilot DNA/RNA Synthesizer on a 180 micromole scale using cyanoethyl phosphoramidites and the above prepared HL30 Primer solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 33

Synthesis of 5'-d(GCC-CAA-GCT-GGC-ATC-CGT-CA)-3' (SEQ ID NO: 2) DNA 20-mer using 4': Synthesis of above sequence was performed on an Amersham Biosciences' Akta OligoPilot DNA/RNA Synthesizer on a 169 micromole scale using cyanoethyl phosphoramidites and the above prepared HL30 Primer solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 34

Synthesis of fully-modified 5'-d(TCC-CGC-CTG-TGA-CAT-GCA-TT)-3' (SEQ ID NO: 1) phosphorothioate 20-mer using 4: Synthesis of above sequence was performed on an Amersham Biosciences' Akta OligoPilot DNA/RNA Synthesizer on a 172 micromole scale using cyanoethyl phosphoramidites and the above prepared OligoPrep solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 35

Synthesis of fully-modified 5'-d(TCC-CGC-CTG-TGA-CAT-GCA-TT)-3' phosphorothioate 20-mer using 4': Synthesis of above sequence was performed on an Amersham Biosciences' Akta OligoPilot DNA/RNA Synthesizer on a 175 micromole scale using cyanoethyl phosphoramidites and the above prepared OligoPrep solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 36

Synthesis of fully-modified 5'-d(GCC-CAA-GCT-GGC-ATC-CGT-CA)-3' (SEQ ID NO: 2) phosphorothioate 20-mer using 4: Synthesis of above sequence was performed on an Amersham Biosciences' Akta OligoPilot DNA/RNA Synthesizer on a 178 micromole scale using cyanoethyl phosphoramidites and the above prepared OligoPrep solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 37

Synthesis of fully-modified 5'-d(GCC-CAA-GCT-GGC-ATC-CGT-CA)-3' (SEQ ID NO: 2) phosphorothioate 20-mer using 4': Synthesis of above sequence was performed on an Amersham Biosciences' Akta OligoPilot DNA/RNA Synthesizer on a 181 micromole scale using cyanoethyl phosphoramidites and the above prepared OligoPrep solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 38

Synthesis of 5'-d(TCC-CGC-CTG-TGA-CAT-GCA-TT)-3' (SEQ ID NO: 1) DNA 20-mer using 4: Synthesis of above sequence was performed on an Amersham Biosciences' Akta OligoPilot DNA/RNA Synthesizer on a 184 micromole scale using cyanoethyl phosphoramidites and the above prepared OligoPrep solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55

Experiment 39

Synthesis of 5'-d(TCC-CGC-CTG-TGA-CAT-GCA-TT)-3' (SEQ ID NO: 1) DNA 20-mer using 4': Synthesis of above sequence was performed on an Amersham Biosciences' Akta OligoPilot DNA/RNA Synthesizer on a 179 micromole scale using cyanoethyl phosphoramidites and the above prepared OligoPrep solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 40

Synthesis of 5'-d(GCC-CAA-GCT-GGC-ATC-CGT-CA)-3' (SEQ ID NO: 2) DNA 20-mer using 4: Synthesis of above sequence was performed on an Amersham Biosciences' Akta OligoPilot DNA/RNA Synthesizer on a 180 micromole scale using cyanoethyl phosphoramidites and the above prepared OligoPrep solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 41

Synthesis of 5'-d(GCC-CAA-GCT-GGC-ATC-CGT-CA)-3' (SEQ ID NO: 2) DNA 20-mer using 4': Synthesis of above sequence was performed on an Amersham Biosciences' Akta OligoPilot DNA/RNA Synthesizer on a 169 micromole scale using cyanoethyl phosphoramidites and the above prepared OligoPrep solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 42

Synthesis of fully-modified 5'-d(TCC-CGC-CTG-TGA-CAT-GCA-TT)-3' (SEQ ID NO: 1)phosphorothioate 20-mer using 4: Synthesis of above sequence was performed on an Amersham Biosciences' Akta OligoPilot DNA/RNA Synthesizer on a 172 micromole scale using cyanoethyl phosphoramidites and the above prepared Nittomar 250 solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 43

Synthesis of fully-modified 5'-d(TCC-CGC-CTG-TGA-CAT-GCA-TT)-3' (SEQ ID NO: 1) phosphorothioate 20-mer using 4': Synthesis of above sequence was performed on an Amersham Biosciences' Akta OligoPilot DNA/RNA Synthesizer on a 175 micromole scale using cyanoethyl phosphoramidites and the above prepared Nittomar 250 solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 44

Synthesis of fully-modified 5'-d(GCC-CAA-GCT-GGC-ATC-CGT-CA)-3' (SEQ ID NO: 2) phosphorothioate 20-mer using 4: Synthesis of above sequence was performed on an Amersham Biosciences' Akta OligoPilot DNA/RNA Synthesizer on a 178 micromole scale using cyanoethyl phosphoramidites and the above prepared Nittomar 250 solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 45

Synthesis of fully-modified 5'-d(GCC-CAA-GCT-GGC-ATC-CGT-CA)-3' (SEQ ID NO: 2) phosphorothioate 20-mer using 4': Synthesis of above sequence was performed on an Amersham Biosciences' Akta OligoPilot DNA/RNA Synthesizer on a 181 micromole scale using cyanoethyl phosphoramidites and the above prepared Nittomar 250 solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 46

Synthesis of 5'-d(TCC-CGC-CTG-TGA-CAT-GCA-TT)-3' (SEQ ID NO: 1) DNA 20-mer using 4: Synthesis of above sequence was performed on an Amersham Biosciences' Akta OligoPilot DNA/RNA Synthesizer on a 184 micromole scale using cyanoethyl phosphoramidites and the above prepared Nittomar 250 solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 47

Synthesis of 5'-d(TCC-CGC-CTG-TGA-CAT-GCA-TT)-3' (SEQ ID NO: 1) DNA 20-mer using 4': Synthesis of above sequence was performed on an Amersham Biosciences' Akta OligoPilot DNA/RNA Synthesizer on a 179 micromole scale using cyanoethyl phosphoramidites and the above prepared Nittomar 250 solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 48

Synthesis of 5'-d(GCC-CAA-GCT-GGC-ATC-CGT-CA)-3' (SEQ ID NO: 2) DNA 20-mer using 4: Synthesis of above sequence was performed on an Amersham Biosciences' Akta OligoPilot DNA/RNA Synthesizer on a 180 micromole scale using cyanoethyl phosphoramidites and the above prepared Nittomar 250 solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 49

Synthesis of 5'-d(GCC-CAA-GCT-GGC-ATC-CGT-CA)-3' (SEQ ID NO: 2) DNA 20-mer using 4': Synthesis of above sequence was performed on an Amersham Biosciences' Akta OligoPilot DNA/RNA Synthesizer on a 169 micromole scale using cyanoethyl phosphoramidites and the above prepared Nittomar 250 solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 50

Synthesis of fully-modified 5'-[2'-O-methoxyethyl-(TGTG]-d(CTA-TTC-TGT-G-)-[2'-O-methoxyethyl-(AATT]-3' (SEQ ID NO: 3) phosphorothioate 18-mer using 4: Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 51

Synthesis of fully-modified 5'-[2'-O-methoxyethyl-(TGTG]-d(CTA-TTC-TGT-G-)-[2'-O-methoxyethyl-(AATT]-3' (SEQ ID NO: 3) phosphorothioate 18-mer using 4': Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 52

Synthesis of fully-modified 5'-[2'-O-methoxyethyl-(GC-CTC]-d(AGT-CTG-CTT-C-)-[2'-O-methoxyethyl-(GCACC]-3' (SEQ ID NO: 4) phosphorothioate 20-mer using 4: Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 53

Synthesis of fully-modified 5'-[2'-O-methoxyethyl-(GC-CTC]-d(AGT-CTG-CTT-C-)-[2'-O-methoxyethyl-(GCACC]-3' (SEQ ID NO: 4) phosphorothioate 20-mer using 4': Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 54

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester using 4: Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 55

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester using 4': Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 56

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester using 4: Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 57

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester using 4': Synthesis of above sequence was performed on an ABI 390Z DNA/RNA Synthesizer on a 15 micromole scale using cyanoethyl phosphoramidites and the above prepared CPG solid support. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 58

Synthesis of fully-modified 5'-[2'-O-methoxyethyl-(TGTG]-d(CTA-TTC-TGT-G-)-[2'-O-methoxyethyl-(AATT]-3' (SEQ ID NO: 4) phosphorothioate 18-mer using 4: Synthesis of above sequence was performed on an Amersham Biosciences' Akta OligoPilot DNA/RNA Synthesizer on a 172 micromole scale using cyanoethyl phosphoramidites and the above prepared HL30 Primer solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 59

Synthesis of fully-modified 5'-[2'-O-methoxyethyl-(TGTG]-d(CTA-TTC-TGT-G-)-[2'-O-methoxyethyl-(AATT]-3' (SEQ ID NO: 4) phosphorothioate 18-mer using 4': Synthesis of above sequence was performed on an Amersham Biosciences' Akta OligoPilot DNA/RNA Synthesizer on a 175 micromole scale using cyanoethyl phosphoramidites and the above prepared HL30 Primer solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 60

Synthesis of fully modified 5'-[2'-O-methoxyethyl-(GCCTC]-d(AGT-CTG-CTT-C-)-[2'-O-methoxyethyl-(GCACC]-3' (SEQ ID NO: 4) phosphorothioate 20-mer using 4: Synthesis of above sequence was performed on an Amersham Biosciences' Akta OligoPilot DNA/RNA Synthesizer on a 178 micromole scale using cyanoethyl phosphoramidites and the above prepared HL30 Primer solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 61

Synthesis of fully-modified 5'-[2'-O-methoxyethyl-(GCCTC]-d(AGT-CTG-CTT-C-)-[2'-O-methoxyethyl-(GCACC]-3' (SEQ ID NO: 4) phosphorothioate 20-mer using 4': Synthesis of above sequence was performed on an Amersham Biosciences' Akta OligoPilot DNA/RNA Synthesizer on a 181 micromole scale using cyanoethyl phosphoramidites and the above prepared HL30 Primer solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 62

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester using 4: Synthesis of above sequence was performed on an Amersham Biosciences' Akta OligoPilot DNA/RNA Synthesizer on a 184 micromole scale using cyanoethyl phosphoramidites and the above prepared HL30 Primer solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 63

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester using 4': Synthesis of above sequence was performed on an Amersham Biosciences' Akta OligoPilot DNA/RNA Synthesizer on a 179 micromole scale using cyanoethyl phosphoramidites and the above prepared HL30 Primer solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 64

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester using 4: Synthesis of above sequence was performed on an Amersham Biosciences' Akta OligoPilot DNA/RNA Synthesizer on a 180 micromole scale using cyanoethyl phosphoramidites and the above prepared HL30 Primer solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 65

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester using 4': Synthesis of above sequence was performed on an Amersham Biosciences' Akta OligoPilot DNA/RNA Synthesizer on a 169 micromole scale using cyanoethyl phosphoramidites and the above prepared HL30 Primer solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 66

Synthesis of fully-modified 5'-[2'-O-methoxyethyl-(TGTG]-d(CTA-TTC-TGT-G-)-[2'-O-methoxyethyl-(AATT]-3' (SEQ ID NO: 3) phosphorothioate 18-mer using 4: Synthesis of above sequence was performed on an Amersham Biosciences' Akta OligoPilot DNA/RNA Synthesizer on a 172 micromole scale using cyanoethyl phosphoramidites and the above prepared OligoPrep solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 67

Synthesis of fully-modified 5'-[2'-O-methoxyethyl-(TGTG]-d(CTA-TTC-TGT-G-)-[2'-O-methoxyethyl-(AATT]-3' (SEQ ID NO: 3) phosphorothioate 18-mer using 4': Synthesis of above sequence was performed on an Amersham Biosciences' Akta OligoPilot DNA/RNA Synthesizer on a 175 micromole scale using cyanoethyl phosphoramidites and the above prepared OligoPrep solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 68

Synthesis of fully modified 5'-[2'-O-methoxyethyl-(GCCTC]-d(AGT-CTG-CTT-C-)-[2'-O-methoxyethyl-(GCACC]-3' (SEQ ID NO: 4) phosphorothioate 20-mer using 4: Synthesis of above sequence was performed on an Amersham Biosciences' Akta OligoPilot DNA/RNA Synthesizer on a 178 micromole scale using cyanoethyl phosphoramidites and the above prepared OligoPrep solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 69

Synthesis of fully modified 5'-[2'-O-methoxyethyl-(GCCTC]-d(AGT-CTG-CTT-C-)-[2'-O-methoxyethyl-(GCACC]-3' (SEQ ID NO: 4) phosphorothioate 20-mer using 4': Synthesis of above sequence was performed on an Amersham Biosciences' Akta OligoPilot DNA/RNA Synthesizer on a 181 micromole scale using cyanoethyl phosphoramidites and the above prepared OligoPrep solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 70

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester using 4: Synthesis of above sequence was performed on an Amersham Biosciences' Akta OligoPilot DNA/RNA Synthesizer on a 184 micromole scale using cyanoethyl phosphoramidites and the above prepared OligoPrep solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 71

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester using 4': Synthesis of above sequence was performed on an Amersham Biosciences' Akta OligoPilot DNA/RNA Synthesizer on a 179 micromole scale using cyanoethyl phosphoramidites and the above prepared OligoPrep solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 72

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester using 4: Synthesis of above sequence was performed on an Amersham Biosciences' Akta OligoPilot DNA/RNA Synthesizer on a 180 micromole scale using cyanoethyl phosphoramidites and the above prepared OligoPrep solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 73

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester using 4': Synthesis of above sequence was performed on an Amersham Biosciences' Akta OligoPilot DNA/RNA Synthesizer on a 169 micromole scale using cyanoethyl phosphoramidites and the above prepared OligoPrep solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 74

Synthesis of fully-modified 5'-[2'-O-methoxyethyl-(TGTG]-d(CTA-TTC-TGT-G-)-[2'-O-methoxyethyl-(AATT]-3' (SEQ ID NO: 3) phosphorothioate 18-mer using 4: Synthesis of above sequence was performed on an Amersham Biosciences' Akta OligoPilot DNA/RNA Synthesizer on a 172 micromole scale using cyanoethyl phosphoramidites and the above prepared Nittomar 250 solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 75

Synthesis of fully-modified 5'-[2'-O-methoxyethyl-(TGTG]-d(CTA-TTC-TGT-G-)-[2'-O-methoxyethyl-(AATT]-3' (SEQ ID NO: 3) phosphorothioate 18-mer using 4': Synthesis of above sequence was performed on an Amersham Biosciences' Akta OligoPilot DNA/RNA Synthesizer on a 175 micromole scale using cyanoethyl phosphoramidites and the above prepared Nittomar 250 solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 76

Synthesis of fully-modified 5'-[2'-O-methoxyethyl-(GCCTC]-d(AGT-CTG-CTT-C-)-[2'-O-methoxyethyl-(GCACC]-3' (SEQ ID NO: 4) phosphorothioate 20-mer using 4: Synthesis of above sequence was performed on an Amersham Biosciences' Akta OligoPilot DNA/RNA Synthesizer on a 178 micromole scale using cyanoethyl phosphoramidites and the above prepared Nittomar 250 solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 77

Synthesis of fully-modified 5'-[2'-O-methoxyethyl-(GCCTC]-d(AGT-CTG-CTT-C-)-[2'-O-methoxyethyl-(GCACC]-3' (SEQ ID NO: 4) phosphorothioate 20-mer using 4': Synthesis of above sequence was performed on an Amersham Biosciences' Akta OligoPilot DNA/RNA Synthesizer on a 181 micromole scale using cyanoethyl phosphoramidites and the above prepared Nittomar 250 solid support. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 78

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester using 4: Synthesis of above sequence was performed on an Amersham Biosciences' Akta OligoPilot DNA/RNA Synthesizer on a 184 micromole scale using cyanoethyl phosphoramidites and the above prepared Nittomar 250 solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 79

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester using 4': Synthesis of above sequence was performed on an Amersham Biosciences' Akta OligoPilot DNA/RNA Synthesizer on a 179 micromole scale using cyanoethyl phosphoramidites and the above prepared Nittomar 250 solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 80

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester using 4: Synthesis of above sequence was performed on an Amersham Biosciences' Akta OligoPilot DNA/RNA Synthesizer on a 180 micromole scale using cyanoethyl phosphoramidites and the above prepared Nittomar 250 solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 81

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester using 4': Synthesis of above sequence was performed on an Amersham Biosciences' Akta OligoPilot DNA/RNA Synthesizer on a 169 micromole scale using cyanoethyl phosphoramidites and the above prepared Nittomar 250 solid support. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 82

Reaction of DMT protected compound 3 with sebacic anhydride: DMT protected hydroxy compound 3 (FW 578; 49.13 g; 85 mmole) was dissolved in a mixture ethyl acetate: methylene chloride (600:66=666 mL). Triethyl amine (FW 101.19; 51.61 g; 71 mL; 0.51 mole; 6 equivalent with respect to starting DMT compound) was added and stirred magnetically at room temperature. To this clear solution, sebacic anhydride (0.34 mole, 4 equivalents with respect to starting DMT compound) was added as solid all at once. Stirring was continued overnight. TLC indicated disappearance of starting material. If starting material is seen, more of succinic anhydride is added till completion of reaction. The reaction mixture was diluted with ethyl acetate (300 mL) and washed with water (2×200 mL), brine (120 mL) and dried with magnesium sulfate. If the product is colored, the material is passed through a short pad of silica gel eluting with methylene chloride and then 5% methanol:95% methylene chloride to afford the product as a colorless product. Yield of 4a: 60.5 g (91%).

Experiment 83

Loading of DMT protected sebaciate 4a to controlled pore glass: Loading of the sebaciate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=40 micromole/gram.

Experiment 84

Loading of DMT protected sebaciate 4a to HL30 amino-derivatized primer support: Loading of the sebaciate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=90 micromole/gram.

Experiment 85

Loading of DMT protected succinate 4a to OligoPrep: Loading of the succinate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=244 micromole/gram.

Experiment 86

Loading of DMT protected sebaciate 4a to Nittomar 200 solid support: Loading of the sebaciate molecule was performed similar to nucleoside succinate using HBTU as activator and Hunig's base in acetonitrile as solvent. The unreacted sites were capped with acetic anhydride in pyridine in presence of DMAP as catalyst. Loading was then checked using the standard UV method. Loading=200 micromole/gram.

Experiment 87

Synthesis of fully-modified 5'-d(TCC-CGC-CTG-TGA-CAT-GCA-TT)-3' (SEQ ID NO: 1) phosphorothioate 20-mer: Synthesis of above sequence was performed on an ABI 390Z DNA/RNA Synthesizer on a 15 micromole scale using cyanoethyl phosphoramidites and the above prepared CPG solid support derivatized with 4a. Detritylation was performed

Experiment 88

Synthesis of fully-modified 5'-d(GCC-CAA-GCT-GGC-ATC-CGT-CA)-3' (SEQ ID NO: 2) phosphorothioate 20-mer: Synthesis of above sequence was performed on an ABI 390Z DNA/RNA Synthesizer on a 15 micromole scale using cyanoethyl phosphoramidites and the above prepared CPG solid support derivatized with 4a. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 89

Synthesis of 5'-d(TCC-CGC-CTG-TGA-CAT-GCA-TT)-3' (SEQ ID NO: 1) DNA 20-mer: Synthesis of above sequence was performed on an ABI 390Z DNA/RNA Synthesizer on a 15 micromole scale using cyanoethyl phosphoramidites and the above prepared CPG solid support derivatized with 4a. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 90

Synthesis of 5'-d(GCC-CAA-GCT-GGC-ATC-CGT-CA)-3' (SEQ ID NO: 2) DNA 20-mer: Synthesis of above sequence was performed on an ABI 390Z DNA/RNA Synthesizer on a 15 micromole scale using cyanoethyl phosphoramidites and the above prepared CPG solid support derivatized with 4a. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 91

Synthesis of fully-modified 5'-d(TCC-CGC-CTG-TGA-CAT-GCA-TT)-3' (SEQ ID NO: 1) phosphorothioate 20-mer: Synthesis of above sequence was performed on an Amersham Biosciences' Akta OligoPilot DNA/RNA Synthesizer on a 172 micromole scale using cyanoethyl phosphoramidites and the above prepared HL30 Primer solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 92

Synthesis of fully-modified 5'-d(GCC-CAA-GCT-GGC-ATC-CGT-CA)-3' (SEQ ID NO: 2) phosphorothioate 20-mer: Synthesis of above sequence was performed on an Amersham Biosciences' Akta OligoPilot DNA/RNA Synthesizer on a 178 micromole scale using cyanoethyl phosphoramidites and the above prepared HL30 Primer solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 93

Synthesis of 5'-d(TCC-CGC-CTG-TGA-CAT-GCA-TT)-3' (SEQ ID NO: 1) DNA 20-mer: Synthesis of above sequence was performed on an Amersham Biosciences' Akta OligoPilot DNA/RNA Synthesizer on a 184 micromole scale using cyanoethyl phosphoramidites and the above prepared HL30 Primer solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 94

Synthesis of 5'-d(GCC-CAA-GCT-GGC-ATC-CGT-CA)-3' (SEQ ID NO: 2) DNA 20-mer: Synthesis of above sequence was performed on an Amersham Biosciences' Akta OligoPilot DNA/RNA Synthesizer on a 180 micromole scale using cyanoethyl phosphoramidites and the above prepared HL30 Primer solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 95

Synthesis of fully-modified 5'-d(TCC-CGC-CTG-TGA-CAT-GCA-TT)-3' (SEQ ID NO: 1) phosphorothioate 20-mer: Synthesis of above sequence was performed on an Amersham Biosciences' Akta OligoPilot DNA/RNA Synthesizer on a 172 micromole scale using cyanoethyl phosphoramidites and the above prepared OligoPrep solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 96

Synthesis of fully-modified 5'-d(GCC-CAA-GCT-GGC-ATC-CGT-CA)-3' (SEQ ID NO: 2) phosphorothioate 20-mer: Synthesis of above sequence was performed on an Amersham Biosciences' Akta OligoPilot DNA/RNA Synthesizer on a 178 micromole scale using cyanoethyl phosphoramidites and the above prepared OligoPrep solid support derivatized with 4a. Detritylation was performed using 10% dichloroacetic acid in toluene (volume/volume). Sulfurization was performed using a 0.2 M solution of phenylacetyl disulfide in acetonitrile:3 picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 97

Synthesis of fully-modified 5'-d(GCC-CAA-GCT-GGC-ATC-CGT-CA)-3' (SEQ ID NO: 2) phosphorothioate 20-mer: Synthesis of above sequence was performed on an Amersham Biosciences' Akta OligoPilot DNA/RNA Synthesizer on a 178 micromole scale using cyanoethyl phosphoramidites and the above prepared OligoPrep solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 98

Synthesis of 5'-d(GCC-CAA-GCT-GGC-ATC-CGT-CA)-3' (SEQ ID NO: 2) DNA 20-mer: Synthesis of above sequence was performed on an Amersham Biosciences' Akta OligoPilot DNA/RNA Synthesizer on a 180 micromole scale using cyanoethyl phosphoramidites and the above prepared OligoPrep solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 99

Synthesis of fully-modified 5'-d(TCC-CGC-CTG-TGA-CAT-GCA-TT)-3' (SEQ ID NO: 1) phosphorothioate 20-mer: Synthesis of above sequence was performed on an Amersham Biosciences' Akta OligoPilot DNA/RNA Synthesizer on a 172 micromole scale using cyanoethyl phosphoramidites and the above prepared Nittomar 200 solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 100

Synthesis of fully-modified 5'-d(GCC-CAA-GCT-GGC-ATC-CGT-CA)-3' (SEQ ID NO: 2) phosphorothioate 20-mer: Synthesis of above sequence was performed on an Amersham Biosciences' Akta OligoPilot DNA/RNA Synthesizer on a 178 micromole scale using cyanoethyl phosphoramidites and the above prepared Nittomar 2-0 solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 101

Synthesis of 5'-d(TCC-CGC-CTG-TGA-CAT-GCA-TT)-3' (SEQ ID NO: 1) DNA 20-mer: Synthesis of above sequence was performed on an Amersham Biosciences' Akta OligoPilot DNA/RNA Synthesizer on a 184 micromole scale using cyanoethyl phosphoramidites and the above prepared Nittomar 200 solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 102

Synthesis of 5'-d(GCC-CAA-GCT-GGC-ATC-CGT-CA)-3' (SEQ ID NO: 2) DNA 20-mer: Synthesis of above sequence was performed on an Amersham Biosciences' Akta OligoPilot DNA/RNA Synthesizer on a 180 micromole scale using cyanoethyl phosphoramidites and the above prepared Nittomar 200 solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 103

Synthesis of fully-modified 5'-[2'-O-methoxyethyl-(TGTG]-d(CTA-TTC-TGT-G-)-[2'-O-methoxyethyl- (AATT]-3' (SEQ ID NO: 3) phosphorothioate 18-mer: Synthesis of above sequence was performed on an ABI 390Z DNA/RNA Synthesizer on a 15 micromole scale using cyanoethyl phosphoramidites and the above prepared CPG solid support derivatized with 4a. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 104

Synthesis of fully-modified 5'-[2'-O-methoxyethyl-(GC-CTC]-d(AGT-CTG-CTT-C-)-[2'-O-methoxyethyl-(GCACC]-3' (SEQ ID NO: 4) phosphorothioate 20-mer: Synthesis of above sequence was performed on an ABI 390Z DNA/RNA Synthesizer on a 15 micromole scale using cyanoethyl phosphoramidites and the above prepared CPG solid support derivatized with 4a. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 105

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester: Synthesis of above sequence was performed on an ABI 390Z DNA/RNA Synthesizer on a 15 micromole scale using cyanoethyl phosphoramidites and the above prepared CPG solid support derivatized with 4a. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 106

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester: Synthesis of above sequence was performed on an ABI 390Z DNA/RNA Synthesizer on a 15 micromole scale using cyanoethyl phosphoramidites and the above prepared CPG solid support derivatized with 4a. Detritylation was performed using 3% dichloroacetic acid in toluene (volume/volume). Oxidation was performed using a solution of iodine in THF/water/pyridine as recommended by ABI manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 107

Synthesis of fully-modified 5'-[2'-O-methoxyethyl-(TGTG]-d(CTA-TTC-TGT-G-)-[2'-O-methoxyethyl-(AATT]-3' (SEQ ID NO: 3) phosphorothioate 18-mer: Synthesis of above sequence was performed on an Amersham Biosciences' Akta OligoPilot DNA/RNA Synthesizer on a 172 micromole scale using cyanoethyl phosphoramidites and the above prepared HL30 Primer solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 108

Synthesis of fully modified 5'-[2'-O-methoxyethyl-(GC-CTC]-d(AGT-CTG-CTT-C-)-[2'-O-methoxyethyl-(GCACC]-3' (SEQ ID NO: 4) phosphorothioate 20-mer: Synthesis of above sequence was performed on an Amersham Biosciences' Akta OligoPilot DNA/RNA Synthesizer on a 178 micromole scale using cyanoethyl phosphoramidites and the above prepared HL30 Primer solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 109

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester: Synthesis of above sequence was performed on an Amersham Biosciences' Akta OligoPilot DNA/RNA Synthesizer on a 184 micromole scale using cyanoethyl phosphoramidites and the above prepared HL30 Primer solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 110

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester: Synthesis of above sequence was performed on an Amersham Biosciences' Akta OligoPilot DNA/RNA Synthesizer on a 180 micromole scale using cyanoethyl phosphoramidites and the above prepared HL30 Primer solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 111

Synthesis of fully-modified 5'-[2'-O-methoxyethyl-(TGTG]-d(CTA-TTC-TGT-G-)-[2'-O-methoxyethyl-(AATT]-3' (SEQ ID NO: 3) phosphorothioate 18-mer: Synthesis of above sequence was performed on an Amersham Biosciences' Akta OligoPilot DNA/RNA Synthesizer on a 172 micromole scale using cyanoethyl phosphoramidites and the above prepared OligoPrep solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 112

Synthesis of fully modified 5'-[2'-O-methoxyethyl-(GCCTC]-d(AGT-CTG-CTT-C-)-[2'-O-methoxyethyl-(GCACC]-3' (SEQ ID NO: 4) phosphorothioate 20-mer: Synthesis of above sequence was performed on an Amersham Biosciences' Akta OligoPilot DNA/RNA Synthesizer on a 178 micromole scale using cyanoethyl phosphoramidites and the above prepared OligoPrep solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 113

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester: Synthesis of above sequence was performed on an Amersham Biosciences' Akta OligoPilot DNA/RNA Synthesizer on a 184 micromole scale using cyanoethyl phosphoramidites and the above prepared OligoPrep solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 114

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester: Synthesis of above sequence was performed on an Amersham Biosciences' Akta OligoPilot DNA/RNA Synthesizer on a 180 micromole scale using cyanoethyl phosphoramidites and the above prepared OligoPrep solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 115

Synthesis of fully-modified 5'-[2'-O-methoxyethyl-(TGTG]-d(CTA-TTC-TGT-G-)-[2'-O-methoxyethyl-(AATT]-3' (SEQ ID NO: 3) phosphorothioate 18-mer: Synthesis of above sequence was performed on an Amersham Biosciences' Akta OligoPilot DNA/RNA Synthesizer on a 172 micromole scale using cyanoethyl phosphoramidites and the above prepared Nittomar 200 solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 116

Synthesis of fully-modified 5'-[2'-O-methoxyethyl-(GCCTC]-d(AGT-CTG-CTT-C-)-[2'-O-methoxyethyl-(GCACC]-3' (SEQ ID NO: 4) phosphorothioate 20-mer: Synthesis of above sequence was performed on an Amersham Biosciences' Akta OligoPilot DNA/RNA Synthesizer on a 178 micromole scale using cyanoethyl phosphoramidites and the above prepared Nittomar 200 solid support derivatized with 4a. Detritylation was performed using 10% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected using ammonium hydroxide at 55 deg C. for 12 hours. The crude oligo was purified in the usual manner to afford the desired phosphorothioate oligonucleotide.

Experiment 117

Synthesis of 5'-[2'-O-methoxyethyl-(TGTG]-d(CTA-TTC-TGT-G-)-[2'-O-methoxyethyl-(AATT]-3' (SEQ ID NO: 3) 18-mer phosphate diester: Synthesis of above sequence was performed on an Amersham Biosciences' Akta OligoPilot DNA/RNA Synthesizer on a 184 micromole scale using cyanoethyl phosphoramidites and the above prepared Nittomar 200 solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

Experiment 118

Synthesis of 5'-[2'-O-methoxyethyl-(GCCTC]-d(AGT-CTG-CTT-C-)-[2'-O-methoxyethyl-(GCACC]-3' (SEQ ID NO: 4) 20-mer phosphate diester: Synthesis of above sequence was performed on an Amersham Biosciences' Akta OligoPilot DNA/RNA Synthesizer on a 180 micromole scale using cyanoethyl phosphoramidites and the above prepared Nittomar 200 solid support derivatized with 4a. Detritylation was performed using 10% dichloroacetic acid in toluene (volume/volume). Oxidation was performed using a solution of iodine in THF/water/pyridine as recommended by instrument manual protocol. At the end of synthesis, the support was washed with acetonitrile, cleaved, deprotected using ammonium hydroxide at 55 deg C. for 12 hours. The crude oligo was purified in the usual manner to afford the desired oligonucleotide.

All references cited herein, including and not limited to publications, patents, patent applications and books, are expressly incorporated herein by reference in their entirety.

What is claimed is:

1. A compound of the formula I:

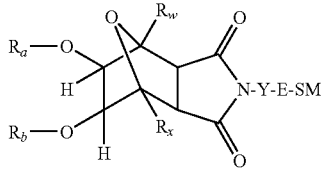

wherein:

$R_w$ and $R_x$ are each, independently, H, alkyl or substituted alkyl;

$R_a$ and $R_b$ are each, independently, H, a protecting group, a protected or unprotected nucleosidyl moiety, a protected or unprotected nucleosidyl moiety attached through a phospholinker, or a protected or unprotected oligonucleotidyl moiety;

Y is alkylene, cycloalkylene, arylene, heteroarylene, arylalkylene, alkarylene, or alkylenearylalkylene;

E is a bond, $(CH_2)_iC(=O)$ or $C(=O)(CH_2)_jC(=O)$ wherein i is from 0 to 20 and j is from 1 to 20; and SM is a support medium.

2. The compound of claim 1 wherein Y is arylene, heteroarylene or arylalkylene.

3. The compound of claim 2 wherein Y is arylene or heteroarylene.

4. The compound of claim 3 wherein Y is arylene.

5. The compound of claim 4 wherein Y is phenylene.

6. The compound of claim 5 wherein Y is 1,4-phenylene.

7. The compound of claim 2 wherein Y is arylalkylene.

8. The compound of claim 7 wherein Y is benzylene.

9. The compound of claim 8 wherein Y is 1,4-benzylene.

10. The compound of claim 4 wherein E is $(CH_2)_iC(=O)$.

11. The compound of claim 10 wherein i is 0.

12. The compound of claim 11 wherein Y is 1,4-phenylene.

13. The compound of claim 4 wherein E is $C(=O)(CH_2)_jC(=O)$.

14. The compound of claim 13 wherein j is 2.

15. The compound of claim 1 wherein one of $R_a$ and $R_b$ is a base labile hydroxyl protecting group.

16. The compound of claim 15 wherein the other of $R_a$ and $R_b$ is an acid labile hydroxyl protecting group.

17. The compound of claim 16 wherein $R_a$ is an acid labile hydroxyl protecting group and $R_b$ is a base labile hydroxyl protecting group.

18. The compound of claim 17 wherein the acid labile hydroxyl protecting group is 4-methoxytriphenylmethyl, 4,4'-dimethoxytriphenylmethyl, 9-phenylxanthenyl or substituted 9-phenylxanthenyl.

19. The compound of claim 18 wherein the acid labile hydroxyl protecting group is 4,4'-dimethoxytriphenylmethyl.

20. The compound of claim 19 wherein the base labile hydroxyl protecting group is an acyl group.

21. The compound of claim 20 wherein the base labile hydroxyl protecting group is benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl or benzoyl.

22. The compound of claim 21 wherein the base labile hydroxyl protecting group is acetyl.

23. The compound of claim 1 wherein the support material is controlled pore glass, oxalyl-controlled pore glass, silica-containing particles, polystyrene, copolymers of polystyrene, and divinylbenzene, copolymers of dimethylacrylamide and N,N-bisacryloylethylenediamine, a soluble support medium or PEPS.

24. The compound of claim 23 wherein the support material is controlled pore glass, polystyrene or copolymers of polystyrene.

25. The compound of claim 1 wherein one of $R_w$, and $R_x$ is alkyl or substituted alkyl.

26. The compound of claim 1 wherein $R_w$ and $R_x$ are each H.

27. The compound of claim 26 wherein Y is 1,4-phenylene, E is $C(=O)$, one of $R_a$ and $R_b$ is an acid labile hydroxyl protecting group and the other of $R_a$ and $R_b$ is a base labile protecting group.

28. The compound of claim 27 wherein $R_a$ is an acid labile hydroxyl protecting group and $R_b$ is a base labile hydroxyl protecting group.

29. The compound of claim 28 wherein the acid labile hydroxyl protecting group is 4,4'-dimethoxytriphenylmethyl and the base labile hydroxyl protecting group is an acyl group.

30. The compound of claim 29 wherein the acyl group is $C(=O)CH_3$.

31. The compound of claim 30 wherein the support material is controlled pore glass, polystyrene or copolymers of polystyrene.

* * * * *

```
                    SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 1
tcccgcctgt gacatgcatt                                          20

<210> SEQ ID NO 2
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 2
gcccaagctg gcatccgtca                                          20

<210> SEQ ID NO 3
<211> LENGTH: 18
<212> TYPE: DNA
<213> ORGANISM: Artificial Sequence
<220> FEATURE:
<223> OTHER INFORMATION: Oligomeric Compound

<400> SEQUENCE: 3
tgtgctattc tgtgaatt                                            18

<210> SEQ ID NO 4
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 4
gcctcagtct gcttcgcacc                                          20
```